United States Patent
Lücking et al.

(10) Patent No.: US 9,108,926 B2
(45) Date of Patent: Aug. 18, 2015

(54) DISUBSTITUTED 5-FLUORO-PYRIMIDINES

(75) Inventors: Ulrich Lücking, Berlin (DE); Dirk Kosemund, Berlin (DE); Arne Scholz, Berlin (DE); Philip Lienau, Berlin (DE); Gerhard Siemeister, Berlin (DE); Ulf Bömer, Glienicke (DE); Rolf Bohlmann, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/343,983

(22) PCT Filed: Sep. 13, 2012

(86) PCT No.: PCT/EP2012/067966
§ 371 (c)(1),
(2), (4) Date: Mar. 10, 2014

(87) PCT Pub. No.: WO2013/037896
PCT Pub. Date: Mar. 21, 2013

(65) Prior Publication Data
US 2014/0228387 A1    Aug. 14, 2014

(30) Foreign Application Priority Data
Sep. 16, 2011 (EP) .................................. 11181545

(51) Int. Cl.
| | |
|---|---|
| *C07D 239/42* | (2006.01) |
| *C07D 401/12* | (2006.01) |
| *C07D 407/04* | (2006.01) |
| *A61K 31/505* | (2006.01) |
| *A61K 31/506* | (2006.01) |
| *C07D 405/04* | (2006.01) |

(52) U.S. Cl.
CPC ............ *C07D 239/42* (2013.01); *A61K 31/505* (2013.01); *A61K 31/506* (2013.01); *C07D 401/12* (2013.01); *C07D 405/04* (2013.01); *C07D 407/04* (2013.01)

(58) Field of Classification Search
CPC .. C07D 239/42; C07D 401/12; C07D 405/04; C07D 407/04; A61K 31/505; A61K 31/506

USPC .................................. 544/330, 332; 514/275
See application file for complete search history.

(56) References Cited

U.S. PATENT DOCUMENTS

2010/0093776 A1*  4/2010  Beckwith ....................... 514/275

FOREIGN PATENT DOCUMENTS

| WO | WO 2006/064251 | * | 6/2006 |
| WO | WO 2008/129070 | * | 10/2008 |

OTHER PUBLICATIONS

Simone, Oncology: Introduction, Cecil Textbook of Medicine, 20th Edition, vol. 1, pp. 1004-1101 O, 1996.*
Douglas, Jr., Introduction to Viral Diseases, Cecil Textbook of Medicine, 20th Edition, vol. 2, pp. 1739-1747, 1996.*
Bosseray et al., PubMed Abstract (Pathol Biol (Paris) 50(8):483-92), 2002.*
Goff, PubMed Abstract (J Gene Med. 3(6):517-28), 2001.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Razonable et al., PubMed Abstract (Herpes 10(3):60-5), 2003.*
Blain et al., Differential Interaction of the Cyclin-dependent Kinase (Cdk) Inhibitor p27Kip1 with Cyclin A-Cdk2 nad Cyclin D2-Cdk4, The Journal of Biological Chemistry, vol. 272, No. 41, pp. 25863-25872, 1997.*
LuValle et al., Cell Cycle Control in Growth Plate, Frontiers in Biosciences, 5, d493-503, May 2000.*

* cited by examiner

Primary Examiner — Deepak Rao

(57) ABSTRACT

The present invention relates to disubstituted 5-fluoro-pyrimidines of general formula (I) as described and defined herein, and methods for their preparation, their use for the treatment and/or prophylaxis of disorders, in particular of hyper-proliferative disorders and/or virally induced infectious diseases and/or of cardiovascular diseases. The invention further relates to intermediate compounds useful in the preparation of said compounds of general formula (I).

11 Claims, No Drawings

DISUBSTITUTED 5-FLUORO-PYRIMIDINES

The present invention relates to disubstituted 5-fluoro-pyrimidines of general formula (I) as described and defined herein, and methods for their preparation, their use for the treatment and/or prophylaxis of disorders, in particular of hyper-proliferative disorders and/or virally induced infectious diseases and/or of cardiovascular diseases. The invention further relates to intermediate compounds useful in the preparation of said compounds of general formula (I).

The family of cyclin-dependent kinase (CDK) proteins consists of members that are key regulators of the cell division cycle (cell cycle CDK's), that are involved in regulation of gene transcription (transcriptional CDK's), and of members with other functions. CDKs require for activation the association with a regulatory cyclin subunit. The cell cycle CDKs CDK1/cyclin B, CDK2/cyclin A, CDK2/cyclinE, CDK4/cyclinD, and CDK6/cyclinD get activated in a sequential order to drive a cell into and through the cell division cycle. The transcriptional CDKs CDK9/cyclin T and CDK7/cyclin H regulate the activity of RNApolymerase II via phosphorylation of the carboxy-terminal domain (CTD). Positive transcription factor b (P-TEFb) is a heterodimer of CDK9 and one of four cyclin partners, cyclin T1, cyclin K, cyclin T2a or T2b.

Whereas CDK9 (NCBI GenBank Gene ID 1025) is exclusively involved in transcriptional regulation, CDK7 in addition participates in cell cycle regulation as CDK-activating kinase (CAK).

Transcription of genes by RNA polymerase II is initiated by assembly of the pre-initiation complex at the promoter region and phosphorylation of Ser 5 and Ser 7 of the CTD by CDK7/cyclin H. For a major fraction of genes RNA polymerase II stops mRNA transcription after it moved 20-40 nucleotides along the DNA template. This promoter-proximal pausing of RNA polymerase II is mediated by negative elongation factors and is recognized as a major control mechanism to regulate expression of rapidly induced genes in response to a variety of stimuli (Cho et al., Cell Cycle 9, 1697, 2010). P-TEFb is crucially involved in overcoming promoter-proximal pausing of RNA polymerase II and transition into a productive elongation state by phosphorylation of Ser 2 of the CTD as well as by phosphorylation and inactivation of negative elongation factors.

Activity of P-TEFb itself is regulated by several mechanisms. About half of cellular P-TEFb exists in an inactive complex with 7SK small nuclear RNA (7SK snRNA), La-related protein 7 (LARP7/PIP7S) and hexamethylene bis-acetamide inducible proteins 1/2 (HEXIM1/2, He et al., Mol Cell 29, 588, 2008). The remaining half of P-TEFb exists in an active complex containing the bromodomain protein Brd4 (Yang et al., Mol Cell 19, 535, 2005). Brd4 recruits P-TEFb through interaction with acetylated histones to chromatin areas primed for gene transcription. Through alternately interacting with its positive and negative regulators, P-TEFb is maintained in a functional equilibrium: P-TEFb bound to the 7SK snRNA complex represents a reservoir from which active P-TEFb can be released on demand of cellular transcription and cell proliferation (Zhou & Yik, Microbiol Mol Biol Rev 70, 646, 2006). Furthermore, the activity of P-TEFb is regulated by posttranslational modifications including phosphorylation/de-phosphorylation, ubiquitination, and acetylation (reviewed in Cho et al., Cell Cycle 9, 1697, 2010).

Deregulated activity of CDK9 kinase activity of the P-TEFb heterodimer is associated with a variety of human pathological settings such as hyper-proliferative diseases (e.g. cancer), virally induced infectious diseases or cardiovascular diseases:

Cancer is regarded as a hyper-proliferative disorder mediated by a disbalance of proliferation and cell death (apoptosis). High levels of anti-apoptotic Bcl-2-family proteins are found in various human tumors and account for prolonged survival of tumor cells and therapy resistance. Inhibition of P-TEFb kinase activity was shown to reduce transcriptional activity of RNA polymerase II leading to a decline of short-lived anti-apoptotic proteins, especially Mcl-1 and XIAP, reinstalling the ability of tumor cells to undergo apoptosis. A number of other proteins associated with the transformed tumor phenotype (such as Myc, NF-kB responsive gene transcripts, mitotic kinases) are either short-lived proteins or are encoded by short-lived transcripts which are sensitive to reduced RNA polymerase II activity mediated by P-TEFb inhibition (reviewed in Wang & Fischer, Trends Pharmacol Sci 29, 302, 2008).

Many viruses rely on the transcriptional machinery of the host cell for the transcription of their own genome. In case of HIV-1, RNA polymerase II gets recruited to the promoter region within the viral LTR's. The viral transcription activator (Tat) protein binds to nascent viral transcripts and overcomes promoter-proximal RNA polymerase II pausing by recruitment of P-TEFb which in turn promotes transcriptional elongation. Furthermore, the Tat protein increases the fraction of active P-TEFb by replacement of the P-TEFb inhibitory proteins HEXIM1/2 within the 7SK snRNA complex. Recent data have shown that inhibition of the kinase activity of P-TEFb is sufficient to block HIV-1 replication at kinase inhibitor concentrations that are not cytotoxic to the host cells (reviewed in Wang & Fischer, Trends Pharmacol Sci 29, 302, 2008). Similarly, recruitment of P-TEFb by viral proteins has been reported for other viruses such as B-cell cancer-associated Epstein-Barr virus, where the nuclear antigen EBNA2 protein interacts with P-TEFb (Bark-Jones et al., Oncogene, 25, 1775, 2006), and the human T-lymphotropic virus type 1 (HTLV-1), where the transcriptional activator Tax recruits P-TEFb (Zhou et al., J Virol. 80, 4781, 2006).

Cardiac hypertrophy, the heart's adaptive response to mechanical overload and pressure (hemodynamic stress e.g. hypertension, myocardial infarction), can lead, on a long term, to heart failure and death. Cardiac hypertrophy was shown to be associated with increased transcriptional activity and RNA polymerase II CTD phosphorylation in cardiac muscle cells. P-TEFb was found to be activated by dissociation from the inactive 7SK snRNA/HEXIM1/2 complex. These findings suggest pharmacological inhibition of P-TEFb kinase activity as a therapeutic approach to treat cardiac hypertrophy (reviewed in Dey et al., Cell Cycle 6, 1856, 2007).

In summary, multiple lines of evidence suggest that selective inhibition of the CDK9 kinase activity of the P-TEFb heterodimer (=CDK9 and one of four cyclin partners, cyclin T1, cyclin K, cyclin T2a or T2b) represents an innovative approach for the treatment of diseases such as cancer, viral diseases, and/or diseases of the heart. CDK9 belongs to a family of at least 13 closely related kinases of which the subgroup of the cell cycle CDK's fulfills multiple roles in regulation of cell proliferation. Thus, co-inhibition of cell cycle CDKs (e.g. CDK1/cyclin B, CDK2/cyclin A, CDK2/cyclinE, CDK4/cyclinD, CDK6/cyclinD) and of CDK9, is expected to impact normal proliferating tissues such as intestinal mucosa, lymphatic and hematopoietic organs, and reproductive organs. To maximize the therapeutic margin of CDK9 kinase inhibitors, molecules with high selectivity towards CDK9 are required.

CDK inhibitors in general as well as CDK9 inhibitors are described in a number of different publications:

WO2008129070 and WO2008129071 both describe 2,4 disubstituted aminopyrimidines as CDK inhibitors in general. It is also asserted that some of these compounds may act as selective CDK9 inhibitors (WO2008129070) and as CDK5 inhibitors (WO2008129071), respectively, but no specific CDK9 $IC_{50}$ (WO2008129070) or CDK5 $IC_{50}$ (WO2008129071) data is presented. These compounds do not contain a fluoro atom in 5-position of the pyrimidine core.

WO2008129080 discloses 4,6 disubstituted aminopyrimidines and demonstrates that these compounds show an inhibitory effect on the protein kinase activity of various protein kinases, such as CDK1, CDK2, CDK4, CDK5, CDK6 and CDK9, with a preference for CDK9 inhibition (example 80).

WO2005026129 discloses 4,6 disubstituted aminopyrimidines and demonstrates that these compounds show an inhibitory effect on the protein kinase activity of various protein kinases, in particular CDK2, CDK4, and CDK9.

WO2011116951 discloses substituted triazine derivatives as selective CDK9 inhibitors.

EP1218360 B1, which corresponds to US2004116388A1, U.S. Pat. No. 7,074,789B2 and WO2001025220A1, describes triazine derivatives as kinase inhibitors, but does not disclose potent or selective CDK9 inhibitors.

WO2008079933 discloses aminopyridine and aminopyrimidine derivatives and their use as CDK1, CDK2, CDK3, CDK4, CDK5, CDK6, CDK7, CDK8 or CDK9 inhibitors.

WO2011012661 describes aminopyridine derivatives useful as CDK inhibitors.

WO2011026917 discloses carboxamides derived from substituted 4-phenylpyridine-2-amines as inhibitors of CDK9.

WO2012066065 discloses phenyl-heterorayl amines as inhibitors of CDK9. A selectivity towards CDK9 over other CDK isoforms is preferred, however disclosure of CDK-inhibition data is confined to CDK 9. No bicyclic ring systems are disclosed attached to the C4 position of the pyrimidine core. Within the group attached to C4 of the pyrimidine core, alkoxy phenyls can be regarded as encompassed, but there is no suggestion for a specific substitution pattern characterised by a fluoro atom attached to C5 of the pyrimidine ring, and an aniline at C2 of the pyrimidine, featuring a substituted sulfonyl-methylene group in meta position. Compounds shown in the examples typically feature a substituted cycloalkyl group as $R^1$ but no phenyl.

WO2012066070 discloses 3-(aminoaryl)-pyridine compounds as inhibitors of CDK9. The biaryl core mandatorily consists of two heteroaromatic rings.

WO2012101062 discloses substituted bi-heteroaryl compounds featuring a 2-aminopyridine core as inhibitors of CDK9. The biaryl core mandatorily consists of two heteroaromatic rings.

WO2012101063 discloses carboxamides derived from substituted 4-(heteroaryl)-pyridine-2-amines as inhibitors of CDK9.

WO 2012101064 discloses N-acyl pyrimidine biaryl compounds as inhibitors of CDK9.

WO 2012101065 discloses pyrimidine biaryl compounds as inhibitors of CDK9. The biaryl core mandatorily consists of two heteroaromatic rings.

WO 2012101066 discloses pyrimidine biaryl compounds as inhibitors of CDK9. Substitution $R^1$ of the amino group attached to the heteroaromatic core is confined to non-aromatic groups but does not cover substituted phenyls. Furthermore, the biaryl core mandatorily consists of two heteroaromatic rings.

Wang et al. (Chemistry & Biology 17, 1111-1121, 2010) describe 2-anilino-4-(thiazol-5-yl)pyrimidine transcriptional CDK inhibitors, which show anticancer activity in animal models.

WO2004009562 discloses substituted triazine kinase inhibitors. For selected compounds CDK1 and CDK4 test data, but no CDK9 data is presented.

WO2004072063 describes heteroaryl (pyrimidine, triazine) substituted pyrroles as inhibitors of protein kinases such as ERK2, GSK3, PICA or CDK2.

WO2010009155 discloses triazine and pyrimidine derivatives as inhibitors of histone deacetylase and/or cyclin dependent kinases (CDKs). For selected compounds CDK2 test data is described.

WO2003037346 (corresponding to U.S. Pat. No. 7,618, 968B2, U.S. Pat. No. 7,291,616B2, US2008064700A1, US2003153570A1) relates to aryl triazines and uses thereof, including to inhibit lysophosphatidic acid acyltransferase beta (LPAAT-beta) activity and/or proliferation of cells such as tumor cells.

WO2008025556 describes carbamoyl sulfoximides having a pyrimidine core, which are useful as kinase inhibitors. No CDK9 data is presented. No molecules are exemplified, which possess a fluoropyrimidine core.

WO2002066481 describes pyrimidine derivatives as cyclin dependent kinase inhibitors. CDK9 is not mentioned and no CDK9 data is presented.

WO2008109943 concerns phenyl aminopyri(mi)dine compounds and their use as kinase inhibitors, in particular as JAK2 kinase inhibitors. The specific examples mainly focus on compounds having a pyrimidine core.

WO2009032861 describes substituted pyrimidinyl amines as JNK kinase inhibitors. The specific examples mainly focus on compounds having a pyrimidine core.

WO2011046970 concerns amino-pyrimidine compounds as inhibitors of TBKL and/or IKK epsilon. The specific examples mainly focus on compounds having a pyrimidine core.

Despite the fact that various inhibitors of CDKs are known, there remains a need for selective CDK9 inhibitors to be used for the treatment of diseases such as hyper-proliferative diseases, viral diseases, and/or diseases of the heart, which offer one or more advantages over the compounds known from prior art, such as:
- improved activity and/or efficacy
- beneficial kinase selectivity profile according to the respective therapeutic need
- improved side effect profile, such as fewer undesired side effects, lower intensity of side effects, or reduced (cyto) toxicity
- improved physicochemical properties, such as solubility in water and body fluids
- improved pharmacokinetic properties, allowing e.g. for dose reduction or an easier dosing scheme
- easier drug substance manufacturing e.g. by shorter synthetic routes or easier purification.

A particular object of the invention is to provide CDK9 kinase inhibitors which, compared to the compounds known from prior art, show an increased selectivity for CDK9/Cyclin T1 as compared to CDK2/Cyclin E.

Another object of the invention is to provide CDK9 kinase inhibitors which show an increased potency to inhibit CDK9 activity (demonstrated by a lower $IC_{50}$ value for CDK9/Cyclin T1) compared to the compounds known from prior art.

Another object of the invention is to provide CDK9 kinase inhibitors which show an increased potency to inhibit CDK9 activity at high ATP concentrations compared to the compounds known from prior art.

Another object of the invention is to provide CDK9 kinase inhibitors, which show an improved anti-proliferative activity in tumor cell lines such as HeLa compared to the compounds known from prior art.

Further, it is also an object of the present invention to provide CDK9 kinase inhibitors, which, compared to the compounds known from prior art, are highly selective for CDK9/Cyclin T1 as compared to CDK2/Cyclin E, and/or which show an increased potency to inhibit CDK9 activity and/or which show an improved anti-proliferative activity in tumor cell lines such as HeLa and/or which show an increased potency to inhibit CDK9 activity at high ATP concentrations compared to the compounds known from prior art.

The present invention relates to compounds of general formula (I)

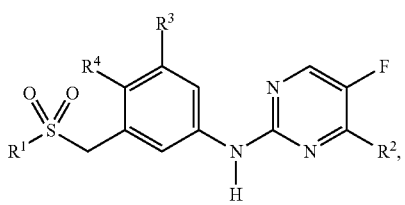

(I)

wherein $R^1$ represents a group selected from $C_1$-$C_6$-alkyl-, $C_3$-$C_7$-cycloalkyl-, heterocyclyl-, phenyl, heteroraryl, phenyl-$C_1$-$C_3$-alkyl- or heteroaryl-$C_1$-$C_3$-alkyl-,
   wherein said group is optionally substituted with one or two or three substituents, identically or differently, selected from the group of hydroxy, cyano, halogen, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amines;

$R^2$ represents a group selected from

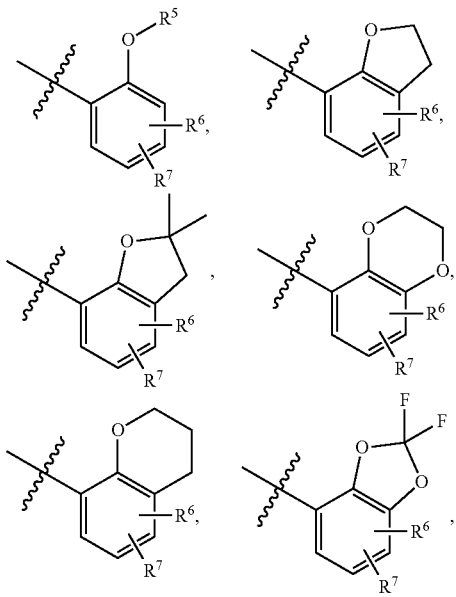

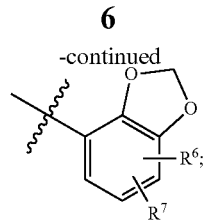

$R^3$, $R^4$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;

$R^5$ represents a group selected from
   a) a $C_1$-$C_6$-alkyl group, which is optionally substituted with one or two or three substituents, identically or differently, selected from halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, heterocyclyl-, phenyl, heteroaryl, wherein said $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;
   b) a $C_3$-$C_7$-cycloalkyl- group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-;
   c) a heterocyclyl-group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-;
   d) a phenyl group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
   e) a heteroaryl group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
   f) a phenyl-$C_1$-$C_3$-alkyl-group, which phenyl group is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
   g) a heteroaryl-$C_1$-$C_3$-alkyl-group, which heteroaryl group is optionally substituted with one or two or three substituents, identically or differently, selected from the group of halogen, hydroxy, —NH$_2$, alkylamino-, dialkylamino-, acetylamino-, N-methyl-N-acetylamino-, cyclic amines, cyano, C$_1$-C$_3$-alkyl-, halo-C$_1$-C$_3$-alkyl-, C$_1$-C$_3$-fluoroalkoxy-, C$_1$-C$_3$-alkoxy-;

h) a C$_3$-C$_6$-cycloalkyl-C$_1$-C$_3$-alkyl-group, which C$_3$-C$_6$-cycloalkyl group is optionally substituted with one or two or three substituents, identically or differently, selected from halogen, C$_1$-C$_3$-alkyl-, C$_1$-C$_3$-alkoxy-, halo-C$_1$-C$_3$-alkyl-, C$_1$-C$_3$-fluoroalkoxy-;

i) a heterocyclyl-C$_1$-C$_3$-alkyl-group, which heterocyclyl group is optionally substituted with one or two or three substituents, identically or differently, selected from halogen, C$_1$-C$_3$-alkyl-, C$_1$-C$_3$-alkoxy-, halo-C$_1$-C$_3$-alkyl-, C$_1$-C$_3$-fluoroalkoxy-;

j) phenyl-cyclopropyl-group, which phenyl group is optionally substituted with one or two or three substituents, identically or differently, selected from the group of halogen, hydroxy, NH$_2$, alkylamino-, dialkylamino-, acetylamino-, N-methyl-N-acetylamino-, cyclic amines, cyano, C$_1$-C$_3$-alkyl-, halo-C$_1$-C$_3$-alkyl-, C$_1$-C$_3$-fluoroalkoxy-, C$_1$-C$_3$-alkoxy-;

k) a heteroaryl-cyclopropyl-group, which heteroaryl group is optionally substituted with one or two or three substituents, identically or differently, selected from the group of halogen, hydroxy, NH$_2$, alkylamino-, dialkylamino-, acetylamino-, N-methyl-N-acetylamino-, cyclic amines, cyano, C$_1$-C$_3$-alkyl-, halo-C$_1$-C$_3$-alkyl-, C$_1$-C$_3$-fluoroalkoxy-, C$_1$-C$_3$-alkoxy-;

R$^6$, R$^7$ represent, independently from each other, a group selected from a hydrogen atom, fluoro atom, chloro atom, C$_1$-C$_3$-alkyl-, C$_1$-C$_3$-alkoxy-, halo-C$_1$-C$_3$-alkyl-, C$_1$-C$_3$-fluoroalkoxy-;

or their salts, solvates or salts of solvates.

Compounds according to the invention are the compounds of the formula (I) and the salts, solvates and solvates of the salts thereof, the compounds of the hereinafter recited formula which are encompassed by formula (I) and the salts, solvates and solvates of the salts thereof, and the compounds which are encompassed by formula (I) and are mentioned hereinafter as exemplary embodiments and the salts, solvates and solvates of the salts thereof, where the compounds which are encompassed by formula (I) and are mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

If the compounds according to the invention can be in tautomeric forms, the present invention encompasses all tautomeric forms.

Further, the compounds of the present invention can exist in free form, e.g. as a free base, or as a free acid, or as a zwitterion, or can exist in the form of a salt. Said salt may be any salt, either an organic or inorganic addition salt, particularly any physiologically acceptable organic or inorganic addition salt, customarily used in pharmacy.

Salts which are preferred for the purposes of the present invention are physiologically acceptable salts of the compounds according to the invention. However, salts which are not suitable for pharmaceutical applications per se, but which, for example, can be used for the isolation or purification of the compounds according to the invention, are also comprised.

The term "physiologically acceptable salt" refers to a relatively non-toxic, inorganic or organic acid addition salt of a compound of the present invention, for example, see S. M. Berge, et al. "Pharmaceutical Salts," J. Pharm. Sci. 1977, 66, 1-19.

Physiologically acceptable salts of the compounds according to the invention encompass acid addition salts of mineral acids, carboxylic acids and sulfonic acids, for example salts of hydrochloric acid, hydrobromic acid, hydroiodic, sulfuric acid, bisulfuric acid, phosphoric acid, nitric acid or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Physiologically acceptable salts of the compounds according to the invention also comprise salts of conventional bases, such as, by way of example and by preference, alkali metal salts (for example sodium and potassium salts), alkaline earth metal salts (for example calcium and magnesium salts) and ammonium salts derived from ammonia or organic amines with 1 to 16 C atoms, such as, by way of example and by preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, dimethylglucamine, ethylglucamine, 1,6-hexadiamine, glucosamine, sarcosine, serinol, tris(hydroxymethyl)aminomethane, aminopropanediol, Sovak base, and 1-amino-2,3,4-butanetriol. Additionally, basic nitrogen containing groups may be quaternised with such agents as lower alkylhalides such as methyl-, ethyl-, propyl-, and butylchlorides, -bromides and -iodides; dialkylsulfates like dimethyl-, diethyl-, dibutyl- and diamylsulfates, long chain halides such as decyl-, lauryl-, myristyl- and stearylchlorides, -bromides and -iodides, aralkylhalides like benzyl- and phenethylbromides and others.

The present invention includes all possible salts of the compounds of the present invention as single salts, or as any mixture of said salts, in any ratio.

Solvates is the term used for the purposes of the invention for those forms of the compounds according to the invention which form a complex with solvent molecules by coordination in the solid or liquid state. Hydrates are a special form of solvates in which the coordination takes place with water. Hydrates are preferred as solvates within the scope of the present invention.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulfur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

In addition, the present invention also encompasses prodrugs of the compounds according to the invention. The term "prodrugs" encompasses compounds which themselves may be biologically active or inactive, but are converted (for example by metabolism or hydrolysis) to compounds according to the invention during their residence time in the body.

For the purposes of the present invention, the substituents have the following meaning, unless otherwise specified:

The term "halogen atom" or "halo" represents fluorine, chlorine, bromine and iodine, particularly chlorine or fluorine, preferably fluorine.

The term "alkyl" represents a linear or branched alkyl radical having the number of carbon atoms specifically indicated, e.g. $C_1$-$C_{10}$ one, two, three, four, five, six, seven, eight, nine or ten carbon atoms, e.g. methyl, ethyl, n-propyl, isopropyl, n-butyl, isobutyl, sec-butyl, tert-butyl, pentyl, isopentyl, hexyl, heptyl, octyl, nonyl-, decyl-, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl. If the number of carbon atoms is not specifically indicated the term "alkyl" represents a linear or branched alkyl radical having, as a rule, 1 to 9, particularly 1 to 6, preferably 1 to 4 carbon atoms. Particularly, the alkyl group has 1, 2, 3, 4, 5 or 6 carbon atoms ("$C_1$-$C_6$-alkyl"), e.g. methyl, ethyl, n-propyl-, isopropyl, n-butyl, tert-butyl, pentyl, isopentyl, hexyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl. Preferably, the alkyl group has 1, 2 or 3 carbon atoms ("$C_1$-$C_3$-alkyl"), methyl, ethyl, n-propyl or isopropyl.

The term "$C_2$-$C_3$-alkenyl" is to be understood as preferably meaning a linear or branched, monovalent hydrocarbon group, which contains one double bond, and which has 2 or 3 carbon atoms ("$C_2$-$C_3$-alkenyl"). Said alkenyl group is, for example, a vinyl, allyl, (E)-2-methylvinyl, (Z)-2-methylvinyl or isopropenyl group.

The term "$C_2$-$C_3$-alkynyl" is to be understood as preferably meaning a linear, monovalent hydrocarbon group which contains one triple bond, and which contains 2 or 3 carbon atoms. Said $C_2$-$C_3$-alkynyl group is, for example, ethynyl, prop-1-ynyl or prop-2-ynyl group.

The term "$C_3$-$C_7$-cycloalkyl" is to be understood as preferably meaning a saturated, monovalent, monocyclic hydrocarbon ring which contains 3, 4, 5, 6 or 7 carbon atoms. Said $C_3$-$C_7$-cycloalkyl group is for example, a monocyclic hydrocarbon ring, e.g. a cyclopropyl, cyclobutyl, cyclopentyl, cyclohexyl or cycloheptyl group. Said cycloalkyl ring can optionally contain one or more double bonds e.g. cycloalkenyl, such as a cyclopropenyl, cyclobutenyl, cyclopentenyl, cyclohexenyl or cycloheptenyl group, wherein the bond between said ring with the rest of the molecule may be to any carbon atom of said ring, be it saturated or unsaturated. Particularly, said cycloalkyl group is a $C_4$-$C_6$-cycloalkyl, a $C_5$-$C_6$-cycloalkyl or a cyclohexyl group.

The term "$C_3$-$C_5$-cycloalkyl" is to be understood as preferably meaning a saturated, monovalent, monocyclic hydrocarbon ring which contains 3, 4 or 5 carbon atoms. In particular said $C_3$-$C_5$-cycloalkyl group is a monocyclic hydrocarbon ring such as a cyclopropyl, cyclobutyl or cyclopentyl group. Preferably said "$C_3$-$C_5$-cycloalkyl" group is a cyclopropyl group.

The term "$C_3$-$C_6$-cycloalkyl" is to be understood as preferably meaning a saturated, monovalent, monocyclic hydrocarbon ring which contains 3, 4, 5 or 6 carbon atoms. In particular said $C_3$-$C_5$-cycloalkyl group is a monocyclic hydrocarbon ring such as a cyclopropyl, cyclobutyl, cyclopentyl or cyclohexyl group.

The term "$C_3$-$C_6$-cycloalkyl-$C_1$-$C_3$-alkyl-" group is to be understood as preferably meaning a $C_3$-$C_6$-cycloalkyl group as defined supra, in which one of the hydrogen atoms is replaced by a $C_1$-$C_3$-alkyl group, as defined supra, that links the $C_3$-$C_6$-cycloalkyl-$C_1$-$C_3$-alkyl- group to the molecule. Particularly, the "$C_3$-$C_6$-cycloalkyl-$C_1$-$C_3$-alkyl-" is a "$C_3$-$C_6$-cycloalkyl-$C_1$-$C_2$-alkyl-", preferably it is a "$C_3$-$C_6$-cycloalkyl-methyl-" group.

The term "heterocyclyl" is to be understood as meaning a saturated or partially unsaturated, monovalent, mono- or bicyclic hydrocarbon ring which contains 3, 4, 5, 6, 7, 8 or 9 carbon atoms and further containing 1, 2 or 3 heteroatom-containing groups selected from oxygen, sulfur, nitrogen. Particularly, the term "heterocyclyl" is to be understood as meaning a "4- to 10-membered heterocyclic ring".

The term "a 4- to 10-membered heterocyclic ring" is to be understood as meaning a saturated or partially unsaturated, monovalent, mono- or bicyclic hydrocarbon ring which contains 3, 4, 5, 6, 7, 8 or 9 carbon atoms, and further containing 1, 2 or 3 heteroatom-containing groups selected from oxygen, sulfur, nitrogen. A $C_3$-$C_9$-heterocyclyl is to be understood as meaning a heterocyclyl which contains at least 3, 4, 5, 6, 7, 8 or 9 carbon atoms and additionally at least one heteroatom as ring atoms. Accordingly in case of one heteroatom the ring is 4- to 10-membered, in case of two heteroatoms the ring is 5- to 11-membered and in case of three heteroatoms the ring is 6- to 12-membered.

Said heterocyclic ring is for example, a monocyclic heterocyclic ring such as an oxetanyl, azetidinyl, tetrahydrofuranyl, pyrrolidinyl, 1,3-dioxolanyl, imidazolidinyl, pyrazolidinyl, oxazolidinyl, isoxazolidinyl, 1,4-dioxanyl, pyrrolinyl, tetrahydropyranyl, piperidinyl, morpholinyl, 1,3-dithianyl, thiomorpholinyl, piperazinyl, or chinuclidinyl group. Optionally, said heterocyclic ring can contain one or more double bonds, e.g. 4H-pyranyl, 2H-pyranyl, 2,5-dihydro-1H-pyrrolyl, 1,3-dioxolyl, 4H-1,3,4-thiadiazinyl, 2,5-dihydrofuranyl, 2,3-dihydrofuranyl, 2,5-dihydrothienyl, 2,3-dihydrothienyl, 4,5-dihydrooxazolyl, 4,5-dihydroisoxazolyl, or 4H-1,4-thiazinyl group, or, it may be benzo fused.

Particularly a $C_3$-$C_7$-heterocyclyl is to be understood as meaning a heterocyclyl which contains at least 3, 4, 5, 6, or 7 carbon atoms and additionally at least one heteroatom as ring atoms. Accordingly in case of one heteroatom the ring is 4- to 8-membered, in case of two heteroatoms the ring is 5- to 9-membered and in case of three heteroatoms the ring is 6- to 10-membered.

Particularly a $C_3$-$C_6$-heterocyclyl is to be understood as meaning a heterocyclyl which contains at least 3, 4, 5 or 6 carbon atoms and additionally at least one heteroatom as ring atoms. Accordingly in case of one heteroatom the ring is 4- to 7-membered, in case of two heteroatoms the ring is 5- to 8-membered and in case of three heteroatoms the ring is 6- to 9-membered.

Particularly, the term "heterocyclyl" is to be understood as being a heterocyclic ring which contains 3, 4 or 5 carbon atoms, and 1, 2 or 3 of the above-mentioned heteroatom-containing groups (a "4- to 7-membered heterocyclic ring"), more particularly said ring can contain 4 or 5 carbon atoms, and 1, 2 or 3 of the above-mentioned heteroatom-containing groups (a "5- to 7-membered heterocyclic ring"), more particularly said heterocyclic ring is a "6-membered heterocyclic ring", which is to be understood as containing 4 carbon atoms and 2 of the above-mentioned heteroatom-containing groups or 5 carbon atoms and one of the above-mentioned heteroatom-containing groups, preferably 4 carbon atoms and 2 of the above-mentioned heteroatom-containing groups.

The term "heterocyclyl-$C_1$-$C_3$-alkyl-" group is to be understood as preferably meaning a heterocyclyl, preferably a 4- to 7-membered heterocyclic ring, more preferably a 5- to 7-membered heterocyclic ring, each as defined supra, in which one of the hydrogen atoms is replaced by a $C_1$-$C_3$-alkyl group, as defined supra, that links the heterocyclyl-$C_1$-$C_3$-alkyl- group to the molecule. Particularly, the "heterocyclyl-$C_1$-$C_3$-alkyl-" is a "heterocyclyl-$C_1$-$C_2$-alkyl-", preferably it is a heterocyclyl-methyl- group.

The term "$C_1$-$C_6$-alkoxy-" is to be understood as preferably meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy, sec-butoxy, pentyloxy, iso-pentyloxy, n-hexyloxy group, or an isomer thereof. Particularly, the "$C_1$-$C_6$-alkoxy-" group is a "$C_1$-$C_4$-alkoxy-", a "$C_1$-$C_3$-alkoxy-", a methoxy, ethoxy, or propoxy group, preferably a methoxy, ethoxy or propoxy group. Further preferred is a "$C_1$-$C_2$-alkoxy-" group, particularly a methoxy or ethoxy group.

The term "$C_1$-$C_3$-fluoroalkoxy-" is to be understood as preferably meaning a linear or branched, saturated, monovalent, $C_1$-$C_3$-alkoxy- group, as defined supra, in which one or more of the hydrogen atoms is replaced, identically or differently, by one or more fluoro atoms. Said $C_1$-$C_3$-fluoroalkoxy-group is, for example a 1,1-difluoromethoxy-, a 1,1,1-trifluoromethoxy-, a 2-fluoroethoxy-, a 3-fluoropropoxy-, a 2,2,2-trifluoroethoxy-, a 3,3,3-trifluoropropoxy- particularly a "$C_1$-$C_2$-fluoroalkoxy-" group.

The term "alkylamino-" is to be understood as preferably meaning an alkylamino group with one linear or branched alkyl group as defined supra. ($C_1$-$C_3$)-alkylamino- for example means a monoalkylamino group with 1, 2 oder 3 carbon atoms, ($C_1$-$C_6$)-alkylamino- with 1, 2, 3, 4, 5 or 6 carbon atoms. The term "alkylamino-" comprises for example methylamino-, ethylamino-, n-propylamino-, iso-propylamino-, tert.-butylamino-, n-pentylamino- or n-hexylamino-.

The term "dialkylamino-" is to be understood as preferably meaning an alkylamino group having two linear or branched alkyl groups as defined supra, which are independent from each other. ($C_1$-$C_3$)-dialkylamino- for example represents a dialkylamino group with two alkyl groups each of them having 1 to 3 carbon atoms per alkyl group. The term "dialkylamino-" comprises for example: N,N-Dimethylamino-, N,N-Diethylamino-, N-Ethyl-N-methylamino-, N-Methyl-N-n-propylamino-, N-Isopropyl-N-n-propylamino-, N-t-Butyl-N-methylamino-, N-Ethyl-N-n-pentylamino- and N-n-Hexyl-N-methylamino-.

The term "cyclic amine" is to be understood as preferably meaning a cyclic amine group. Suitable cyclic amines are especially azetidine, pyrrolidine, piperidine, piperazine, 1-methylpiperazine, morpholine, thiomorpholine, which could be optionally substituted by one or two methyl groups.

The term "halo-$C_1$-$C_3$-alkyl-" is to be understood as preferably meaning a linear or branched, saturated, monovalent hydrocarbon group in which the term "$C_1$-$C_3$-alkyl" is defined supra, and in which one or more hydrogen atoms is replaced by a halogen atom, identically or differently, i.e. one halogen atom being independent from another. Particularly, said halogen atom is fluorine. Preferred halo-$C_1$-$C_3$-alkyl-group is a fluoro-$C_1$-$C_3$-alkyl- group, such as for example —$CF_3$, —$CHF_2$, —$CH_2F$, —$CF_2CF_3$, or —$CH_2CF_3$, preferably it is —$CF_3$.

The term "phenyl-$C_1$-$C_3$-alkyl-" is to be understood as preferably meaning a phenyl group, in which one of the hydrogen atoms is replaced by a $C_1$-$C_3$-alkyl group, as defined supra, that links the phenyl-$C_1$-$C_3$-alkyl- group to the molecule. Particularly, the "phenyl-$C_1$-$C_3$-alkyl-" is a phenyl-$C_1$-$C_2$-alkyl-, preferably it is a benzyl- group.

The term "heteroaryl" is to be understood as preferably meaning a monovalent, aromatic ring system having 5, 6, 7, 8, 9, 10, 11, 12, 13 or 14 ring atoms (a "5- to 14-membered heteroaryl" group), particularly 5 (a "5-membered heteroaryl") or 6 (a "6-membered heteroaryl") or 9 (a "9-membered heteroaryl") or 10 ring atoms (a "10-membered heteroaryl"), and which contains at least one heteroatom which may be identical or different, said heteroatom being such as oxygen, nitrogen or sulfur, and can be monocyclic, bicyclic, or tricyclic, and in addition in each case can be benzo-condensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, tetrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, or oxepinyl, etc. Preferably, heteroaryl is selected from monocyclic heteroaryl, 5-membered heteroaryl or 6-membered heteroaryl.

The term "5-membered heteroaryl" is understood as preferably meaning a monovalent, aromatic ring system having 5 ring atoms and which contains at least one heteroatom which may be identical or different, said heteroatom being such as oxygen, nitrogen or sulfur. Particularly, "5-membered heteroaryl" is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, tetrazolyl.

The term "6-membered heteroaryl" is understood as preferably meaning a monovalent, aromatic ring system having 6 ring atoms and which contains at least one heteroatom which may be identical or different, said heteroatom being such as oxygen, nitrogen or sulfur. Particularly, "6-membered heteroaryl" is selected from pyridyl, pyridazinyl, pyrimidinyl, pyrazinyl, triazinyl.

The term "heteroaryl-$C_1$-$C_3$-alkyl-" is to be understood as preferably meaning a heteroaryl, a 5-membered heteroaryl or a 6-membered heteroaryl group, each as defined supra, in which one of the hydrogen atoms is replaced by a $C_1$-$C_3$-alkyl group, as defined supra, that links the heteroaryl-$C_1$-$C_3$-alkyl- group to the molecule. Particularly, the "heteroaryl-$C_1$-$C_3$-alkyl-" is a heteroaryl-$C_1$-$C_2$-alkyl-, a pyridinyl-$C_1$-$C_3$-alkyl-, a pyridinylmethyl-, a pyridinylethyl-, a pyridinylpropyl-, a pyrimidinyl-$C_1$-$C_3$-alkyl-, a pyrimidinylmethyl-, a pyrimidinylethyl-, a pyrimidinylpropyl-, preferably a pyridinylmethyl- or a pyridinylethyl- or a pyrimidinylethyl- or a pyrimidinylpropyl- group.

The term "$C_1$-$C_{10}$", as used throughout this text, e.g. in the context of the definition of "$C_1$-$C_{10}$-alkyl" is to be understood as meaning an alkyl group having a finite number of carbon atoms of 1 to 10, i.e. 1, 2, 3, 4, 5, 6, 7, 8, 9 or 10 carbon atoms. It is to be understood further that said term "$C_1$-$C_{10}$" is to be interpreted as any sub-range comprised therein, e.g. $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$, $C_2$-$C_{10}$, $C_2$-$C_9$, $C_2$-$C_8$, $C_2$-$C_7$, $C_2$-$C_6$, $C_2$-$C_5$, $C_2$-$C_4$, $C_2$-$C_3$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$, $C_9$-$C_{10}$.

Similarly, as used herein, the term "$C_1$-$C_6$", as used throughout this text, e.g. in the context of the definition of "$C_1$-$C_6$-alkyl", "$C_1$-$C_6$-alkoxy" is to be understood as meaning an alkyl group having a finite number of carbon atoms of 1 to 6, i.e. 1, 2, 3, 4, 5 or 6 carbon atoms. It is to be understood further that said term "$C_1$-$C_6$" is to be interpreted as any sub-range comprised therein, e.g. $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, $C_5$-$C_6$.

Similarly, as used herein, the term "$C_1$-$C_3$", as used throughout this text, e.g. in the context of the definition of "$C_1$-$C_3$-alkyl", "$C_1$-$C_3$-alkoxy" or "$C_1$-$C_3$-fluoroalkoxy" is to be understood as meaning an alkyl group having a finite number of carbon atoms of 1 to 3, i.e. 1, 2 or 3 carbon atoms. It is to be understood further that said term "$C_1$-$C_3$" is to be interpreted as any sub-range comprised therein, e.g. $C_1$-$C_3$, $C_1$-$C_2$, $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_3$-$C_5$, $C_3$-$C_4$, $C_4$-$C_6$, $C_4$-$C_5$, $C_5$-$C_6$.

Further, as used herein, the term "$C_3$-$C_7$", as used throughout this text, e.g. in the context of the definition of "$C_3$-$C_7$-cycloalkyl", is to be understood as meaning a cycloalkyl group having a finite number of carbon atoms of 3 to 7, i.e. 3, 4, 5, 6 or 7 carbon atoms, particularly 3, 4, 5 or 6 carbon atoms. It is to be understood further that said term "$C_3$-$C_7$" is to be interpreted as any sub-range comprised therein, e.g. $C_3$-$C_7$, $C_3$-$C_6$, $C_3$-$C_5$, $C_3$-$C_4$, $C_4$-$C_7$, $C_4$-$C_6$, $C_4$-$C_5$, $C_5$-$C_7$, $C_5$-$C_6$, $C_6$-$C_7$.

A symbol ⌇ at a bond denotes the linkage site in the molecule.

As used herein, the term "one or more times", e.g. in the definition of the substituents of the compounds of the general formulae of the present invention, is understood as meaning one, two, three, four or five times, particularly one, two, three or four times, more particularly one, two or three times, even more particularly one or two times.

Where the plural form of the word compounds, salts, hydrates, solvates and the like, is used herein, this is taken to mean also a single compound, salt, isomer, hydrate, solvate or the like.

In another embodiment the present invention concerns compounds of general formula (I), wherein

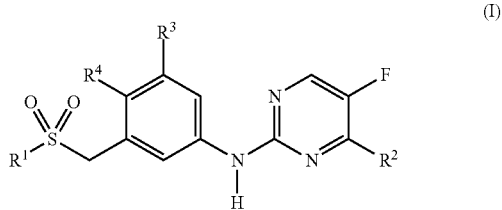

(I)

wherein $R^1$ represents a group selected from $C_1$-$C_6$-alkyl-, $C_3$-$C_7$-cycloalkyl or phenyl-$C_1$-$C_3$-alkyl-, wherein said group is optionally substituted with one or two or three substituents, identically or differently, selected from the group of hydroxy or $C_1$-$C_6$-alkoxy, $R^2$ represents a group selected from

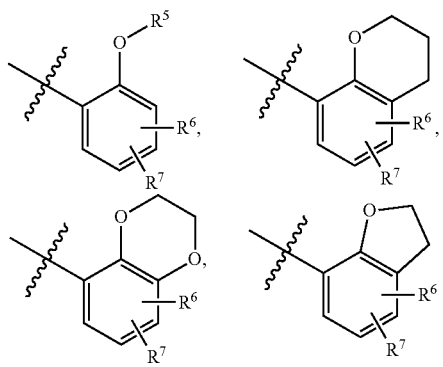

$R^3$, $R^4$ represent, independently from each other, a group selected from a hydrogen or fluoro atom;

$R^5$ represents a group selected from
  a) a $C_1$-$C_6$-alkyl group, which is optionally substituted with one or two or three substituents, identically or differently, selected from halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, heterocyclyl-, phenyl, heteroaryl, wherein said $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;
  b) a phenyl-$C_1$-$C_3$-alkyl-group, which phenyl group is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

c) a heteroaryl-$C_1$-$C_3$-alkyl- group, which heteroaryl group is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;

or their salts, solvates or salts of solvates.

In another embodiment the present invention concerns compounds of general formula (I), wherein $R^1$ represents a group selected from $C_1$-$C_6$-alkyl-, $C_3$-$C_5$-cycloalkyl-, wherein said group is optionally substituted with one or two substituents, identically or differently, selected from the group of hydroxy, $C_1$-$C_2$-alkoxy-, halo-$C_1$-$C_2$-alkyl-, $C_1$-$C_2$-fluoroalkoxy-;

$R^2$ represents a group selected from

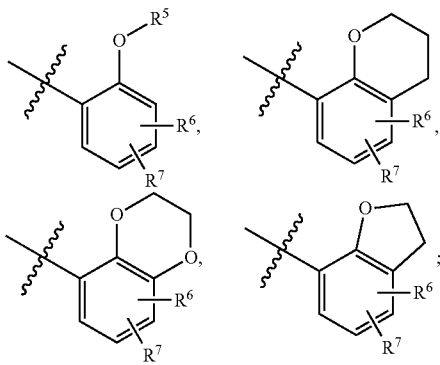

$R^3$ represents a hydrogen atom or a fluoro atom;
$R^4$ represents a hydrogen atom or a fluoro atom;
$R^5$ represents a group selected from
a) a $C_1$-$C_6$-alkyl group, which is optionally substituted with one or two or three substituents, identically or differently, selected from halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_3$-$C_7$-cycloalkyl-, heterocyclyl-, phenyl, heteroaryl, wherein said $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, dialkylamino-, acetylamino-, N-methyl-N-acetylamino-, cyclic amines, halo-$C_1$-$C_3$-alkyl-, $C_1$-$C_3$-fluoroalkoxy-;
b) a phenyl-$C_1$-$C_3$-alkyl- group, which phenyl group is optionally substituted with one or two or three substituents, identically or differently, selected from the group of halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
c) a heteroaryl-$C_1$-$C_3$-alkyl- group, which heteroaryl group is optionally substituted with one or two or three substituents, identically or differently, selected from the group of halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
d) a $C_3$-$C_6$-cycloalkyl-$C_1$-$C_3$-alkyl- group, which $C_3$-$C_6$-cycloalkyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;
e) a heterocyclyl-$C_1$-$C_3$-alkyl- group, which heterocyclyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;
f) phenyl-cyclopropyl- group, which phenyl group is optionally substituted with one or two or three substituents, identically or differently, selected from the group of halogen, hydroxy, —$NH_2$, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
g) a heteroaryl-cyclopropyl- group, which heteroaryl group is optionally substituted with one or two or three substituents, identically or differently, selected from the group of halogen, hydroxy, —$NH_2$, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;

or their salts, solvates or salts of solvates.

In another embodiment the present invention concerns compounds of general formula (I), wherein $R^1$ represents a group selected from $C_1$-$C_4$-alkyl-, $C_3$-$C_6$-cycloalkyl or phenyl-$C_1$-$C_2$-alkyl-, wherein said group is optionally substituted with one or two or three substituents, identically or differently, selected from the group of hydroxy or $C_1$-$C_3$-alkoxy, $R^2$ represents a group selected from

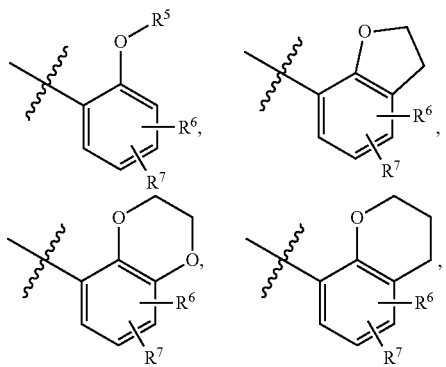

$R^3$, $R^4$ represent, independently from each other a group selected from a hydrogen or fluoro atom,
$R^5$ represents a group selected from
a) a $C_1$-$C_3$-alkyl group, which is optionally substituted with one or two or three substituents, identically or differently, selected from halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, heterocyclyl-, phenyl, heteroaryl, wherein said $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

b) a phenyl-$C_1$-$C_3$-alkyl- group, which phenyl group is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

c) a heteroaryl-$C_1$-$C_3$-alkyl- group, which heteroaryl group is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

$R^6$, $R^7$ represent, independently from each other, a group selected from a hydrogen or fluoro atom or $C_1$-$C_3$-alkoxy-, or their salts, solvates or salts of solvates.

In another embodiment the present invention concerns compounds of general formula (I), wherein $R^1$ represents a group selected from $C_1$-$C_6$-alkyl-, $C_3$-$C_5$-cycloalkyl-, wherein said group is optionally substituted with one or two substituents, identically or differently, selected from the group of hydroxy, $C_1$-$C_6$-alkoxy-;

$R^2$ represents a group selected from

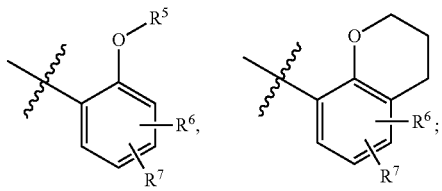

$R^3$ represents a hydrogen atom or fluoro atom;
$R^4$ represents a hydrogen atom or a fluoro atom;
$R^5$ represents a group selected from a) a $C_1$-$C_3$-alkyl group, which is optionally substituted with one or two or three substituents, identically or differently, selected from halogen, cyano, halo-$C_1$-$C_3$-alkyl-;

b) a phenyl-$C_1$-$C_3$-alkyl- group, which phenyl group is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-;

c) a heteroaryl-$C_1$-$C_3$-alkyl- group, which heteroaryl group is optionally substituted with one or two substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-;

d) a $C_3$-$C_6$-cycloalkyl-$C_1$-$C_3$-alkyl- group, which $C_3$-$C_6$-cycloalkyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;

e) a heterocyclyl-$C_1$-$C_3$-alkyl- group, which heterocyclyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;

f) phenyl-cyclopropyl- group, which phenyl group is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-;

g) a heteroaryl-cyclopropyl- group, which heteroaryl group is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-;

$R^6$, $R^7$ represent, independently from each other, a group selected from a hydrogen atom or a fluoro atom;

or their salts, solvates or salts of solvates.

In a preferred embodiment the present invention concerns compounds of general formula (I), wherein $R^1$ represents a group selected from $C_1$-$C_6$-alkyl-, $C_3$-$C_5$-cycloalkyl-, wherein said group is optionally substituted with one or two substituents, identically or differently, selected from the group of hydroxy, $C_1$-$C_6$-alkoxy-;

$R^2$ represents a group selected from

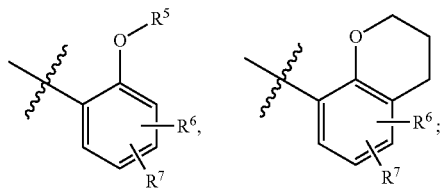

$R^3$ represents a hydrogen atom or fluoro atom;
$R^4$ represents a hydrogen atom;
$R^5$ represents a group selected from
a) a $C_1$-$C_3$-alkyl group;
b) a phenyl-$C_1$-$C_3$-alkyl- group;

$R^6$, $R^7$ represent, independently from each other, a group selected from a hydrogen atom or fluoro atom;

or their salts, solvates or salts of solvates.

In another preferred embodiment the present invention concerns compounds of general formula (I), $R^1$ represents a group selected from $C_1$-$C_3$-alkyl-, $C_3$-$C_5$-cycloalkyl- or phenyl-$C_1$-$C_2$-alkyl-, wherein said group is optionally substituted with one or two or three substituents, identically or differently, selected from the group of hydroxy or methoxy, $R^2$ represents a group selected from

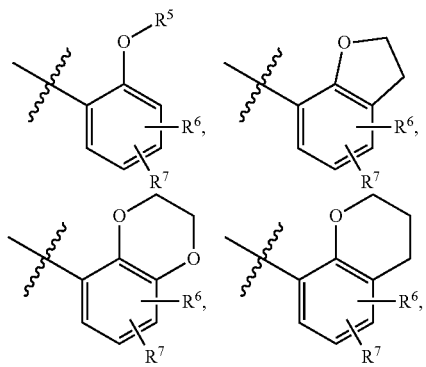

$R^3$ represents a hydrogen or fluoro atom,
$R^4$ represents a hydrogen atom, $R^5$ represents a group selected from
a) a $C_1$-$C_3$-alkyl group,
b) a phenyl-$C_1$-$C_3$-alkyl- group, which phenyl group is optionally substituted with one or two or three substituents, identically or differently, selected from the group of halogen or $C_1$-$C_3$-alkoxy-;
c) a pyridyl-$C_1$-$C_3$-alkyl- group, which heteroaryl group is optionally substituted with one or two or three substituents, identically or differently, selected from the group of halogen or $C_1$-$C_3$-alkoxy-;

$R^6$, $R^7$ represent, independently from each other, a group selected from a hydrogen or fluoro atom,
or their salts, solvates or salts of solvates.

In another preferred embodiment the present invention concerns compounds of general formula (I), wherein $R^1$ represents a group selected from methyl, ethyl, propan-2yl-, cyclopropyl, tert-butyl-, cyclohexyl, wherein said group is optionally substituted with one substituent selected from the group of hydroxy, methoxy-; $C_1$-$C_6$-alkoxy-;

$R^2$ represents a group selected from

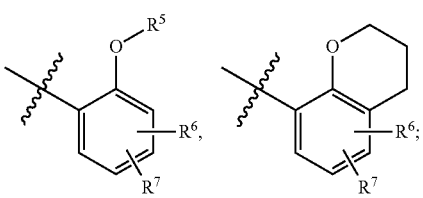

$R^3$ represents a hydrogen atom or fluoro atom;
$R^4$ represents a hydrogen atom;
$R^5$ represents a group selected from methyl and benzyl;
$R^6$, $R^7$ represent, independently from each other, a group selected from a hydrogen atom or fluoro atom;
or their salts, solvates or salts of solvates.

In another embodiment the present invention concerns compounds of general formula (I), wherein $R^1$ represents a group selected from methyl, ethyl, propan-2yl-, cyclopropyl, tert-butyl-, cyclohexyl, wherein said group is optionally substituted with one substituent selected from the group of hydroxy, methoxy-; $C_1$-$C_6$-alkoxy-;

$R^2$ represents a group selected from 4-fluoro-2-methoxyphenyl-, 2-(benzyloxy)-4-fluorophenyl-, 3,4-dihydro-2H-chromen-8-yl-;

$R^3$ represents a hydrogen atom or fluoro atom;
$R^4$ represents a hydrogen atom;
or their salts, solvates or salts of solvates.

In another embodiment the present invention concerns compounds of general formula (I), wherein $R^1$ represents a methyl group;

$R^2$ represents a group selected from 4-fluoro-2-methoxyphenyl-, 2-(benzyloxy)-4-fluorophenyl-, 3,4-dihydro-2H-chromen-8-yl-;

$R^3$ represents a hydrogen atom or fluoro atom;
$R^4$ represents a hydrogen atom;
or their salts, solvates or salts of solvates.

In another embodiment the invention relates to compounds of formula (I), in which $R^1$ represents a $C_1$-$C_6$-alkyl-, a $C_3$-$C_7$-cycloalkyl-, a heterocyclyl-, a phenyl, a heteroraryl, a phenyl-$C_1$-$C_3$-alkyl- or a heteroaryl-$C_1$-$C_3$-alkyl- group, wherein said group is optionally substituted with one or two or three substituents, identically or differently, selected from the group of hydroxy, cyano, halogen, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amines.

In another embodiment the invention relates to compounds of formula (I), in which $R^1$ represents a $C_1$-$C_3$-alkyl-, a $C_3$-$C_5$-cycloalkyl-, a 4- to 7-membered heterocyclic ring, a phenyl, a heteroraryl, a phenyl-$C_1$-$C_2$-alkyl- or a heteroaryl-$C_1$-$C_2$-alkyl- group, wherein said group is optionally substituted with one or two or three substituents, identically or differently, selected from the group of hydroxy, cyano, halogen, halo-$C_1$-$C_2$-alkyl-, $C_1$-$C_3$-alkoxy-, $C_1$-$C_2$-fluoroalkoxy-, —$NH_2$, alkylamino-, dialkylamino-, acetylamino-, N-methyl-N-acetylamino-, cyclic amines.

In another embodiment the invention relates to compounds of formula (I), in which $R^1$ represents a phenyl or a heteroraryl group, wherein said group is optionally substituted with one or two or three substituents, identically or differently, selected from the group of hydroxy, cyano, halogen, halo-$C_1$-$C_2$-alkyl-, $C_1$-$C_3$-alkoxy-, $C_1$-$C_2$-fluoroalkoxy-, —$NH_2$, alkylamino-, dialkylamino-, acetylamino-, N-methyl-N-acetylamino-, cyclic amines.

In another embodiment the invention relates to compounds of formula (I), in which $R^1$ represents a group selected from methyl, ethyl, propan-2-yl, cyclopropyl, tert-butyl, cyclopentyl, cyclohexyl or phenyl;

wherein said group is optionally substituted with one substituent selected from the group of hydroxyl or methoxy.

In another embodiment the invention relates to compounds of formula (I), in which $R^1$ represents a group selected from methyl, ethyl, propan-2-yl, tert butyl, cyclopropyl, cyclohexyl or phenyl;

wherein said group is optionally substituted with one substituent selected from the group of hydroxyl or methoxy.

In another embodiment the invention relates to compounds of formula (I), in which $R^1$ represents a group selected from $C_1$-$C_6$-alkyl-, $C_3$-$C_7$-cycloalkyl or phenyl-$C_1$-$C_3$-alkyl-, wherein said group is optionally substituted with one or two or three substituents, identically or differently, selected from the group of hydroxy or $C_1$-$C_6$-alkoxy.

In another embodiment the invention relates to compounds of formula (I), in which $R^1$ represents a group selected from $C_1$-$C_4$-alkyl-, $C_3$-$C_6$-cycloalkyl or phenyl-$C_1$-$C_2$-alkyl-, wherein said group is optionally substituted with one or two or three substituents, identically or differently, selected from the group of hydroxy or $C_1$-$C_3$-alkoxy.

In a preferred embodiment the invention relates to compounds of formula (I), in which $R^1$ represents a group selected from methyl or cyclopropyl.

In another preferred embodiment the invention relates to compounds of formula (I), in which $R^1$ represents a cyclopropyl group.

In another preferred embodiment the invention relates to compounds of formula (I), in which $R^1$ represents a methyl group.

In another embodiment the invention relates to compounds of formula (I), in which R² represents a group selected from

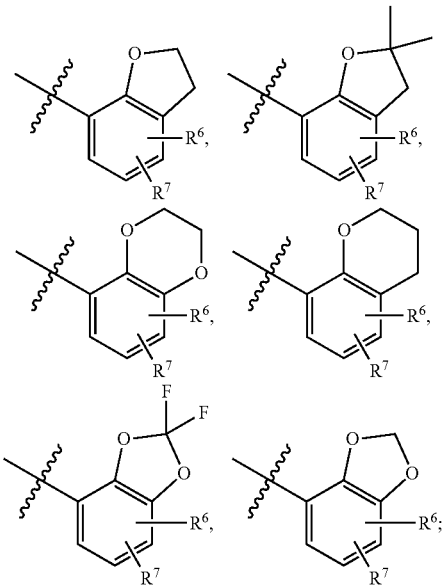

In another embodiment the invention relates to compounds of formula (I), in which R² represents a group selected from

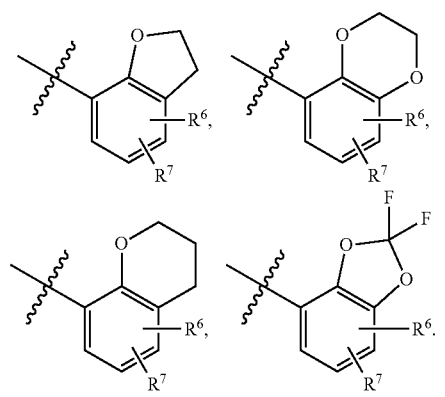

In another embodiment the invention relates to compounds of formula (I), in which R² represents a group selected from

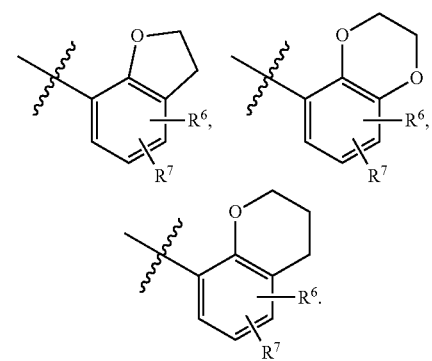

In another embodiment the invention relates to compounds of formula (I), in which R² represents a group selected from

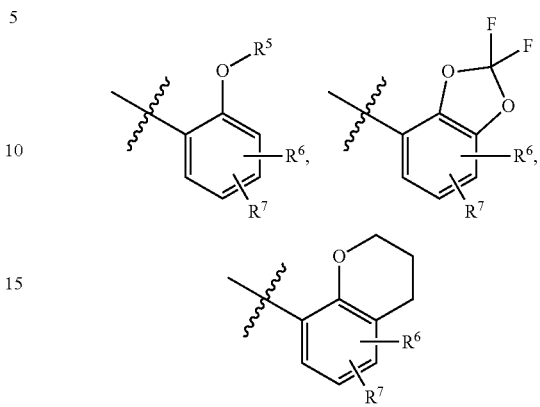

In another embodiment the invention relates to compounds of formula (I), in which R² represents a group selected from

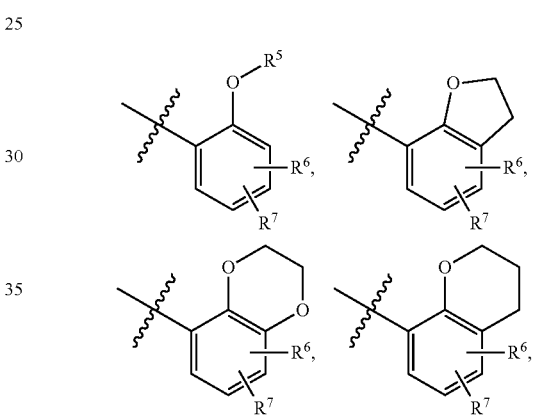

In another embodiment the invention relates to compounds of formula (I), in which R² represents a group selected from

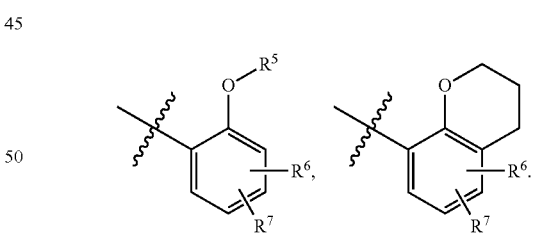

In another embodiment the invention relates to compounds of formula (I), in which R² represents a group selected from

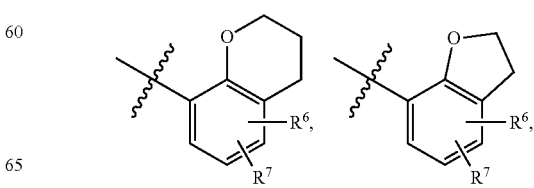

-continued

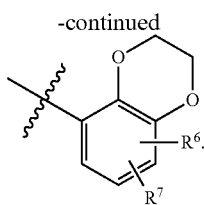

In a preferred embodiment the invention relates to compounds of formula (I), in which $R^2$ represents

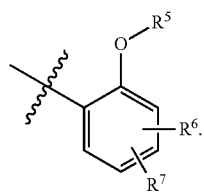

In another embodiment the invention relates to compounds of formula (I), in which $R^2$ represents a group selected from 4,5-difluoro-2-methoxyphenyl-; 3,4-difluoro-2-methoxyphenyl-, 4-fluoro-2-methoxyphenyl-, 2-(benzyloxy)-4-fluorophenyl-, 5-fluoro-2-methoxyphenyl-, 2-[(4-fluorobenzyl)oxy]phenyl-, 2-[(3-fluorobenzyl)oxy]phenyl-, 2-[(2-chlorobenzyl)oxy]phenyl-, 2-[(3-chlorobenzyl)oxy]phenyl-, 5-fluoro-2-[(2-fluorobenzyl)oxy]phenyl-, 5-fluoro-2-[(3-fluorobenzyl)oxy]phenyl-, 4-chloro-2-methoxyphenyl-, 3,4-dihydro-2H-chromen-8-yl-.

In another embodiment the invention relates to compounds of formula (I), in which $R^2$ represents a group selected from 4,5-difluoro-2-methoxyphenyl-; 4-fluoro-2-methoxyphenyl-, 2-(benzyloxy)-4-fluorophenyl-, 2-[(4-fluorobenzyl)oxy]phenyl-, 2-[(3-fluorobenzyl)oxy]phenyl-, 2-[(3-chlorobenzyl)oxy]phenyl-, 5-fluoro-2-[(3-fluorobenzyl)oxy]phenyl-, 3,4-dihydro-2H-chromen-8-yl-.

In another embodiment the invention relates to compounds of formula (I), in which $R^2$ represents a group selected from 4,5-difluoro-2-methoxyphenyl-; 4-fluoro-2-methoxyphenyl-, 2-(benzyloxy)-4-fluorophenyl-, 2-[(4-fluorobenzyl)oxy]phenyl-, 2-[(3-fluorobenzyl)oxy]phenyl-, 5-fluoro-2-[(3-fluorobenzyl)oxy]phenyl-, 3,4-dihydro-2H-chromen-8-yl-.

In another embodiment the invention relates to compounds of formula (I), in which $R^2$ represents a group selected from 4-fluoro-2-methoxyphenyl-, 2-(benzyloxy)-4-fluorophenyl-, 2-[(3-fluorobenzyl)oxy]phenyl-, 5-fluoro-2-[(3-fluorobenzyl)oxy]phenyl-, 3,4-dihydro-2H-chromen-8-yl-.

In another embodiment the invention relates to compounds of formula (I), in which $R^2$ represents a group selected from 4-fluoro-2-methoxyphenyl-, 2-(benzyloxy)-4-fluorophenyl-, 3,4-dihydro-2H-chromen-8-yl-.

In another embodiment the invention relates to compounds of formula (I), in which $R^2$ represents a group selected from 4-fluoro-2-methoxyphenyl- or 2-(benzyloxy)-4-fluorophenyl-.

In a preferred embodiment the invention relates to compounds of formula (I), in which $R^2$ represents a 4-fluoro-2-methoxyphenyl- group.

In another embodiment the invention relates to compounds of formula (I), in which $R^3$ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^3$ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I), in which $R^3$ represents a group selected from a hydrogen, a fluoro or a chloro atom.

In another embodiment the invention relates to compounds of formula (I), in which $R^3$ and $R^4$ represent independently from each other a group selected from a hydrogen or fluoro atom.

In another embodiment the invention relates to compounds of formula (I), in which $R^3$ represents a hydrogen or fluoro atom and $R^4$ represents a hydrogen atom.

In another embodiment the invention relates to compounds of formula (I), in which $R^3$ represents a fluoro or a chloro atom.

In another embodiment the invention relates to compounds of formula (I), in which $R^3$ represents a group selected from a hydrogen atom or a fluoro atom.

In another embodiment the invention relates to compounds of formula (I), in which $R^3$ represents a hydrogen atom.

In a preferred embodiment the invention relates to compounds of formula (I), in which $R^3$ represents a fluoro atom.

In another embodiment the invention relates to compounds of formula (I), in which $R^4$ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^4$ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I), in which $R^4$ represents a group selected from a hydrogen, a fluoro or a chloro atom.

In another embodiment the invention relates to compounds of formula (I), in which $R^4$ represents a fluoro or a chloro atom.

In another embodiment the invention relates to compounds of formula (I), in which $R^4$ represents a group selected from a hydrogen atom or fluoro atom.

In another embodiment the invention relates to compounds of formula (I), in which $R^4$ represents a hydrogen atom.

In a preferred embodiment the invention relates to compounds of formula (I), in which $R^4$ represents a fluoro atom.

In another embodiment the invention relates to compounds of formula (I), in which $R^5$ represents a $C_1$-$C_6$-alkyl group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, $C_3$-$C_7$-heterocyclyl-, phenyl, heteroaryl,
  wherein said $C_3$-$C_7$-cycloalkyl-, $C_3$-$C_7$-heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^5$ represents a $C_1$-$C_3$-alkyl group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_2$-alkyl-, $C_1$-$C_2$-fluoroalkoxy-, $C_1$-$C_2$-alkoxy-, $C_2$-$C_3$-alkenyl-, $C_2$-$C_3$-alkynyl-, $C_4$-$C_6$-cycloalkyl-, $C_3$-$C_7$-heterocyclyl-, phenyl, heteroaryl,
  wherein said $C_4$-$C_6$-cycloalkyl-, $C_3$-$C_7$-heterocyclyl-, phenyl or heteroaryl group is optionally substituted with one, two or three substituents, identically or differently, selected from halogen, hydroxy, $C_1$-$C_2$-alkyl-, $C_1$-$C_2$-alkoxy-, —$NH_2$, alkylamino-, dialkylamino-, acetylamino-, N-methyl-N-acetylamino-, cyclic amines, halo-$C_1$-$C_2$-alkyl-, $C_1$-$C_2$-fluoroalkoxy-.

In another embodiment the invention relates to compounds of formula (I), in which $R^5$ represents a $C_1$-$C_6$-alkyl group, which is optionally substituted with one or two or three substituents, identically or differently, selected from halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, heterocyclyl-, phenyl, heteroaryl,
  wherein said $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^5$ represents a $C_1$-$C_3$-alkyl group, which is optionally substituted with one or two or three substituents, identically or differently, selected from halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, heterocyclyl-, phenyl, heteroaryl,
  wherein said $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^5$ represents a $C_1$-$C_3$-alkyl group.

In another embodiment the invention relates to compounds of formula (I), in which $R^5$ represents a $C_1$-$C_6$-alkyl- group, which is optionally substituted with one or two or three substituents, identically or differently, selected from the group of halogen atom, $C_1$-$C_3$-alkyl-, $C_3$-$C_6$-cycloalkyl-, $C_3$-$C_6$-heterocyclyl-, phenyl, heteroaryl, wherein said $C_3$-$C_6$-cycloalkyl-, $C_3$-$C_6$-heterocyclyl-, phenyl- or heteroaryl group is optionally substituted with one substituent selected from halogen.

In another embodiment the invention relates to compounds of formula (I), in which $R^5$ represents a $C_1$-$C_3$-alkyl group, which is optionally substituted with one or two or three substituents, identically or differently, selected from halogen, cyano, halo-$C_1$-$C_3$-alkyl-.

In another embodiment the invention relates to compounds of formula (I), in which $R^5$ represents a $C_1$-$C_3$-alkyl- group, which is substituted with one or two or three substituents, identically or differently, selected from the group of a halogen atom.

In another embodiment the invention relates to compounds of formula (I), in which $R^5$ represents a $C_1$-$C_3$-alkyl- group, which is substituted with one or two or three substituents, identically or differently, selected from the group of a chloro or fluoro atom.

In another embodiment the invention relates to compounds of formula (I), in which $R^5$ represents a $C_1$-$C_3$-alkyl- group, which is substituted with one or two or three substituents selected from the group of a fluoro atom.

In another embodiment the invention relates to compounds of formula (I), in which $R^5$ represents a group selected from —$CH_2CH_2CF_3$, —$CH_2CH_2CF_2CF_3$.

In another embodiment the invention relates to compounds of formula (I), in which $R^5$ represents a group selected from methyl, ($^2H_3$)methyl.

In another embodiment the invention relates to compounds of formula (I), in which $R^5$ represents a methyl group.

In another embodiment the invention relates to compounds of formula (I), in which $R^5$ represents a $C_5$-$C_6$-cycloalkyl- group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-.

In another embodiment the invention relates to compounds of formula (I), in which $R^5$ represents a $C_5$-$C_6$-cycloalkyl- group, which is optionally substituted with one or two or three substituents, identically or differently, selected from the group of fluoro, chloro, hydroxy, —$NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-, $C_2$-$C_3$-alkenyl-, $C_2$-$C_3$-alkynyl-.

In another embodiment the invention relates to compounds of formula (I), in which $R^5$ represents a cyclopentyl or cyclohexyl group, which is optionally substituted with one or two or three substituents, identically or differently, selected from the group of fluoro, chloro, hydroxy, —$NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-, $C_2$-$C_3$-alkenyl-, $C_2$-$C_3$-alkynyl-.

In another embodiment the invention relates to compounds of formula (I), in which $R^5$ represents a cyclohexyl or cyclopentyl group.

In another embodiment the invention relates to compounds of formula (I), in which $R^5$ represents a $C_3$-$C_6$-cycloalkyl-$C_1$-$C_3$-alkyl- group, which $C_3$-$C_6$-cycloalkyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^5$ represents a $C_3$-$C_6$-cycloalkyl-$CH_2$— group, which $C_3$-$C_6$-cycloalkyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-.

In a preferred embodiment the invention relates to compounds of formula (I), in which $R^5$ represents a cyclohexyl-$CH_2$— or cyclopentyl-$CH_2$— group, which cyclohexyl or cyclopentyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^5$ represents a heterocyclyl-$C_1$-$C_3$-alkyl- group, which heterocyclyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^5$ represents a heterocyclyl-$CH_2$— group, which heterocyclyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^5$ represents a 4- to 7-membered heterocyclic ring, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-.

In another embodiment the invention relates to compounds of formula (I), in which $R^5$ represents a 4- to 7-membered heterocyclic ring, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-, $C_2$-$C_3$-alkenyl-, $C_2$-$C_3$-alkynyl-.

In another embodiment the invention relates to compounds of formula (I), in which $R^5$ represents a phenyl group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^5$ represents a phenyl group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I), in which $R^5$ represents a heteroaryl group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^5$ represents a heteroaryl group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I), in which $R^5$ represents a phenyl-$C_1$-$C_3$-alkyl- group, which phenyl group is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-; —$C_1$-$C_3$-alkyl-, $C_1$-$C_3$-fluoroalkoxy-, $C_1$-$C_3$-alkoxy-.

In another embodiment the invention relates to compounds of formula (I), in which $R^5$ represents a phenyl-$C_1$-$C_3$-alkyl- group, which phenyl group is optionally substituted with one or two or three substituents, identically or differently, selected from the group of halogen or $C_1$-$C_3$-alkoxy-.

In another embodiment the invention relates to compounds of formula (I), in which $R^5$ represents a phenyl-$C_1$-$C_3$-alkyl- group, which phenyl group is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^5$ represents a phenyl-$C_1$-$C_2$-alkyl- group, which phenyl group is optionally substituted with one or two or three substituents, identically or differently, selected from the group of halogen, hydroxy, $NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^5$ represents a phenyl-$C_1$-$C_2$-alkyl- group, which phenyl group is optionally substituted with one or two or three substituents, identically or differently, selected from the group of halogen, hydroxy, $NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I), in which $R^5$ represents a benzyl group, which phenyl group is optionally substituted with one or two or three substituents, identically or differently, selected from the group of halogen, hydroxy, $NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I), in which $R^5$ represents a benzyl group, which phenyl group is optionally substituted with one or two or three substituents, identically or differently, selected from the group of a fluoro atom, a methyl group In another embodiment the invention relates to compounds of formula (I), in which $R^5$ represents a benzyl group, which phenyl group is optionally substituted with one or two substituents, identically or differently, selected from the group of a fluoro or a chloro atom.

In another embodiment the invention relates to compounds of formula (I), in which $R^5$ represents a benzyl group, which phenyl group is optionally substituted with one fluoro atom.

In another embodiment the invention relates to compounds of formula (I), in which $R^5$ represents a benzyl, a 4-fluorobenzyl-, a 4-chlorobenzyl, a 3-fluorobenzyl or a 3-chlorobenzyl group.

In another embodiment the invention relates to compounds of formula (I), in which $R^5$ represents a phenyl-cyclopropyl- group, which phenyl group is optionally substituted with one or two or three substituents, identically or differently, selected from the group of halogen, hydroxy, $NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^5$ represents a phenyl-cyclopropyl- group, which phenyl group is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^5$ represents a phenyl-cyclopropyl- group, which phenyl group is optionally substituted with one or two or three substituents, identically or differently, selected from the group of a fluoro atom, a methyl group.

In another embodiment the invention relates to compounds of formula (I), in which $R^5$ represents a heteroaryl-$C_1$-$C_3$-alkyl- group, which heteroaryl group is optionally substituted with one or two substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^5$ represents a heteroaryl-$C_1$-$C_2$-alkyl- group, which heteroaryl group is optionally substituted with one or two or three substituents, identically or differently, selected from the group of halogen, hydroxy, $NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^5$ represents a heteroaryl-$C_1$-$C_3$-alkyl- group, which heteroaryl group is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy.

In another embodiment the invention relates to compounds of formula (I), in which $R^5$ represents a pyridyl-$C_1$-$C_3$-alkyl- group, which heteroaryl group is optionally substituted with one or two or three substituents, identically or differently, selected from the group of halogen or $C_1$-$C_3$-alkoxy-.

In another embodiment the invention relates to compounds of formula (I), in which $R^5$ represents a heteroaryl-$C_1$-$C_2$-alkyl- group, which heteroaryl group is optionally substituted with one or two or three substituents, identically or differently, selected from the group of halogen, hydroxy, $NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I), in which $R^5$ represents a pyridyl-$C_1$-$C_2$-alkyl- group, which pyridyl group is optionally substituted with one or two or three substituents, identically or differently, selected from the group of halogen, hydroxy, $NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I), in which $R^5$ represents a pyridyl-$CH_2$— group, which pyridyl group is optionally substituted with one or two or three substituents, identically or differently, selected from the group of halogen, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I), in which $R^5$ represents a heteroaryl-cyclopropyl- group, which heteroaryl group is optionally substituted with one or two or three substituents, identically or differently, selected from the group of halogen, hydroxy, $NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^5$ represents a heteroaryl-cyclopropyl- group, which heteroaryl group is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^5$ represents a pyridyl-cyclopropyl- group, which pyridyl group is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^6$ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^6$ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I), in which $R^6$ represents a group selected from a hydrogen atom, fluoro atom, chloro atom.

In another embodiment the invention relates to compounds of formula (I), in which $R^6$ and $R^7$ represent, independently from each other, a group selected from a hydrogen or fluoro atom or $C_1$-$C_3$-alkoxy-.

In another embodiment the invention relates to compounds of formula (I), in which $R^6$ and $R^7$ represent, independently from each other, a group selected from a hydrogen or fluoro atom.

In another embodiment the invention relates to compounds of formula (I), in which $R^6$ represents a hydrogen atom.

In another embodiment the invention relates to compounds of formula (I), in which $R^6$ represents a fluoro atom.

In a preferred embodiment the invention relates to compounds of formula (I), in which $R^6$ is in para position to the 5-fluoro pyrimidine and represents a fluoro atom.

In another embodiment the invention relates to compounds of formula (I), in which $R^7$ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^7$ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I), in which $R^7$ represents a group selected from a hydrogen atom, fluoro atom, chloro atom.

In another embodiment the invention relates to compounds of formula (I), in which $R^7$ represents a hydrogen atom.

In another embodiment the invention relates to compounds of formula (I), in which $R^6$ represents a fluoro atom and $R^7$ represents a hydrogen atom.

In a preferred embodiment the invention relates to compounds of formula (I), in which $R^6$ is in para position to the 5-fluoro pyrimidine and represents a fluoro atom and in which $R^7$ represents a hydrogen atom.

It is to be understood that the present invention relates to any sub-combination within any embodiment of the present invention of compounds of formula (I), supra.

More particularly still, the present invention covers compounds of formula (I) which are disclosed in the Example section of this text, infra.

Very specially preferred are combinations of two or more of the abovementioned preferred embodiments.

In particular, preferred subjects of the present invention are the compounds selected from:

5-Fluoro-4-(4-fluoro-2-methoxyphenyl)-N-{3-[(methylsulfonyl)methyl]phenyl}pyrimidin-2-amine, 4-[2-(Benzyloxy)-4-fluorophenyl]-5-fluoro-N-{3-[(methylsulfonyl)methyl]phenyl}pyrimidin-2-amine, 4-[2-(Benzyloxy)-4-fluorophenyl]-5-fluoro-N-(3-{[(2-methoxyethyl)sulfonyl]methyl}phenyl) pyrimidin-2-amine, 4-[2-(Benzyloxy)-4-fluorophenyl]-N-{3-[(tert-butylsulfonyl)methyl]phenyl}-5-fluoropyrimidin-2-amine, 4-[2-(Benzyloxy)-4-fluorophenyl]-5-fluoro-N-{3-[(propan-2-ylsulfonyl)methyl]phenyl}pyrimidin-2-amine, 4-[2-(Benzyloxy)-4-fluorophenyl]-N-{3-[(cyclohexylsulfonyl)methyl]phenyl}-5-fluoropyrimidin-2-amine, 5-Fluoro-4-(4-fluoro-2-methoxyphenyl)-N-{3-[(propan-2-ylsulfonyl)methyl]phenyl}pyrimidin-2-amine, 2-[(3-{[5-fluoro-4-(4-fluoro-2-methoxyphenyl)pyrimidin-2-yl]amino}benzyl)sulfonyl]ethanol, 4-(3,4-Dihydro-2H-chromen-8-yl)-5-fluoro-N-{3-[(methylsulfonyl)methyl]phenyl}pyrimidin-2-amine, N-{3-[(Cyclopropylsulfonyl)methyl]phenyl}-4-(3,4-dihydro-2H-chromen-8-yl)-5-fluoropyrimidin-2-amine, 4-[2-(Benzyloxy)-4-fluorophenyl]-5-fluoro-N-{3-fluoro-5-[(methylsulfonyl)methyl]phenyl}pyrimidin-2-amine, 5-Fluoro-4-(4-fluoro-2-methoxyphenyl)-N-{3-fluoro-5-[(methylsulfonyl)methyl]phenyl}pyrimidin-2-amine, 4-(2,3-Dihydro-1,4-benzodioxin-5-yl)-5-fluoro-N-{3-[(methylsulfonyl)methyl]phenyl}pyrimidin-2-amine, N-{3-[(Cyclopropylsulfonyl)methyl]phenyl}-5-fluoro-4-(4-fluoro-2-methoxyphenyl)pyrimidin-2-amine, N-{3-[(Benzylsulfonyl)methyl]phenyl}-5-fluoro-4-(4-fluoro-2-methoxyphenyl)pyrimidin-2-amine, 5-Fluoro-4-[4-fluoro-2-(pyridin-3-ylmethoxy)phenyl]-N-{3-[(methylsulfonyl)-methyl]phenyl}pyrimidin-2-amine, 5-Fluoro-4-{2-fluoro-4-[(4-fluorobenzyl)oxy]phenyl}-N-{3-[(methylsulfonyl)-methyl]phenyl}pyrimidin-2-amine, 5-Fluoro-4-{2-fluoro-4-[(3-fluorobenzyl)oxy]phenyl}-N-{3-[(methylsulfonyl)-methyl]phenyl}pyrimidin-2-amine, or their salts, solvates or salts of solvates.

The abovementioned definitions of radicals which have been detailed in general terms or in preferred ranges also apply to the end products of the formula (I) and, analogously, to the starting materials or intermediates required in each case for the preparation.

The invention furthermore relates to a method for the preparation of the compounds of formula (I) according to the invention, in which method a compound of formula (3)

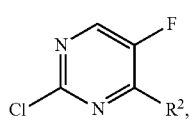

in which $R^2$ is as defined for the compound of general formula (I), is reacted with a compound of formula (4)

4 in which $R^1$, $R^3$ and $R^4$ are as defined for the compound of general formula (I), thus providing a compound of general formula (I) according to the present invention and the resulting compounds of formula (I) are optionally, if appropriate, reacted with the corresponding (i) solvents and/or (ii) bases or acids to the solvates, salts and/or solvates of the salts of the compounds of formula (I).

In one embodiment of the present invention the method for the preparation of the compounds of formula (I) by a coupling reaction of a compound of formula (3) with a compound of formula (4) is carried out in an alcohol or in an inert solvent or in mixtures of such solvents, preferably in 1-butanol or in DMF, THF, DME, dioxane or mixtures thereof, in the presence of an acid, preferably in the presence of hydrogen chloride or 4-methylbenzenesulfonic acid. This reaction is carried out at temperatures ranging from 100° C. to the boiling point of the solvent, preferably it is carried out at temperatures between 130° C.-160° C. in 1-butanol, more preferably at about 140° C. in 1-butanol.

In another embodiment of the present invention the coupling reaction of a compound of formula (3) with a compound of formula (4) is done by a Palladium-catalyzed C—N cross-coupling reaction (for a review on C—N cross-coupling reactions see for example: a) L. Jiang, S. L. Buchwald in 'Metal-Catalyzed Cross-Coupling Reactions', $2^{nd}$ ed.: A. de Meijere, F. Diederich, Eds.: Wiley-VCH: Weinheim, Germany, 2004).

Preferred is the use of suitable palladium precatalysts based upon biarylmonphosphines that are easily activated and ensure the formation of the active mono-ligated Pd(0) complex (see for examples: a) S. L. Buchwald et al, J. Am. Chem. Soc. 2008, 130, 6686; b) S. L. Buchwald et al, J. Am. Chem. Soc. 2008, 130, 13552). The reactions are run in the presence of a weak base at elevated temperatures (see for example: a) S. L: Buchwald et al, Tet. Lett. 2009, 50, 3672).

Most preferred is the herein described use of chloro(2-dicyclohexylphosphino-2',4',6'-tri-iso-propyl-1,1'-biphenyl)[2-(2-aminoethyl)phenyl]palladium(II) methyl-tert-butylether adduct, 2-dicyclohexylphosphino-2',4',6'-triisopropylbiphenyl and potassium phosphate in toluene and 1-methylpyrrolidin-2-one. The reactions are preferably run under argon for 3 hours at 130° C. in a microwave oven or in an oil bath.

The invention furthermore relates to a method for the preparation of the compounds of formula (3) according to the invention, in which method 2-4-dichloro-5-fluoro-pyrimidine (1),

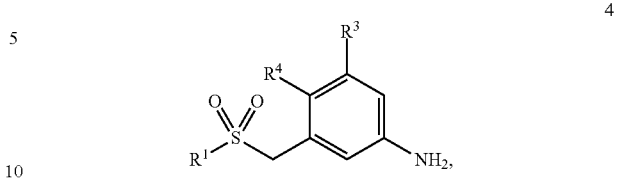

is reacted with a compound of formula (2)

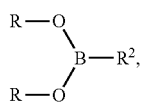

in which $R^2$ is as defined for the compound of general formula (I) according to the invention, and R represent, independently from each other, a hydrogen atom, or a $C_1$-$C_{10}$-alkyl- group or, alternatively, both R together form a R—R group, which is —C(CH$_3$)$_2$—C(CH$_3$)$_2$—, thus providing a compound of general formula (3) according to the invention and the resulting compounds of formula (3) according to the invention are optionally, if appropriate, reacted with the corresponding (i) solvents and/or (ii) bases or acids to the solvates, salts and/or solvates of the salts thereof.

Compounds of general formula (2) can be prepared analogously to known processes (review: D. G. Hall, Boronic Acids, 2005 WILEY-VCH Verlag GmbH & Co. KGaA, Weinheim, ISBN 3-527-30991-8 and references cited herein). Further, a wide variety of compounds of general formula (2) is commercially available.

The coupling reaction of 2-4-dichloro-5-fluoro-pyrimidine (1) with compounds of formula (2) is catalyzed by Pd catalysts, e.g. by Pd(0) catalysts or by Pd(II) catalysts. Examples for Pd(0) catalysts are tetrakis(triphenylphosphine)palladium (0) [Pd(PPh$_3$)$_4$] or tris(dibenzylideneacetone)di-palladium (0) [Pd$_2$(dba)$_3$], examples for Pd(II) catalysts dichlorobis (triphenylphosphine)-palladium(II) [Pd(PPh$_3$)$_2$Cl$_2$], palladium(II) acetate and triphenylphosphine or [1,1'-bis (diphenylphosphino)ferrocene]palladium dichloride (review: D. G. Hall, Boronic Acids, 2005 WILEY-VCH Verlag GmbH & Co. KGaA, Weinheim, ISBN 3-527-30991-8 and references cited therein).

This reaction is preferably carried out in aprotic or protic solvents, preferably in a mixture of aprotic and protic solvents, more preferably in solvents like, for example, 1,2-dimethoxyethane, dioxane, dimethylformamid, tetrahydrofuran, or isopropanol with water (review: D. G. Hall, Boronic Acids, 2005 WILEY-VCH Verlag GmbH & Co. KGaA, Weinheim, ISBN 3-527-30991-8 and references cited therein).

Preferably the reaction is carried out in the presence of a suitable base, such as for example aqueous potassium carbonate, aqueous sodium bicarbonate or potassium phosphate (review: D. G. Hall, Boronic Acids, 2005 WILEY-VCH Verlag GmbH & Co. KGaA, Weinheim, ISBN 3-527-30991-8 and references cited therein).

The reaction is performed at temperatures ranging from room temperature (=20° C.) to the boiling point of the solvent. Further on, the reaction can be performed at temperatures above the boiling point using pressure tubes and a microwave oven. (review: D. G. Hall, Boronic Acids, 2005 WILEY-VCH Verlag GmbH & Co. KGaA, Weinheim, ISBN 3-527-30991-8 and references cited therein).

The reaction is preferably completed after 1 to 36 hours of reaction time.

The preparation of the compounds of general formula (I) according to the invention can be illustrated by the following synthesis scheme 1:

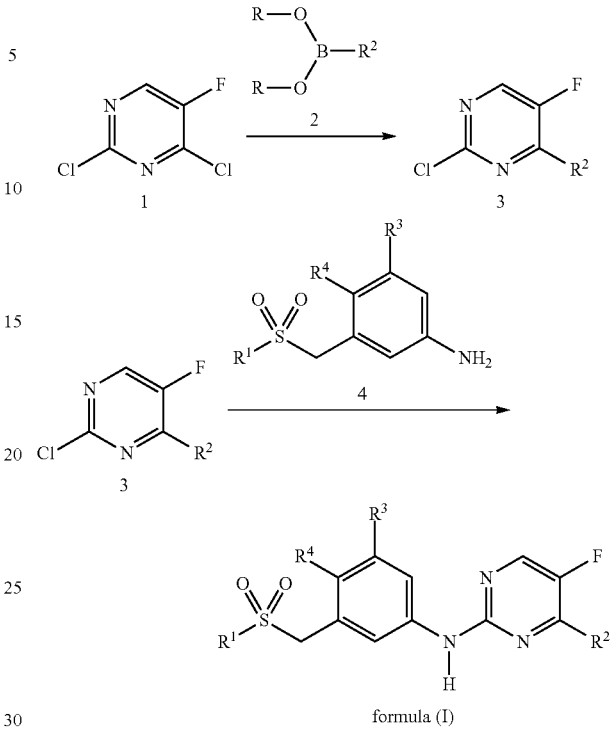

2,4-Dichloro-5-fluoro-pyrimidine (1) is commercially available.

A number of compounds of general formula (4) are commercially available. Further on, the compounds of formula (4) are known or can be prepared analogously to known processes. For example, by reaction of suitable benzylchlorides or -bromides of formula (5) with suitable thiols of formula (6) under basic conditions the corresponding thioethers of formula (7) can be prepared (scheme 2, see for example: Sammond et al, Bioorg. Med. Chem. Lett. 2005, 15, 3519)

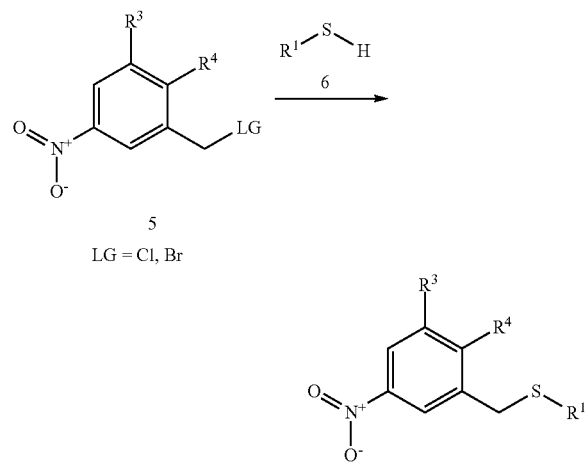

Oxidation of (7) gives the corresponding sulfones of formula (8). The oxidation can be prepared analogously to known processes (scheme 3, see for example: Sammond et al; Bioorg. Med. Chem. Lett. 2005, 15, 3519).

Scheme 3

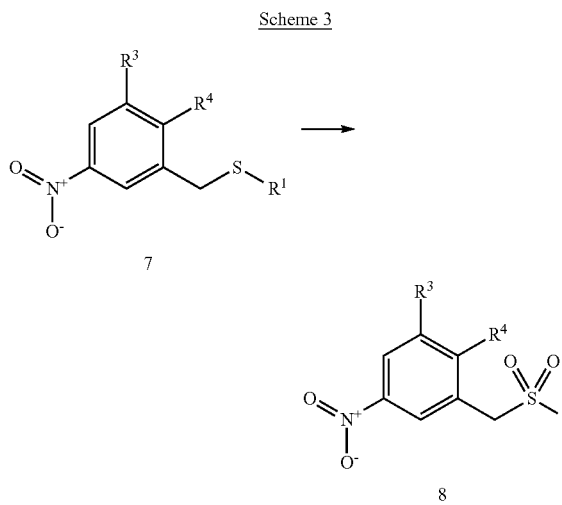

Finally, reduction of the nitro group gives the desired anilines of formula (4). The reduction can be prepared analogously to known processes (scheme 4, see for example: Sammond et al; Bioorg. Med. Chem. Lett. 2005, 15, 3519).

Scheme 4

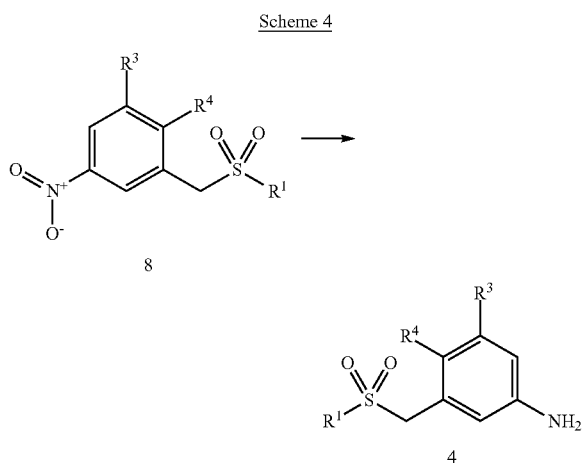

The compounds according to the invention show a valuable pharmacological and pharmacokinetic spectrum of action which could not have been predicted.

They are therefore suitable for use as medicaments for the treatment and/or prophylaxis of disorders in humans and animals.

Within the scope of the present invention, the term "treatment" includes prophylaxis.

The pharmaceutical activity of the compounds according to the invention can be explained by their action as inhibitors of CDK9. Thus, the compounds according to the general formula (I) as well as pharmaceutically acceptable salts thereof are used as inhibitors for CDK9.

Furthermore, the compounds according to the invention show a particularly high potency (demonstrated by a low $IC_{50}$ value in the CDK9/CycT1 assay) for inhibiting CDK9 activity.

In context of the present invention, the $IC_{50}$ value with respect to CDK9 can be determined by the methods described in the method section below. Preferably, it is determined according to Method 1a. ("CDK9/CycT1 kinase assay") described in the Materials and Method section below.

Surprisingly it turned out that the compounds according to the general formula (I) as well as pharmaceutically acceptable salts thereof selectively inhibit CDK9 in comparison to other cyclin-dependent protein kinases, preferably in comparison to CDK2. Thus, the compounds according to the general formula (I) as well as pharmaceutically acceptable salts thereof are preferably used as selective inhibitors for CDK9.

Compounds of the present invention according to general formula (I) show a significantly stronger CDK9 than CDK2 inhibition.

In context of the present invention, the $IC_{50}$ value with respect to CDK2 can be determined by the methods described in the method section below. Preferably, it is determined according to Method 2. ("CDK2/CycE kinase assay") described in the Materials and Method section below.

Further, as compared to the CDK9 inhibitors described in the prior art, preferred compounds of the present invention according to general formula (I) show a surprisingly high potency for inhibiting CDK9 activity at high ATP concentrations, which is demonstrated by their low $IC_{50}$ value in the CDK9/CycT1 high ATP kinase assay. Thus, these compounds have a lower probability to be competed out of the ATP-binding pocket of CDK9/CycT1 kinase due to the high intracellular ATP concentration (R. Copeland et al., Nature Reviews Drug Discovery 2006, 5, 730-739). According to this property the compounds of the present invention are particularly able to inhibit CDK9/CycT1 within cells for a longer period of time as compared to classical ATP competitive kinase inhibitors. This increases the anti-tumor cell efficacy at pharmacokinetic clearance-mediated declining serum concentrations of the inhibitor after dosing of a patient or an animal.

In context of the present invention, the $IC_{50}$ value with respect to CDK9 at high ATP concentrations can be determined by the methods described in the method section below. Preferably, it is determined according to Method 1b ("CDK9/CycT1 high ATP kinase assay") as described in the Materials and Method section below.

Further, preferred compounds of the present invention according to formula (I) show an improved anti-proliferative activity in tumor cell lines such as HeLa compared to the CDK9 inhibitors described in the prior art. In context of the present invention, the anti-proliferative activity in tumor cell lines such as HeLa is preferably determined according to Method 3. ("Proliferation Assay") as described in the Materials and Method section below.

Further, preferred compounds of the present invention according to formula (I) are characterized by improved pharmacokinetic properties, such as an increased apparent Caco-2 permeability ($P_{app}$ A-B) across Caco-2 cell monolayers, compared to the compounds known from the prior art.

Further, preferred compounds of the present invention according to formula (I) are characterized by improved pharmacokinetic properties, such as a decreased efflux ratio (efflux ratio=$P_{app}$ B-A/$P_{app}$ A-B) from the basal to apical compartment across Caco-2 cell monolayers, compared to the compounds known from the prior art.

In context of the present invention, the apparent Caco-2 permeability values from the basal to apical compartment ($P_{app}$ A-B) or the efflux ratio (defined as the ratio (($P_{app}$ B-A)/($P_{app}$ A-B)) are preferably determined according to Method 4. ("Caco-2 Permeation Assay") described in the Materials and Method section below.

A further subject matter of the present invention is the use of the compounds of general formula (I) according to the invention for the treatment and/or prophylaxis of disorders, preferably of disorders relating to or mediated by CDK9 activity, in particular of hyper-proliferative disorders, virally induced infectious diseases and/or of cardiovascular diseases, more preferably of hyper-proliferative disorders.

The compounds of the present invention may be used to inhibit the activity or expression of CDK9. Therefore, the compounds of formula (I) are expected to be valuable as therapeutic agents. Accordingly, in another embodiment, the present invention provides a method of treating disorders relating to or mediated by CDK9 activity in a patient in need of such treatment, comprising administering to the patient an effective amount of a compound of formula (I) as defined above. In certain embodiments, the disorders relating to CDK9 activity are hyper-proliferative disorders, virally induced infectious diseases and/or of cardiovascular diseases, more preferably hyper-proliferative disorders, particularly cancer.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or a disorder associated with reduced or insufficient programmed cell death (apoptosis) or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The term "disorders relating to or mediated by CDK9" shall include diseases associated with or implicating CDK9 activity, for example the hyperactivity of CDK9, and conditions that accompany with these diseases. Examples of "disorders relating to or mediated by CDK9" include disorders resulting from increased CDK9 activity due to mutations in genes regulating CDK9 activity auch as LARP7, HEXIM1/2 or 7sk snRNA, or disorders resulting from increased CDK9 activity due to activation of the CDK9/cyclinT/RNApolymerase II complex by viral proteins such as HIV-TAT or HTLV-TAX or disorders resulting from increased CDK9 activity due to activation of mitogenic signaling pathways.

The term "hyperactivity of CDK9" refers to increased enzymatic activity of CDK9 as compared to normal non-diseased cells, or it refers to increased CDK9 activity leading to unwanted cell proliferation, or to reduced or insufficient programmed cell death (apoptosis), or mutations leading to constitutive activation of CDK9.

The term "hyper-proliferative disorder" includes disorders involving the undesired or uncontrolled proliferation of a cell and it includes disorders involving reduced or insufficient programmed cell death (apoptosis). The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, hydrate or solvate thereof which is effective to treat or prevent the disorder.

Hyper-proliferative disorders in the context of this invention include, but are not limited to, e.g., psoriasis, keloids and other hyperplasias affecting the skin, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia (BPH), and solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Examples of breast cancer include, but are not limited to invasive ductal carcinoma, invasive lobular carcinoma, ductal carcinoma in situ, and lobular carcinoma in situ, and canine or feline mammary carcinoma.

Examples of cancers of the respiratory tract include, but are not limited to small-cell and non-small-cell lung carcinoma, as well as bronchial adenoma, pleuropulmonary blastoma, and mesothelioma.

Examples of brain cancers include, but are not limited to brain stem and hypophtalmic glioma, cerebellar and cerebral astrocytoma, glioblastoma, medulloblastoma, ependymoma, as well as neuroectodermal and pineal tumor.

Tumors of the male reproductive organs include, but are not limited to prostate and testicular cancer.

Tumors of the female reproductive organs include, but are not limited to endometrial, cervical, ovarian, vaginal and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers. Anal gland adenocarcinomas, mast cell tumors.

Tumors of the urinary tract include, but are not limited to bladder, penile, kidney, renal pelvis, ureter, urethral, and hereditary and sporadic papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer, mast cell tumors.

Head-and-neck cancers include, but are not limited to laryngeal, hypopharyngeal, nasopharyngeal, oropharyngeal cancer, lip and oral cavity cancer, and squamous cell cancer. Oral melanoma.

Lymphomas include, but are not limited to ADS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma. Malignant histiocytosis, fibrosarcoma, hemangiosarcoma, hemangiopericytoma, leiomyosarcoma.

Leukemias include, but are not limited to acute myeloid leukemia, acute lymphoblastic leukemia, chronic lymphocytic leukemia, chronic myelogenous leukemia, and hairy cell leukemia.

Fibrotic proliferative disorders, i.e. the abnormal formation of extracellular matrices, that may be treated with the compounds and methods of the present invention include lung fibrosis, atherosclerosis, restenosis, hepatic cirrhosis, and mesangial cell proliferative disorders, including renal diseases such as glomerulonephritis, diabetic nephropathy, malignant nephrosclerosis, thrombotic microangiopathy syndromes, transplant rejection, and glomerulopathies.

Other conditions in humans or other mammals that may be treated by administering a compound of the present invention include tumor growth, retinopathy, including diabetic retinopathy, ischemic retinal-vein occlusion, retinopathy of prematurity and age-related macular degeneration, rheumatoid arthritis, psoriasis, and bullous disorders associated with subepidermal blister formation, including bullous pemphigoid, erythema multiforme and dermatitis herpetiformis.

The compounds of the present invention may also be used to prevent and treat diseases of the airways and the lung, diseases of the gastrointestinal tract as well as diseases of the bladder and bile duct.

The disorders mentioned above have been well characterized in humans, but also exist with a similar etiology in other animals, including mammals, and can be treated by administering pharmaceutical compositions of the present invention.

In a further aspect of the present invention, the compounds according to the invention are used in a method for preventing and/or treating infectious diseases, in particular virally induced infectious diseases. The virally induced infectious diseases, including opportunistic diseases, are caused by retroviruses, hepadnaviruses, herpesviruses, flaviviridae, and/or adenoviruses. In a further preferred embodiment of this method, the retroviruses are selected from lentiviruses or oncoretroviruses, wherein the lentivirus is selected from the group comprising: HIV-1, HIV-2, FIV, BIV, SIVs, SHIV, CAEV, VMV or EIAV, preferably HIV-1 or HIV-2 and wherein the oncoretrovirus is selected from the group of: HTLV-I, HTLV-II or BLV. In a further preferred embodiment of this method, the hepadnavirus is selected from HBV, GSHV or WHV, preferably HBV, the herpesivirus is selected from the group comprising: HSV I, HSV II, EBV, VZV, HCMV or HHV 8, preferably HCMV and the flaviviridae is selected from HCV, West nile or Yellow Fever.

The compounds according to general formula (I) are also useful for prophylaxis and/or treatment of cardiovascular diseases such as cardiac hypertrophy, adult congenital heart disease, aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation, Behcet syndrome, bradycardia, cardiac tamponade, cardiomegaly, congestive cardiomyopathy, hypertrophic cardiomyopathy, restrictive cardiomyopathy, cardiovascular disease prevention, carotid stenosis, cerebral hemorrhage, Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, hematoma, subdural, Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, restenosis, Sneddon syndrome, stenosis, superior vena cava syndrome, syndrome X, tachycardia, Takayasu's arteritis, hereditary hemorrhagic telangiectasia, telangiectasis, temporal arteritis, tetralogy of fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome.

Preferred are cardiac hypertrophy, adult congenital heart disease, aneurysms, angina, angina pectoris, arrhythmias, cardiovascular disease prevention, cardiomyopathies, congestive heart failure, myocardial infarction, pulmonary hypertension, hypertrophic growth, restenosis, stenosis, thrombosis and arteriosclerosis.

A further subject matter of the present invention is the use of the compounds of general formula (I) according to the invention for the treatment and/or prophylaxis of disorders, in particular of the disorders mentioned above.

A further subject matter of the present invention are the compounds according to the invention for use in a method for the treatment and/or prophylaxis of the disorders mentioned above.

A preferred subject matter of the present invention are the compounds according to the invention for the use in a method for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas or ovarian carcinomas.

A further subject matter of the present invention is the use of the compounds according to the invention in the manufacture of a medicament for the treatment and/or prophylaxis of disorders, in particular the disorders mentioned above.

A preferred subject matter of the present invention is the use of the compounds according to the invention in the manufacture of a medicament for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas or ovarian carcinomas.

A further subject matter of the present invention is a method for the treatment and/or prophylaxis of disorders, in particular the disorders mentioned above, using an effective amount of the compounds according to the invention.

A preferred subject matter of the present invention is a method for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas or ovarian carcinomas.

Another aspect of the present invention relates to pharmaceutical combinations comprising a compound of general formula (I) according to the invention in combination with at least one or more further active ingredients.

As used herein the term "pharmaceutical combination" refers to a combination of at least one compound of general formula (I) according to the invention as active ingredient together with at least one other active ingredient with or without further ingredients, carrier, diluents and/or solvents.

Another aspect of the present invention relates to pharmaceutical compositions comprising a compound of general formula (I) according to the invention in combination with an inert, nontoxic, pharmaceutically suitable adjuvant.

As used herein the term "pharmaceutical composition" refers to a galenic formulation of at least one pharmaceutically active agent together with at least one further ingredient, carrier, diluent and/or solvent.

Another aspect of the present invention relates to the use of the pharmaceutical combinations and/or the pharmaceutical compositions according to the invention for the treatment and/or prophylaxis of disorders, in particular of the disorders mentioned above.

Compounds of formula (I) may be administered as the sole pharmaceutical agent or in combination with one or more additional therapeutic agents where the combination causes no unacceptable adverse effects. This pharmaceutical combination includes administration of a single pharmaceutical dosage formulation which contains a compound of formula (I) and one or more additional therapeutic agents, as well as administration of the compound of formula (I) and each additional therapeutic agent in its own separate pharmaceutical dosage formulation. For example, a compound of formula (I) and a therapeutic agent may be administered to the patient together in a single oral dosage composition such as a tablet or capsule, or each agent may be administered in separate dosage formulations.

Where separate dosage formulations are used, the compound of formula (I) and one or more additional therapeutic agents may be administered at essentially the same time (e.g., concurrently) or at separately staggered times (e.g., sequentially).

In particular, the compounds of the present invention may be used in fixed or separate combination with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other anti-tumor drugs. In this regard, the following is a non-limiting list of examples of secondary agents that may be used in combination with the compounds of the present invention:

Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, and mitolactol; platinum-coordinated alkylating compounds include, but are not limited to, cisplatin, carboplatin, eptaplatin, lobaplatin, nedaplatin, oxaliplatin, and satraplatin;

Anti-metabolites include, but are not limited to, methotrexate, 6-mercaptopurine riboside, mercaptopurine, 5-fluorouracil alone or in combination with leucovorin, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosfite, disodium premetrexed, pentostatin, pelitrexol, raltitrexed, triapine, trimetrexate, vidarabine, vincristine, and vinorelbine;

Hormonal therapy agents include, but are not limited to, exemestane, Lupron, anastrozole, doxercalciferol, fadrozole, formestane, 11-beta hydroxysteroid dehydrogenase 1 inhibitors, 17-alpha hydroxylase/17,20 lyase inhibitors such as abiraterone acetate, 5-alpha reductase inhibitors such as finasteride and episteride, anti-estrogens such as tamoxifen citrate and fulvestrant, Trelstar, toremifene, raloxifene, lasofoxifene, letrozole, anti-androgens such as bicalutamide, flutamide, mifepristone, nilutamide, Casodex, and anti-progesterones and combinations thereof;

Plant-derived anti-tumor substances include, e.g., those selected from mitotic inhibitors, for example epothilones such as sagopilone, ixabepilone and epothilone B, vinblastine, vinflunine, docetaxel, and paclitaxel;

Cytotoxic topoisomerase inhibiting agents include, but are not limited to, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, and combinations thereof;

Immunologicals include interferons such as interferon alpha, interferon alpha-2a, interferon alpha-2b, interferon beta, interferon gamma-1a and interferon gamma-n1, and other immune enhancing agents such as L19-IL2 and other IL2 derivatives, filgrastim, lentinan, sizofilan, TheraCys, ubenimex, aldesleukin, alemtuzumab, BAM-002, dacarbazine, daclizumab, denileukin, gemtuzumab, ozogamicin, ibritumomab, imiquimod, lenograstim, lentinan, melanoma vaccine (Corixa), molgramostim, sargramostim, tasonermin, tecleukin, thymalasin, tositumomab, Vimlizin, epratuzumab, mitumomab, oregovomab, pemtumomab, and Provenge; Merial melanoma vaccine Biological response modifiers are agents that modify defense mechanisms of living organisms or biological responses such as survival, growth or differentiation of tissue cells to direct them to have anti-tumor activity; such agents include, e.g., krestin, lentinan, sizofiran, picibanil, ProMune, and ubenimex;

Anti-angiogenic compounds include, but are not limited to, acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin;

Antibodies include, but are not limited to, trastuzumab, cetuximab, bevacizumab, rituximab, ticilimumab, ipilimumab, lumiliximab, catumaxomab, atacicept, oregovomab, and alemtuzumab;

VEGF inhibitors such as, e.g., sorafenib, DAST, bevacizumab, sunitinib, recentin, axitinib, aflibercept, telatinib, brivanib alaninate, vatalanib, pazopanib, and ranibizumab; Palladia EGFR (HER1) inhibitors such as, e.g., cetuximab, panitumumab, vectibix, gefitinib, erlotinib, and Zactima;

HER2 inhibitors such as, e.g., lapatinib, tratuzumab, and pertuzumab;

mTOR inhibitors such as, e.g., temsirolimus, sirolimus/Rapamycin, and everolimus;

c-Met inhibitors;

PI3K and AKT inhibitors;

CDK inhibitors such as roscovitine and flavopiridol;

Spindle assembly checkpoints inhibitors and targeted anti-mitotic agents such as PLK inhibitors, Aurora inhibitors (e.g. Hesperadin), checkpoint kinase inhibitors, and KSP inhibitors;

HDAC inhibitors such as, e.g., panobinostat, vorinostat, MS275, belinostat, and LBH589;

HSP90 and HSP70 inhibitors;

Proteasome inhibitors such as bortezomib and carfilzomib;

Serine/threonine kinase inhibitors including MEK inhibitors (such as e.g. RDEA 119) and Raf inhibitors such as sorafenib;

Farnesyl transferase inhibitors such as, e.g., tipifamib;

Tyrosine kinase inhibitors including, e.g., dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab, pertuzumab, and c-Kit inhibitors; Palladia, masitinib Vitamin D receptor agonists;

Bcl-2 protein inhibitors such as obatoclax, oblimersen sodium, and gossypol;

Cluster of differentiation 20 receptor antagonists such as, e.g., rituximab;

Ribonucleotide reductase inhibitors such as, e.g., gemcitabine;

Tumor necrosis apoptosis inducing ligand receptor 1 agonists such as, e.g., mapatumumab;

5-Hydroxytryptamine receptor antagonists such as, e.g., rEV598, xaliprode, palonosetron hydrochloride, granisetron, Zindol, and AB-1001;

Integrin inhibitors including alpha5-beta1 integrin inhibitors such as, e.g., E7820, JSM 6425, volociximab, and endostatin;

Androgen receptor antagonists including, e.g., nandrolone decanoate, fluoxymesterone, Android, Prost-aid, andromustine, bicalutamide, flutamide, apo-cyproterone, apo-flutamide, chlormadinone acetate, Androcur, Tabi, cyproterone acetate, and nilutamide;

Aromatase inhibitors such as, e.g., anastrozole, letrozole, testolactone, exemestane, aminoglutethimide, and formestane;

Matrix metalloproteinase inhibitors;

Other anti-cancer agents including, e.g., alitretinoin, ampligen, atrasentan bexarotene, bortezomib, bosentan, calcitriol, exisulind, fotemustine, ibandronic acid, miltefosine, mitoxantrone, I-asparaginase, procarbazine, dacarbazine, hydroxycarbamide, pegaspargase, pentostatin, tazaroten, velcade, gallium nitrate, canfosfamide, darinaparsin, and tretinoin.

The compounds of the present invention may also be employed in cancer treatment in conjunction with radiation therapy and/or surgical intervention.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone, (2) provide for the administration of lesser amounts of the administered chemotherapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or (8) yield efficacy and tolerability results at least as good as those of the agents used alone, compared to known instances where other cancer agent combinations produce antagonistic effects.

Furthermore, the compounds of formula (I) may be utilized, as such or in compositions, in research and diagnostics, or as analytical reference standards, and the like, which are well known in the art.

The compounds according to the invention can act systemically and/or locally. For this purpose, they can be administered in a suitable way, such as, for example, by the oral, parenteral, pulmonal, nasal, sublingual, lingual, buccal, rectal, dermal, transdermal, conjunctival or otic route, or as an implant or stent.

For these administration routes, it is possible to administer the compounds according to the invention in suitable application forms.

Suitable for oral administration are administration forms which work as described in the prior art and deliver the compounds according to the invention rapidly and/or in modified form, which comprise the compounds according to the invention in crystalline and/or amorphous and/or dissolved form, such as, for example, tablets (coated or uncoated, for example tablets provided with enteric coatings or coatings whose dissolution is delayed or which are insoluble and which control the release of the compound according to the invention), tablets which rapidly decompose in the oral cavity, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbally) or with inclusion of absorption (for example intramuscularly, subcutaneously, intracutaneously, percutaneously or intraperitoneally). Administration forms suitable for parenteral administration are, inter alia, preparations for injection and infusion in the form of solutions, suspensions, emulsions, lyophilizates or sterile powders.

Examples suitable for the other administration routes are pharmaceutical forms for inhalation (inter alia powder inhalers, nebulizers), nasal drops/solutions/sprays; tablets to be administered lingually, sublingually or buccally, films/wafers or capsules, suppositories, preparations for the eyes or ears, vaginal capsules, aqueous suspensions (lotions, shaking mixtures), lipophilic suspensions, ointments, creams, transdermal therapeutic systems (such as plasters, for example), milk, pastes, foams, dusting powders, implants or stents.

The compounds according to the invention can be converted into the stated administration forms. This can take place in a manner known per se by mixing with inert, non-toxic, pharmaceutically suitable adjuvants. These adjuvants include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and flavour- and/or odour-masking agents.

The present invention furthermore provides medicaments comprising at least one compound according to the invention, usually together with one or more inert, nontoxic, pharmaceutically suitable adjuvants, and their use for the purposes mentioned above.

When the compounds of the present invention are administered as pharmaceuticals, to humans or animals, they can be given per se or as a pharmaceutical composition containing, for example, 0.1% to 99.5% (more preferably 0.5% to 90%) of active ingredient in combination with one or more inert, nontoxic, pharmaceutically suitable adjuvants.

Regardless of the route of administration selected, the compounds of the invention of general formula (I) and/or the pharmaceutical composition of the present invention are formulated into pharmaceutically acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient without being toxic to the patient.

Materials and Methods:

The percentage data in the following tests and examples are percentages by weight unless otherwise indicated; parts are parts by weight. Solvent ratios, dilution ratios and concentration data of liquid/liquid solutions are in each case based on volume.

Examples were tested in selected biological assays one or more times. When tested more than once, data are reported as either average values or as median values, wherein
- the average value, also referred to as the arithmetic mean value, represents the sum of the values obtained divided by the number of times tested, and
- the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro pharmacological properties of the compounds can be determined according to the following assays and methods.

1a. CDK9/CycT1 Kinase Assay:

CDK9/CycT1-inhibitory activity of compounds of the present invention was quantified employing the CDK9/CycT1 TR-FRET assay as described in the following paragraphs:

Recombinant full-length His-tagged human CDK9 and CycT1, expressed in insect cells and purified by Ni-NTA affinity chromatography, were purchased from Invitrogen (Cat. No PV4131). As substrate for the kinase reaction biotinylated peptide biotin-Ttds-YISPLKSPYKISEG (C-terminus in amid form) was used which can be purchased e.g. form the company JERINI Peptide Technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of CDK9/CycT1 in aqueous assay buffer [50 mM Tris/HCl pH 8.0, 10 mM MgCl$_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 1 µg/mL. The reaction was stopped by the addition of 5 µl of a solution of TR-FRET detection reagents (0.2 µM streptavidine-XL665 [Cisbio Bioassays, Codolet, France] and 1 nM anti-RB(pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and IC$_{50}$ values were calculated by a 4 parameter fit using an inhouse software.

1b. CDK9/CycT1 High ATP Kinase Assay

CDK9/CycT1-inhibitory activity of compounds of the present invention at a high ATP concentration after preincubation of enzyme and test compounds was quantified employing the CDK9/CycT1 TR-FRET assay as described in the following paragraphs.

Recombinant full-length His-tagged human CDK9 and CycT1, expressed in insect cells and purified by Ni-NTA affinity chromatography, were purchase from Invitrogen (Cat. No PV4131). As substrate for the kinase reaction biotinylated peptide biotin-Ttds-YISPLKSPYKISEG (C-terminus in amid form) was used which can be purchased e.g. form the company JERINI peptide technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of CDK9/CycT1 in aqueous assay buffer [50 mM Tris/HCl pH 8.0, 10 mM MgCl$_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 3.3 mM=>final conc. in the 5 µl assay volume is 2 mM) and substrate (1.67 µM=>final conc. in the 5 µl assay volume is 1 μM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 0.5 μg/mL. The reaction was stopped by the addition of 5 μl of a solution of TR-FRET detection reagents (0.2 μM streptavidine-XL665 [Cisbio Bioassays, Codolet, France] and 1 nM anti-RB(pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.1 nM (20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

2. CDK2/CycE Kinase Assay:

CDK2/CycE-inhibitory activity of compounds of the present invention was quantified employing the CDK2/CycE TR-FRET assay as described in the following paragraphs:

Recombinant fusion proteins of GST and human CDK2 and of GST and human CycE, expressed in insect cells (Sf9) and purified by Glutathion-Sepharose affinity chromatography, were purchased from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI Peptide Technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 μl of a solution of CDK2/CycE in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 μl of a solution of adenosine-tri-phosphate (ATP, 16.7 μM=>final conc. in the 5 μl assay volume is 10 μM) and substrate (1.25 μM=>final conc. in the 5 μl assay volume is 0.75 μM) in assay buffer and the resulting mixture was incubated for a reaction time of 25 min at 22° C. The concentration of CDK2/CycE was adjusted depending of the activity of the enzyme lot and was chosen appropriate to have the assay in the linear range, typical concentrations were in the range of 130 ng/mL. The reaction was stopped by the addition of 5 μl of a solution of TR-FRET detection reagents (0.2 μM streptavidine-XL665 [Cisbio Bioassays, Codolet, France] and 1 nM anti-RB(pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.1 nM (20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and IC50 values were calculated by a 4 parameter fit using an inhouse software.

3. Proliferation Assay:

Cultivated tumour cells (HeLa, human cervical tumour cells, ATCC CCL-2; NCI-H460, human non-small cell lung carcinoma cells, ATCC HTB-177; A2780, human ovarian carcinoma cells, ECACC #93112519; DU 145, hormone-independent human prostate carcinoma cells, ATCC HTB-81; HeLa-MaTu-ADR, multidrug-resistant human cervical carcinoma cells, EPO-GmbH Berlin; Caco-2, human colorectal carcinoma cells, ATCC HTB-37; B16F10, mouse melanoma cells, ATCC CRL-6475) were plated at a density of 5,000 cells/well (DU145, HeLa-MaTu-ADR), 3,000 cells/well (NCI-H460, HeLa), 2,500 cells/well (A2780), 1,500 cells/well (Caco-2), or 1,000 cells/well (B16F10) in a 96-well multititer plate in 200 μL of their respective growth medium supplemented 10% fetal calf serum. After 24 hours, the cells of one plate (zero-point plate) were stained with crystal violet (see below), while the medium of the other plates was replaced by fresh culture medium (200 μl), to which the test substances were added in various concentrations (0 μM, as well as in the range of 0.001-10 μM; the final concentration of the solvent dimethyl sulfoxide was 0.5%). The cells were incubated for 4 days in the presence of test substances. Cell proliferation was determined by staining the cells with crystal violet: the cells were fixed by adding 20 μl/measuring point of an 11% glutaric aldehyde solution for 15 minutes at room temperature. After three washing cycles of the fixed cells with water, the plates were dried at room temperature. The cells were stained by adding 100 μl/measuring point of a 0.1% crystal violet solution (pH 3.0). After three washing cycles of the stained cells with water, the plates were dried at room temperature. The dye was dissolved by adding 100 μl/measuring point of a 10% acetic acid solution. The extinction was determined by photometry at a wavelength of 595 nm. The change of cell number, in percent, was calculated by normalization of the measured values to the extinction values of the zero-point plate (=0%) and the extinction of the untreated (0 μm) cells (=100%). The $IC_{50}$ values (inhibitory concentration at 50% of maximal effect) were determined by means of a 4 parameter fit.

4. Caco-2 Permeation Assay:

Caco-2 cells (purchased from DSMZ Braunschweig, Germany) were seeded at a density of $4.5 \times 10^4$ cells per well on 24 well insert plates, 0.4 μm pore size, and grown for 15 days in DMEM medium supplemented with 10% fetal bovine serum, 1% GlutaMAX (100×, GIBCO), 100 U/mL penicillin, 100 μg/mL streptomycin (GIBCO) and 1% non essential amino acids (100×). Cells were maintained at 37° C. in a humified 5% CO2 atmosphere. Medium was changed every 2-3 day. Before running the permeation assay, the culture medium was replaced by a FCS-free hepes-carbonate transport buffer (pH 7.2). For assessment of monolayer integrity the transepithelial electrical resistance (TEER) was measured. Test compounds were predissolved in DMSO and added either to the apical or basolateral compartment in final concentration of 2 μM in transport buffer. Before and after 2 h incubation at 37° C. samples were taken from both compartments. Analysis of compound content was done after precipitation with methanol by LC/MS/MS analysis. Permeability (Papp) was calculated in the apical to basolateral (A→B) and basolateral to apical (B→A) directions. The apparent permeability was calculated using following equation:

$$Papp=(Vr/Po)(1/S)(P2/t)$$

Where Vr is the volume of medium in the receiver chamber, Po is the measured peak area or height of the test drug in the donor chamber at t=o, S the surface area of the monolayer, P2 is the measured peak area of the test drug in the acceptor chamber after 2 h of incubation, and t is the incubation time. The efflux ratio basolateral (B) to apical (A) was calculated by dividing the Papp B–A by the Papp A–B. In addition the compound recovery was calculated. The following reference compounds were used for the classification of the permeability class: Antipyrine, Pyrazosin, Verapamil, Fluvastatin, Cimetidine, Ranitidine, Atenolol, Sulfasalazine.

PREPARATIVE EXAMPLES

Syntheses of Compounds

The syntheses of the disubstituted 5-fluoro-pyrimidines according to the present invention are preferably carried out according to the general synthetic sequence, shown in scheme 1.

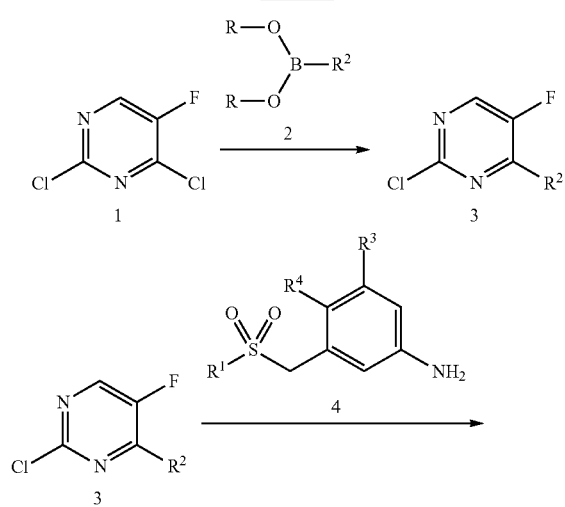

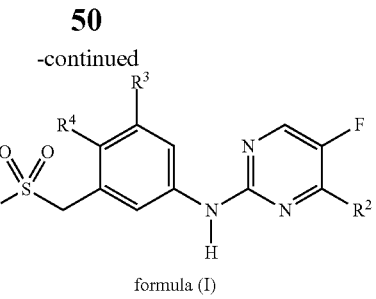

formula (I)

In the first step 2,4-dichloro-5-fluoropyrimidine (1) is reacted with a boronic acid derivative $R^2$—$B(OR)_2$ of formula (2) to give a compound of formula (3). The boronic acid derivative (2) may be a boronic acid (R=—H) or an ester of the boronic acid, e.g. its isopropyl ester (R=—CH(CH_3)_2), preferably an ester derived from pinacol in which the boronic acid intermediate forms a 2-aryl-4,4,5,5-tetramethyl-1,3,2-dioxaborolane (R—R=—C(CH_3)_2—C(CH_3)_2—).

The coupling reaction is catalyzed by palladium catalysts, e.g. by Pd(0) catalysts like tetrakis(triphenylphosphine)palladium(0) [Pd(PPh_3)_4], tris(dibenzylideneacetone)di-palladium(0) [Pd_2(dba)_3], or by Pd(II) catalysts like dichlorobis(triphenylphosphine)-palladium(II) [Pd(PPh_3)_2Cl_2], palladium(II) acetate and triphenylphosphine or by [1,1'-bis(diphenylphosphino)ferrocene]palladium dichloride.

The reaction is preferably carried out in a mixture of a solvent like 1,2-dimethoxyethane, dioxane, DMF, DME, THF, or isopropanol with water and in the presence of a base like potassium carbonate, sodium bicarbonate or potassium phosphate.

(review: D. G. Hall, Boronic Acids, 2005 WILEY-VCH Verlag GmbH & Co. KGaA, Weinheim, ISBN 3-527-30991-8 and references cited therein).

In the second step a compound of formula (3) is reacted with a suitable aniline of formula (4) to give a compound of formula (I).

This coupling reaction can be carried out in an alcohol like 1-butanol or in an inert solvent like DMF, THF, DME, dioxane or mixtures of such solvents in the presence of an acid like hydrogen chloride or 4-methylbenzenesulfonic acid. Preferably, the reaction is carried out at a elevated temperatures, for example 140° C.

Alternatively, a compound of formula (I) is accessable by Palladium-catalyzed C—N cross-coupling reactions of a compound of formula (3) and an aniline of formula (4) (see schemes 2, 3 and 4 and for a review on C—N cross coupling reactions see for example: a) L. Jiang, S. L. Buchwald in 'Metal-Catalyzed Cross-Coupling Reactions', $2^{nd}$ ed.: A. de Meijere, F. Diederich, Eds.: Wiley-VCH: Weinheim, Germany, 2004).

Preferred is the use of suitable palladium precatalysts based upon biarylmonphosphines that are easily activated and ensure the formation of the active mono-ligated Pd(0) complex (see for examples a) S. L. Buchwald et al, J. Am. Chem. Soc. 2008, 130, 6686; b) S. L. Buchwald et al, J. Am. Chem. Soc. 2008, 130, 13552). The reactions are run in the presence of a weak base at elevated temperatures (see for example: a) S. L: Buchwald et al, Tet. Lett. 2009, 50, 3672).

Most preferred is the herein described use of chloro(2-dicyclohexylphosphino-2',4',6'-tri-iso-propyl-1,1'-biphenyl)[2-(2-aminoethyl)phenyl]palladium(II) methyl-tert-butylether adduct, 2-dicyclohexylphosphino-2',4',6'-triisopropylbiphenyl and potassium phosphate in toluene and 1-methylpyrrolidin-2-one. The reactions are preferably run under argon for 3 hours at 130° C. in a microwave oven or in an oil bath.

The syntheses of the disubstituted 5-fluoro-pyrimidines of formula (13) according to the present invention can also be carried out according to the general synthetic sequence, shown in scheme 2.

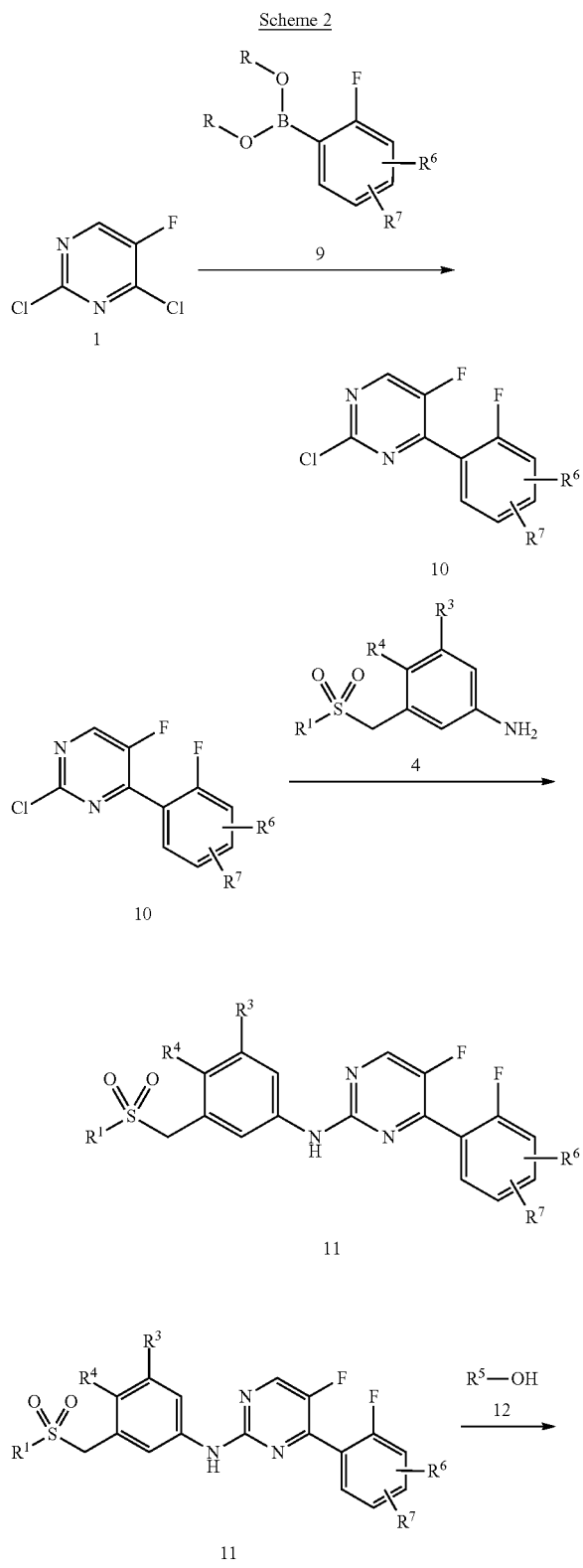

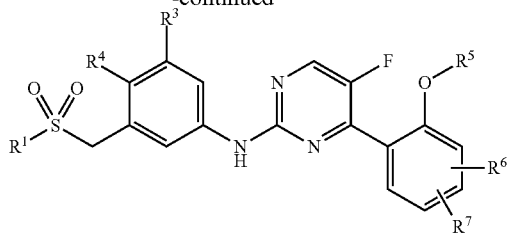

In the first step 2,4-dichloro-5-fluoropyrimidine (1) is reacted with a boronic acid derivative of formula (9) to give a compound of formula (10). The boronic acid derivative (9) may be a boronic acid (R=—H) or an ester of the boronic acid, e.g. its isopropyl ester (R=—CH(CH$_3$)$_2$), preferably an ester derived from pinacol in which the boronic acid intermediate forms a 2-aryl-4,4,5,5-tetramethyl-1,3,2-dioxaborolane (R—R=—C(CH$_3$)$_2$—C(CH$_3$)$_2$—). The coupling reaction is catalyzed by Pd catalysts, e.g. by Pd(0) catalysts like tetrakis (triphenylphosphine)palladium(0) [Pd(PPh$_3$)$_4$], tris(dibenzylideneacetone)di-palladium(0) [Pd$_2$(dba)$_3$], or by Pd(II) catalysts like dichlorobis(triphenylphosphine)-palladium(II) [Pd(PPh$_3$)$_2$Cl$_2$], palladium(II) acetate and triphenylphosphine or by [1,1'-bis(diphenylphosphino)ferrocene]palladium dichloride [Pd(dppf)Cl$_2$]. The reaction is preferably carried out in a mixture of a solvent like 1,2-dimethoxyethane, dioxane, DMF, DME, THF, or isopropanol with water and in the presence of a base like aqueous potassium carbonate, aqueous sodium bicarbonate or potassium phosphate.

In the second step, a compound of formula (10) is reacted with a suitable aniline of formula (4) to give the corresponding cross-coupling product of formula (11). The compounds of formula (11) can be prepared by Palladium-catalyzed C—N cross-coupling reactions (for a review on C—N cross-coupling reactions see for example: a) L. Jiang, S. L. Buchwald in 'Metal-Catalyzed Cross-Coupling Reactions', 2$^{nd}$ ed.: A. de Meijere, F. Diederich, Eds.: Wiley-VCH: Weinheim, Germany, 2004).

Preferred is the use of suitable palladium precatalysts based upon biarylmonphosphines that are easily activated and ensure the formation of the active mono-ligated Pd(0) complex (see for examples a) S. L. Buchwald et al, J. Am. Chem. Soc. 2008, 130, 6686; b) S. L. Buchwald et al, J. Am. Chem. Soc. 2008, 130, 13552). The reactions are run in the presence of a weak base at elevated temperatures (see for example: a) S. L: Buchwald et al, Tet. Lett. 2009, 50, 3672). Most preferred is the herein described use of chloro(2-dicyclohexylphosphino-2',4',6'-tri-iso-propyl-1,1'-biphenyl)[2-(2-aminoethyl)phenyl]palladium(II) methyl-tert-butylether adduct, 2-dicyclohexylphosphino-2',4',6'-triisopropylbiphenyl and potassium phosphate in toluene and 1-methylpyrrolidin-2-one. The reactions are preferably run under argon for 3 hours at 130° C. in a microwave oven or in an oil bath.

In the third step, the ortho-fluoro substituent in 4-position of the compound of formula (11) is replaced by a suitable alkoxy group —OR$^5$. The reaction is preferably carried out by adding at least two equivalents of sodium hydride to a solution of compound (11) and the respective alcohol (12) in DMF at room temperature to give the desired sulfones of formula (13).

Preparation of Compounds

Abbreviations Used in the Description of the Chemistry and in the Examples that Follow are:

CDCl$_3$ (deuterated chloroform); cHex (cyclohexane); d (doublet); DCM (dichloromethane); DIPEA (di-iso-propylethylamine); DME (1,2-dimethoxyethane), DMF (dimethylformamide); DMSO (dimethyl sulfoxide); eq (equivalent); ES (electrospray); EtOAc (ethyl acetate); EtOH (ethanol); iPrOH (iso-propanol); mCPBA (meta-chloroperoxybenzoic acid), MeCN (acetonitrile), MeOH (methanol); MS (mass spectrometry); NBS (N-bromosuccinimide), NMR (nuclear magnetic resonance); p (pentet); Pd(dppf)Cl$_2$ ([1,1'-bis(diphenylphosphino)ferrocene]dichloro palladium(II) complex with dichloromethane); iPrOH (iso-propanol); q (quartet); RT (room temperature); s (singlet); sat. aq. (saturated aqueous); SiO$_2$ (silica gel); TFA (trifluoroacetic acid); TFAA (trifluoroacetic anhydride), THF (tetrahydrofuran); tr (triplet).

The IUPAC names of the examples were generated using the program 'ACD/Name batch version 12.01' from ACD LABS.

Example 1

5-Fluoro-4-(4-fluoro-2-methoxyphenyl)-N-{3 [(methylsulfonyl)methyl]phenyl}pyrimidin-2-amine

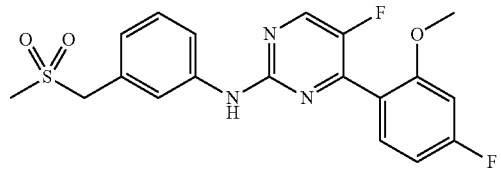 [SMILES: COc1cc(F)ccc1-c1nc(Nc2cccc(CS(C)(=O)=O)c2)ncc1F]

Preparation of Intermediate 1.1

1-[(Methylsulfanyl)methyl]-3-nitrobenzene

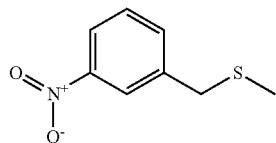

Sodium methanethiolate (13.5 g; 192 mmol) was added in two portions to a stirred solution of 1-(chloromethyl)-3-nitrobenzene (30.0 g; 175 mmol) in ethanol (360 mL) at −15° C. The cold bath was removed and the batch was stirred at room temperature for 3 hours. The batch was diluted with brine and extracted with ethyl acetate (2×). The combined organic phases were washed with water, dried (sodium sulfate), filtered and concentrated to give the desired product (32.2 g) that was used without further purification.

$^1$H NMR (400 MHz, CDCl$_3$, 300K) δ=8.18 (m, 1H), 8.11 (m, 1H), 7.66 (m, 1H), 7.50 (m, 1H), 3.75 (s, 2H), 2.01 (s, 3H).

Preparation of Intermediate 1.2

1-[(Methylsulfonyl)methyl]-3-nitrobenzene

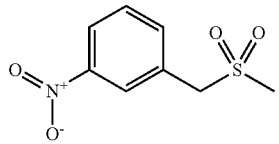

3-Chlorobenzenecarboperoxoic acid (77%; 26.9 g; 120 mmol) was added to a stirred solution of 1-[(methylsulfanyl)methyl]-3-nitrobenzene (10.0 g) in DCM (1305 mL) at 0° C. The batch was stirred at 0° C. for 30 minutes and then 2.5 hours at room temperature. The batch was diluted with water (300 mL) before sodium bicarbonate (11.0 g) was added. The batch was extracted with DCM (2×). The combined organic phases were filtered using a Whatman filter and concentrated. The residue was purified by chromatography (DCM/ethanol 95:5) and finally recrystallized from ethyl acetate to give the desired product (6.2 g; 28.9 mmol).

$^1$H NMR (400 MHz, d$_6$-DMSO, 300K) δ=8.28 (m, 1H), 8.22 (m, 1H), 7.83 (m, 1H), 7.69 (m, 1H), 4.68 (s, 2H), 2.93 (s, 3H).

Preparation of Intermediate 1.3

3-[(Methylsulfonyl)methyl]aniline

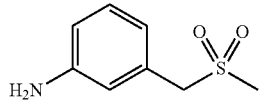

Titanium(III)chloride solution (about 15%) in about 10% hydrochloric acid (162 mL; Merck Schuchardt OHG) was added to a stirred solution of 1-[(methylsulfonyl)methyl]-3-nitrobenzene (5.1 g; 23.8 mmol) in THF (250 mL) at room temperature and the batch was stirred for 16 hours. By adding 1N sodium hydroxide solution the pH value of the reaction mixture was raised to 10 before the batch was extracted with ethyl acetate (2×). The combined organic phases were washed with brine, filtered using a Whatman filter and concentrated to give the desired product (4.5 g) that was used without further purification.

$^1$H NMR (400 MHz, d$_6$-DMSO, 300K) δ=6.97 (m, 1H), 6.51 (m, 3H), 5.13 (br, 2H), 4.23 (s, 2H), 2.83 (s, 3H).

Preparation of Intermediate 1.4

2-Chloro-5-fluoro-4-(4-fluoro-2-methoxyphenyl)pyrimidine

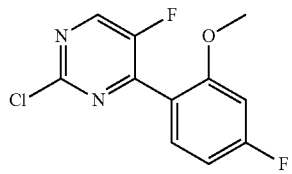 [SMILES: COc1cc(F)ccc1-c1nc(Cl)ncc1F]

A batch with 2,4-dichloro-5-fluoropyrimidine (200 mg; 1.20 mmol; Aldrich Chemical Company Inc.), (4-fluoro-2-methoxyphenyl)boronic acid (224 mg; 1.31 mmol; Aldrich Chemical Company Inc.) and tetrakis(triphenylphosphin) palladium(0) (138 mg; 0.12 mmol) in 1,2-dimethoxyethane (3.6 mL) and 2 M solution of potassium carbonate (1.8 mL) was degassed using argon. The batch was stirred under argon for 16 hours at 90° C. After cooling the batch was diluted with ethyl acetate and washed with brine. The organic phase was filtered using a Whatman filter and concentrated. The residue was purified by column chromatography (hexane/ethyl acetate 1:1) to give the desired product (106 mg; 0.41 mmol).

$^1$H NMR (400 MHz, CDCl$_3$, 300K) δ=8.47 (m, 1H), 7.51 (m, 1H), 6.82 (m, 1H), 6.73 (m, 1H), 3.85 (s, 3H).

Preparation of End Product 4N solution of hydrogen chloride in dioxane (41 μL; 0.16 mmol) was added to a stirred solution of 2-chloro-5-fluoro-4-(4-fluoro-2-methoxyphenyl)pyrimidine (42 mg; 0.16 mmol) and 3-[(methylsulfonyl)methyl]aniline (30 mg; 0.16 mmol) in 1-butanol (0.8 mL). The batch was stirred at 100° C. for 27 hours before the temperature was raised to 140° C. The batch was stirred at this temperature for additional 22 hours. After cooling the batch was concentrated and the residue was purified by preparative HPLC to give the desired product (15 mg; 0.04 mmol).

| System: | Waters Autopurificationsystem: Pump 254, Sample Manager 2767, CFO, DAD 2996, ELSD 2424, SQD 3001 |
|---|---|
| Column: | XBrigde C18 5 μm 100 × 30 mm |
| Solvent: | A = H$_2$O + 0.1% HCOOH |
| | B = MeCN |
| Gradient: | 0-1 min 50% B, 1-8 min 50-90% B |
| Flow: | 50 mL/min |
| Temperatuer: | RT |
| Detection: | DAD scan range 210-400 nm |
| | MS ESI+, ESI−, scan range 160-1000 m/z |
| | ELSD |
| Retention: | 6.2-6.6 min |

$^1$H NMR (400 MHz, d$_6$-DMSO, 300K) δ=9.83 (m, 1H), 8.51 (m, 1H), 7.69 (m, 2H), 7.50 (m, 1H), 7.25 (m, 1H), 7.08 (m, 1H), 6.91 (m, 2H), 4.37 (s, 2H), 3.80 (s, 3H), 2.86 (s, 3H).

Alternative Procedure for the Preparation of End Product

A batch with 3-[(methylsulfonyl)methyl]aniline (108 mg; 0.58 mmol), 2-chloro-5-fluoro-4-(4-fluoro-2-methoxyphenyl)pyrimidine (150 mg; 0.58 mmol), tris(dibenzylideneacetone)dipalladium(0) (96 mg; 0.11 mmol), 4,5-bis(diphenylphosphino)-9,9-dimethylxanthene (88 mg; 0.15 mmol) and cesium carbonate (800 mg; 2.46 mmol) in dioxane (1.0 mL) was degassed using argon. The batch was stirred under argon for 150 minutes at 100° C. After cooling, the batch was filtered and the filter was rinsed with DCM and ethyl acetate. The filtrate was concentrated in vacuo and the residue was purified by preparative HPLC to give the desired product (49 mg; 0.12 mmol).

Example 2

4-[2-(Benzyloxy)-4-fluorophenyl]-5-fluoro-N-{3-[(methylsulfonyl)methyl]phenyl}pyrimidin-2-amine

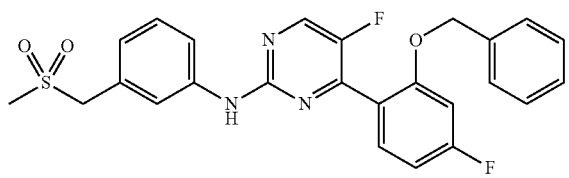 [SMILES: CS(=O)(=O)Cc1cccc(Nc2ncc(F)c(-c3ccc(F)cc3OCc3ccccc3)n2)c1]

Preparation of Intermediate 2.1

4-[2-(Benzyloxy)-4-fluorophenyl]-2-chloro-5-fluoro-pyrimidine

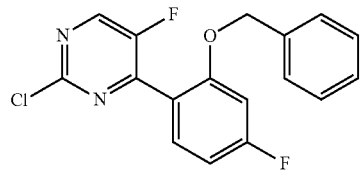 [SMILES: Fc1ccc(-c2nc(Cl)ncc2F)c(OCc2ccccc2)c1]

Intermediate 2.1. was prepared under similar conditions as described in the preparation of Intermediate 1.4. using 2,4-dichloro-5-fluoropyrimidine (Aldrich Chemical Company Inc.) and [2-(benzyloxy)-4-fluorophenyl]boronic acid (ABCR GmbH & CO. KG). The batch was purified by column chromatography (hexane/ethyl acetate 1:1).

$^1$H NMR (400 MHz, CDCl$_3$, 300K) δ=8.44 (m, 1H), 7.54 (m, 1H), 7.35 (m, 5H), 6.83 (m, 1H), 6.79 (m, 1H), 5.11 (s, 2H).

Preparation of End Product 4N solution of hydrogen chloride in dioxane (0.11 mL; 0.45 mmol) was added to a stirred solution of 4-[2-(benzyloxy)-4-fluorophenyl]-2-chloro-5-fluoropyrimidine (150 mg; 0.45 mmol) and 3-[(methylsulfonyl)methyl]aniline (84 mg; 0.45 mmol) in 1-butanol (1.0 mL). The batch was stirred at 140° C. for 20 hours. Additional 3-[(methylsulfonyl)methyl]aniline (84 mg; 0.45 mmol) was added and the batch was stirred at 140° C. for further 60 hours. After cooling the batch was diluted with ethyl acetate and sodium bicarbonate solution. The organic phase was filtered using a Whatman filter and concentrated. The residue was purified by preparative HPLC to give the desired product (64 mg; 0.13 mmol).

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = H$_2$O + 0.1% HCOOH |
| | B = MeCN |

| | |
|---|---|
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO or DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.29 (m, 1H), 7.81 (m, 1H), 7.53 (m, 2H), 7.34 (m, 6H), 7.20 (br, 1H), 7.05 (m, 1H), 6.81 (m, 2H), 5.13 (s, 2H), 4.22 (s, 2H), 2.74 (s, 3H).

Example 3

4-[2-(Benzyloxy)-4-fluorophenyl]-5-fluoro-N-(3-{[(2-methoxyethyl)sulfonyl]methyl}phenyl)pyrimidin-2-amine

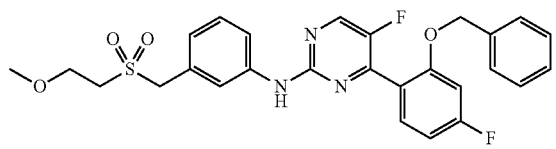 [SMILES: COCCS(=O)(=O)Cc1cccc(Nc2ncc(F)c(-c3ccc(F)cc3OCc3ccccc3)n2)c1]

4N solution of hydrogen chloride in dioxane (0.11 mL; 0.45 mmol) was added to a stirred solution of 4-[2-(benzyloxy)-4-fluorophenyl]-2-chloro-5-fluoropyrimidine (150 mg; 0.45 mmol) and 3-{[(2-methoxyethyl)sulfonyl]methyl}aniline (155 mg; 0.68 mmol; UkrOrgSynthesis Ltd.) in 1-butanol (1.0 mL). The batch was stirred at 140° C. for 60 hours. After cooling the batch was diluted with ethyl acetate and sodium bicarbonate solution. The organic phase was filtered using a Whatman filter and concentrated. The residue was purified by preparative HPLC to give the desired product (19 mg; 0.04 mmol).

| | |
|---|---|
| System: | Waters Autopurificationsystem: Pump 2545, Sample Manager 2767, CFO, DAD 2996, ELSD 2424, SQD 3001 |
| Column: | XBrigde C18 5 μm 100 × 30 mm |
| Solvent: | A = H$_2$O + 0.1% HCOOH |
| | B = MeCN |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO or DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.29 (m, 1H), 7.72 (m, 1H), 7.66 (m, 1H), 7.53 (m, 1H), 7.34 (m, 6H), 7.18 (br, 1H), 7.09 (m, 1H), 6.80 (m, 2H), 5.12 (s, 2H), 4.31 (s, 2H), 3.79 (tr, 2H), 3.40 (s, 3H), 3.08 (tr, 2H).

Example 4

4-[2-(Benzyloxy)-4-fluorophenyl]-N-{3-[(tert-butylsulfonyl)methyl]phenyl}-5-fluoropyrimidin-2-amine

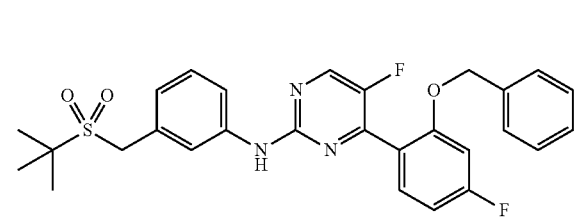 [SMILES: CC(C)(C)S(=O)(=O)Cc1cccc(Nc2ncc(F)c(-c3ccc(F)cc3OCc3ccccc3)n2)c1]

Example 4 was prepared under similar conditions as described in the preparation of Example 3 using 4-[2-(benzyloxy)-4-fluorophenyl]-2-chloro-5-fluoropyrimidine and 3-[(tert-butylsulfonyl)methyl]aniline (UkrOrgSynthesis Ltd.). The batch was purified by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 μm 100 × 30 mm |
| Solvent: | A = H$_2$O + 0.1% HCOOH |
| | B = MeCN |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO or DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.28 (m, 1H), 7.77 (m, 1H), 7.63 (m, 1H), 7.56 (m, 1H), 7.34 (m, 6H), 7.18 (br, 1H), 7.08 (m, 1H), 6.80 (m, 2H), 5.12 (s, 2H), 4.19 (s, 2H), 1.43 (s, 9H).

Example 5

4-[2-(Benzyloxy)-4-fluorophenyl]-5-fluoro-N-{3-[(propan-2-ylsulfonyl)methyl]phenyl}pyrimidin-2-amine

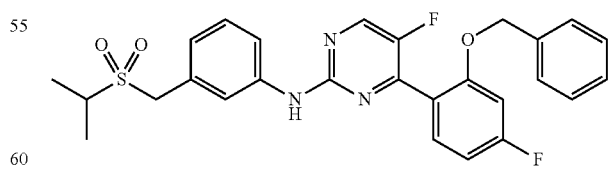

Example 5 was prepared under similar conditions as described in the preparation of Example 3 using 4-[2-(benzyloxy)-4-fluorophenyl]-2-chloro-5-fluoropyrimidine and 3-[(propan-2-ylsulfonyl)methyl]aniline (UkrOrgSynthesis Ltd.). The batch was purified by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 μm 100 × 30 mm |
| Solvent: | A = H$_2$O + 0.1% HCOOH |
| | B = MeCN |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO or DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.29 (m, 1H), 7.81 (m, 1H), 7.55 (m, 2H), 7.34 (m, 6H), 7.22 (br, 1H), 7.06 (m, 1H), 6.81 (m, 2H), 5.12 (s, 2H), 4.21 (s, 2H), 3.03 (m, 1H), 1.34 (d, 6H).

Example 6

4-[2-(Benzyloxy)-4-fluorophenyl]-N-{3-[(cyclohexylsulfonyl)methyl]phenyl}-5-fluoropyrimidin-2-amine

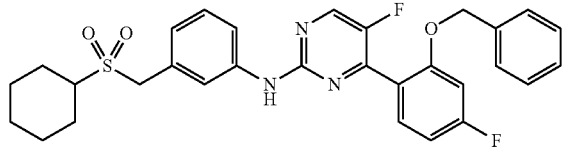 [SMILES: O=S(=O)(Cc1cccc(Nc2ncc(F)c(-c3ccc(F)cc3OCc3ccccc3)n2)c1)C1CCCCC1]

Example 6 was prepared under similar conditions as described in the preparation of Example 3 using 4-[2-(benzyloxy)-4-fluorophenyl]-2-chloro-5-fluoropyrimidine and 3-[(cyclohexylsulfonyl)methyl]aniline (UkrOrgSynthesis Ltd.). The batch was purified by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 μm 100 × 30 mm |
| Solvent: | A = H$_2$O + 0.1% HCOOH |
| | B = MeCN |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO or DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.29 (m, 1H), 7.81 (m, 1H), 7.56 (m, 2H), 7.32 (m, 6H), 7.21 (br, 1H), 7.03 (m, 1H), 6.82 (m, 2H), 5.12 (s, 2H), 4.18 (s, 2H), 2.77 (m, 1H), 2.12 (m, 2H), 1.86 (m, 2H), 1.63 (m, 2H), 1.21 (m, 4H).

Example 7

5-Fluoro-4-(4-fluoro-2-methoxyphenyl)-N-{3-[(propan-2-ylsulfonyl)methyl]phenyl}pyrimidin-2-amine

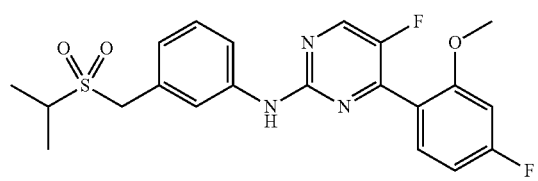 [SMILES: COc1cc(F)ccc1-c1nc(Nc2cccc(CS(=O)(=O)C(C)C)c2)ncc1F]

Preparation of Intermediate 7.1

1-Nitro-3-[(propan-2-ylsulfanyl)methyl]benzene

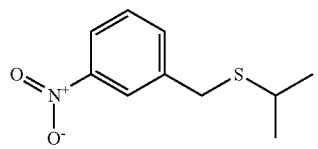

A solution of sodium methoxide (15.5 mL, 25 wt % in methanol) was diluted with methanol (85 mL) and treated with 2-propanethiol (6.3 mL) at room temperature for 60 minutes, cooled to −15° C., treated with 3-nitrobenzylchloride (10 g) in 3 portions, kept for 2 hours at −15° C., then the temperature was increased to room temperature. The reaction mixture was concentrated in vacuo, treated with diethyl ether (300 mL), washed with water (2×100 mL) and brine (100 mL), dried with sodium sulfate and evaporated to dryness. The title compound (12.3 g) was thus obtained and used without further purification.

Preparation of Intermediate 7.2

1-Nitro-3-[(propan-2-ylsulfonyl)methyl]benzene

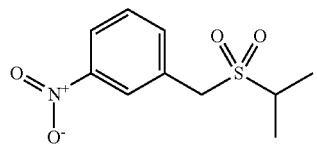 [SMILES: CC(C)S(=O)(=O)Cc1cccc([N+](=O)[O-])c1]

A solution of 1-nitro-3-[(propan-2-ylsulfanyl)methyl]benzene (4.0 g) in DCM (160 mL) was treated at 0° C. with portions of m-chloroperbenzoic acid (9.3 g, 77%). The mixture was stirred at 0° C. for further 30 minutes and then 18 hours at room temperature. The reaction mixture was diluted with DCM before sodium hydrogen sulfite and sodium bicarbonate solution was added and extracted with DCM (2×). The combined organic phases were washed and concentrated. The residue was purified by chromatography (hexane/ethyl acetate 12%-100%) to give the title compound (4.5 g).

Preparation of Intermediate 7.3

N-{3-[(Propan-2-ylsulfonyl)methyl]phenyl}acetamide

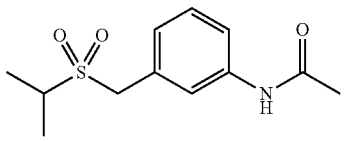 [SMILES: CC(=O)Nc1cccc(CS(=O)(=O)C(C)C)c1]

A suspension of crude 1-nitro-3-[(propan-2-ylsulfonyl)methyl]benzene (5.0 g) in acetic acid (58 mL) was treated with iron powder (4.7 g), heated for 22 hours at 110° C. bath temperature and cooled to room temperature. Then water (250 mL) and DCM (250 mL) were added, stirred, filtered, dried with sodium sulfate, filtered and concentrated. An analytical sample (200 mg) of the crude title compound (5.6 g) was recrystallized from diethyl ether/ethanol (121 mg). Lit.: [Grohmann and Hathaway, Molbank 2006, M502].

$^1$H-NMR (600 MHz, CDCl$_3$): δ=7.61 (s, 1H), 7.50 (d, 1H), 7.37 (br. s., 1H), 7.32 (t, 1H), 7.14 (d, 1H), 4.20 (s, 2H), 3.05 (spt, 1H), 2.16 (s, 3H), 1.39 (d, 6H).

Preparation of Intermediate 7.4

3-[(Propan-2-ylsulfonyl)methyl]anilinium chloride

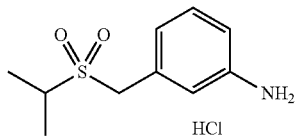

A solution of N-{3-[(propan-2-ylsulfonyl)methyl]phenyl}acetamide (5.4 g) in ethanol (29.6 mL) was treated with concentrated hydrochloric acid (35.5 mL) and refluxed for 24 hours. The reaction mixture was condensed to dryness. The title compound (3.5 g) was obtained by crystallization from ethanol/ethyl acetate.

$^1$H-NMR (400 MHz, d$_6$-DMSO): δ=9.95 (br. s., 2H), 7.47 (m, 1H), 7.34 (m, 3H), 4.52 (s, 2H), 3.22 (spt, 1H), 1.29 (d, 6H).

Preparation of End Product

A batch with 2-chloro-5-fluoro-4-(4-fluoro-2-methoxyphenyl)pyrimidine (150 mg; 0.58 mmol) and 3-[(propan-2-ylsulfonyl)methyl]anilinium chloride (146 mg; 0.58 mmol) in 1-butanol (2.9 mL) was stirred at 120° C. for 48 hours. The temperature was raised to 140° C. and the batch was stirred for additional 24 hours. After cooling the batch was concentrated in vacuo. Sodium bicarbonate solution and ethyl acetate were added. The organic phase was washed with sodium chloride solution, dried with sodium sulfate, filtered and concentrated. The residue was purified by chromatography (hexane/ethyl acetate 7%-60%) to give the desired product (214 mg; 0.49 mmol).

$^1$H NMR (400 MHz, CDCl$_3$) δ=8.30 (m, 1H), 7.81 (m, 1H), 7.58 (m, 1H), 7.50 (m, 1H), 7.33 (m, 1H), 7.20 (br, 1H), 7.07 (m, 1H), 6.81 (m, 1H), 6.75 (m, 1H), 4.21 (s, 2H), 3.86 (s, 3H), 3.04 (m, 1H), 1.34 (d, 6H).

Example 8

2-[(3-{[5-Fluoro-4-(4-fluoro-2-methoxyphenyl)pyrimidin-2-yl]amino}benzyl)sulfonyl]ethanol

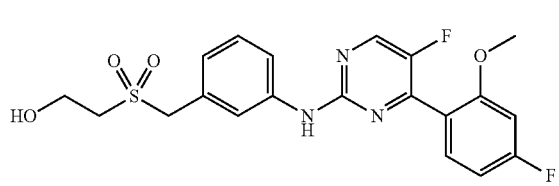 [SMILES: COc1cc(F)ccc1-c1nc(Nc2cccc(CS(=O)(=O)CCO)c2)ncc1F]

Example 8. was prepared under similar conditions as described in the preparation of Example 1 using 2-chloro-5-fluoro-4-(4-fluoro-2-methoxyphenyl)pyrimidine and 2-[(3-aminobenzyl)sulfonyl]ethanol. The batch was purified by chromatography (hexane/ethyl acetate 7%-100%).

$^1$H NMR (400 MHz, CDCl$_3$) δ=8.30 (m, 1H), 7.83 (m, 1H), 7.56 (m, 1H), 7.49 (m, 1H), 7.35 (m, 1H), 7.09 (m, 1H), 6.82 (m, 1H), 6.76 (m, 1H), 4.33 (s, 2H), 4.04 (m, 2H), 3.86 (s, 3H), 3.09 (m, 2H), 2.49 (br, 1H).

Example 9

4-(3,4-Dihydro-2H-chromen-8-yl)-5-fluoro-N-{3-[(methylsulfonyl)methyl]phenyl}pyrimidin-2-amine

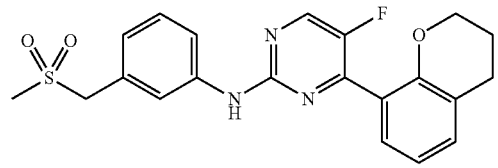 [SMILES: CS(=O)(=O)Cc1cccc(Nc2ncc(F)c(-c3cccc4c3OCCC4)n2)c1]

Preparation of Intermediate 9.1

2-Chloro-4-(3,4-dihydro-2H-chromen-8-yl)-5-fluoropyrimidine

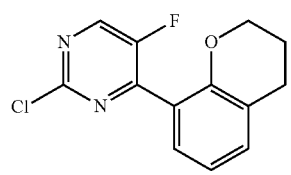 [SMILES: Fc1cnc(Cl)nc1-c1cccc2c1OCCC2]

A batch with 2,4-dichloro-5-fluoropyrimidine (565 mg; 3.28 mmol; Aldrich Chemical Company Inc.), 3,4-dihydro-2H-chromen-8-ylboronic acid (643 mg; 3.61 mmol; Parkway Scientific LLC) and bis(triphenylphosphine)palladium(II) chloride (230 mg; 0.33 mmol) in 1,2-dimethoxyethane (5.4 mL) and 2 M solution of potassium carbonate (4.9 mL) was degassed using argon. The batch was stirred under argon for 16 hours at 90° C. After cooling the batch was diluted with ethyl acetate and washed with brine. The organic phase dried (sodium sulfate), filtered and concentrated. The residue was purified by chromatography (hexane/ethyl acetate 2%-20%) to give the desired product (701 mg; 2.57 mmol).

$^1$H NMR (400 MHz, CDCl$_3$, 300K) δ=8.44 (m, 1H), 7.31 (m, 1H), 7.21 (m, 1H), 6.97 (m, 1H), 4.20 (tr, 2H), 2.86 (tr, 2H), 2.04 (m, 2H).

Preparation of End Product

A batch with 3-[(methylsulfonyl)methyl]aniline (40.0 mg; 0.212 mmol), 2-chloro-4-(3,4-dihydro-2H-chromen-8-yl)-5-fluoropyrimidine (72.8 mg; 0.275 mmol), chloro(2-dicyclohexylphosphino-2',4',6'-tri-iso-propyl-1,1'-biphenyl)[2-(2-aminoethyl)phenyl]palladium(II) methyl-tert-butylether adduct (13.1 mg; 0.016 mmol), 2-dicyclohexylphosphino-2',4',6'-triisopropylbiphenyl (7.6 mg; 0.016 mmol) and potassium phosphate (224.6 mg; 1.058 mmol) in toluene (2.7 mL) and 1-methylpyrrolidin-2-one (0.36 mL) was degassed using argon. The batch was stirred under argon for 3 hours at 130° C. in a microwave oven.

After cooling, UPLC-MS analysis of the reaction mixture indicated the desired product.

The reaction was repeated with a second batch using 3-[(methylsulfonyl)methyl]aniline (120.0 mg; 0.635 mmol), 2-chloro-4-(3,4-dihydro-2H-chromen-8-yl)-5-fluoropyrimidine (218.4 mg; 0.825 mmol), chloro(2-dicyclohexylphosphino-2',4',6'-tri-iso-propyl-1,1'-biphenyl)[2-(2-aminoethyl)phenyl]palladium(II) methyl-tert-butylether adduct (39.3 mg; 0.048 mmol), 2-dicyclohexylphosphino-2',4',6'-triisopropylbiphenyl (22.7 mg; 0.048 mmol) and potassium phosphate (673.7 mg; 3.174 mmol) in toluene (8.1 mL) and 1-methylpyrrolidin-2-one (1.0 mL).

Both batches were combined, diluted with water and extracted with ethyl acetate (3×). The combined organic phases were dried (sodium sulfate), filtered and concentrated. The residue was purified by chromatography (hexane/ethyl acetate 12%-100%) to give the desired product (191.0 mg; 0.46 mmol).

$^1$H NMR (400 MHz, DMSO-d$_6$, 300K) δ=9.78 (m, 1H), 8.48 (m, 1H), 7.73 (br, 1H), 7.71 (m, 1H), 7.24 (m, 3H), 6.93 (m, 2H), 4.37 (s, 2H), 4.13 (tr, 2H), 2.86 (s, 3H), 2.80 (tr, 2H), 1.91 (m, 2H).

Example 10

N-{3-[(Cyclopropylsulfonyl)methyl]phenyl}-4-(3,4-dihydro-2H-chromen-8-yl)-5-fluoropyrimidin-2-amine

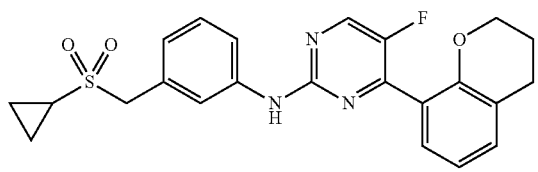 [SMILES: O=S(=O)(Cc1cccc(Nc2ncc(F)c(-c3cccc4c3OCCC4)n2)c1)C1CC1]

Preparation of Intermediate 10.1

1-[(Cyclopropylsulfonyl)methyl]-3-nitrobenzene

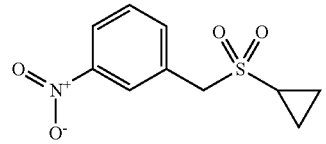 [SMILES: O=[N+]([O-])c1cccc(CS(=O)(=O)C2CC2)c1]

Sodium cyclopropanesulfinate (1.04 g; 8.1 mmol) was added to a solution of 1-(bromomethyl)-3-nitrobenzene (1.17 g; 5.4 mmol) in acetonitrile (50 mL) at room temperature. The batch was stirred at 90° C. for 4 hours. After cooling, the batch was diluted with water and extracted with DCM (2×). The combined organic phases were filtered using a Whatman filter and concentrated to give the desired product (1.26 g; 5.2 mmol) that was used without further purifications.

$^1$H NMR (400 MHz, CDCl$_3$, 300K) δ=8.28 (m, 2H), 7.81 (m, 1H), 7.61 (m, 1H), 4.37 (s, 2H), 2.29 (m, 1H), 1.20 (m, 2H), 1.03 (m, 2H).

Preparation of Intermediate 10.2

3-[(Cyclopropylsulfonyl)methyl]aniline

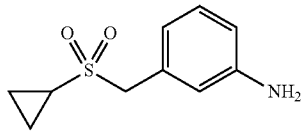 [SMILES: Nc1cccc(CS(=O)(=O)C2CC2)c1]

Intermediate 10.2. was prepared under similar conditions as described in the preparation of Intermediate 1.3. using 1-[(cyclopropylsulfonyl)methyl]-3-nitrobenzene and titanium(III)chloride solution (about 15%) in about 10% hydrochloric acid (Merck Schuchardt OHG). The batch was purified by chromatography (DCM/EtOH 95:5).

$^1$H NMR (400 MHz, CDCl$_3$, 300K) δ=7.15 (m, 1H), 6.77 (m, 2H), 6.60 (m, 1H), 4.16 (s, 2H), 3.65 (br, 2H), 2.23 (m, 1H), 1.15 (m, 2H), 0.93 (m, 2H),

Preparation of End Product

Example 10 was prepared under similar conditions as described in the preparation of Example 9 using 2-chloro-4-(3,4-dihydro-2H-chromen-8-yl)-5-fluoropyrimidine, 3-[(cyclopropylsulfonyl)methyl]aniline, chloro(2-dicyclohexylphosphino-2',4',6'-tri-iso-propyl-1,1'-biphenyl)[2-(2-aminoethyl)phenyl]palladium(II) methyl-tert-butylether adduct, 2-dicyclohexylphosphino-2',4',6'-triisopropylbiphenyl and potassium phosphate. The batch was purified by preparative HPLC.

| System: | Waters Autopurificationsystem: Pump 2545, Sample Manager 2767, CFO, DAD 2996, ELSD 2424, SQD 3001 |
|---|---|
| Column: | XBrigde C18 5 µm 100 × 30 mm |
| Solvent: | A = H$_2$O + 0.1% HCOOH |
| | B = Acetonitrile |

| | |
|---|---|
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.28 (m, 1H), 7.85 (m, 1H), 7.56 (m, 1H), 7.30 (m, 3H), 7.19 (m, 1H), 7.07 (m, 1H), 6.96 (m, 1H), 4.24 (s, 2H), 4.22 (tr, 2H), 2.88 (tr, 2H), 2.21 (m, 1H), 2.05 (m, 2H), 1.11 (m, 2H), 0.87 (m, 2H).

Example 11

4-[2-(Benzyloxy)-4-fluorophenyl]-5-fluoro-N-{3-fluoro-5-[(methylsulfonyl)methyl]phenyl}pyrimidin-2-amine

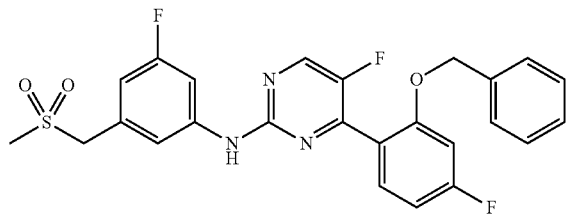 [SMILES: CS(=O)(=O)Cc1cc(F)cc(Nc2ncc(F)c(-c3ccc(F)cc3OCc3ccccc3)n2)c1]

Preparation of Intermediate 11.1

1-Fluoro-3-[(methylsulfanyl)methyl]-5-nitrobenzene

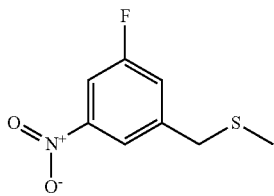

Sodium methanethiolate (1.22 g; 17.4 mmol) was added in three portions to a stirred solution of 1-(chloromethyl)-3-fluoro-5-nitrobenzene (3.00 g; 15.8 mmol, HE Chemical) in ethanol (33 mL) at 0° C. The ice bath was removed and the batch was stirred at room temperature for 18 hours. Further sodium methanethiolate (0.33 g; 4.7 mmol) was added and the batch was stirred for 5 additional hours at room temperature. The batch was diluted with brine and extracted with ethyl acetate (2×). The combined organic phases were washed with water, dried (sodium sulfate), filtered and concentrated to give the desired product (3.4 g) that was used without further purification.

$^1$H NMR (400 MHz, CDCl$_3$, 300K) δ=8.00 (m, 1H), 7.81 (m, 1H), 7.42 (m, 1H), 3.74 (s, 2H), 2.02 (s, 3H).

Preparation of Intermediate 11.2

1-Fluoro-3-[(methylsulfonyl)methyl]-5-nitrobenzene

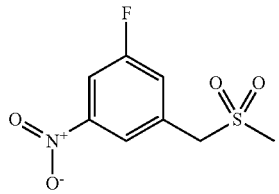

3-Chlorobenzenecarboperoxoic acid (77%; 3.68 g; 16.4 mmol) was added to a stirred solution of 1-fluoro-3-[(methylsulfanyl)methyl]-5-nitrobenzene (1.50 g) in DCM (178 mL) at 0° C. The batch was stirred at 0° C. for 30 minutes and then 2.5 hours at room temperature. The batch was diluted with water (450 mL) before sodium bicarbonate (1.50 g) was added. The batch was extracted with DCM (2×). The combined organic phases were filtered using a Whatman filter and concentrated to give the crude product (3.33 g) that was used without further purification.

Preparation of Intermediate 11.3

3-Fluoro-5-[(methylsulfonyl)methyl]aniline

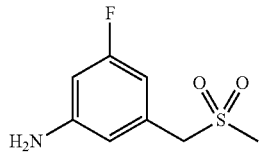

Titanium(III)chloride solution (about 15%) in about 10% hydrochloric acid (29 mL, Merck Schuchardt OHG) was added to a stirred solution of crude 1-fluoro-3-[(methylsulfonyl)methyl]-5-nitrobenzene (1.00 g) in THF (45 mL) at room temperature and the batch was stirred for 16 hours. The batch was cooled with an ice bath while 1N sodium hydroxide solution was added to raise the pH value of the reaction mixture to 8-9. It was stirred for 30 minutes at this temperature before the batch was extracted with ethyl acetate (2×). The combined organic phases were washed with brine, filtered using a Whatman filter and concentrated. The residue was purified by column chromatography (hexane/ethyl acetate 1:1 to ethyl acetate) to give the desired product (262 mg; 1.29 mmol).

$^1$H NMR (400 MHz, CDCl$_3$, 300K) δ=6.48 (m, 2H), 6.39 (m, 1H), 4.11 (s, 2H), 3.88 (br, 2H), 2.79 (s, 3H).

Preparation of End Product

Example 11 was prepared under similar conditions as described in the preparation of Example 1 using 4-[2-(benzyloxy)-4-fluorophenyl]-2-chloro-5-fluoropyrimidine and 3-fluoro-5-[(methylsulfonyl)methyl]aniline. The batch was purified by preparative HPLC.

| | |
|---|---|
| System: | Waters Autopurificationsystem: Pump 254, Sample Manager 2767, CFO, DAD 2996, ELSD 2424, SQD 3001 |
| Column: | XBrigde C18 5 µm 100 × 30 mm |
| Solvent: | A = H$_2$O + 0.1% HCOOH |
| | B = MeCN |
| Gradient: | 0-1 min 50% B, 1-8 min 50-90% B, 8-8.1 min 90-100% B, 8.1-10 min 100% B |
| Flow: | 50 mL/min |
| Temperature: | RT |
| Detection: | DAD scan range 210-400 nm |
| | MS ESI+, ESI−, scan range 160-1000 m/z |
| | ELSD |
| Retention: | 5.0-5.3 min |

$^1$H NMR (400 MHz, CDCl$_3$, 300K) δ=8.32 (m, 1H), 7.67 (m, 1H), 7.51 (m, 1H), 7.32 (m, 7H), 6.80 (m, 3H), 5.13 (s, 2H), 4.19 (s, 2H), 2.78 (s, 3H).

Example 12

5-Fluoro-4-(4-fluoro-2-methoxyphenyl)-N-{3-fluoro-5-[(methylsulfonyl)methyl]phenyl}pyrimidin-2-amine

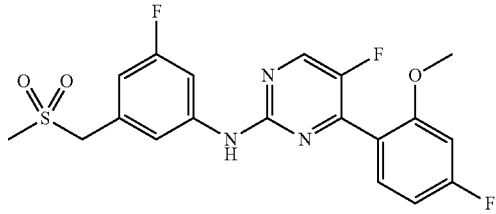 [SMILES: COc1cc(F)ccc1-c1nc(Nc2cc(F)cc(CS(C)(=O)=O)c2)ncc1F]

Example 12 was prepared under similar conditions as described in the preparation of Example 1 using 2-chloro-5-fluoro-4-(4-fluoro-2-methoxyphenyl)pyrimidine and 3-fluoro-5-[(methylsulfonyl)methyl]aniline. The batch was purified by preparative HPLC.

| | |
|---|---|
| System: | |
| Column: | Waters Autopurificationsystem: Pump 254, Sample Manager 2767, CFO, DAD 2996, ELSD 2424, SQD 3001 |
| Solvent: | XBrigde C18 5 µm 100 × 30 mm |
| | A = H$_2$O + 0.2% NH$_3$ |
| Gradient: | B = MeOH |
| Flow: | 0-1 min 50% B, 1-8 min 50-90% B, 8-8.1 min 90-100% B, 8.1-10 min 100% B |
| Temperature: | 50 mL/min |
| Detection: | DAD scan range 210-400 nm |
| | MS ESI+, ESI−, scan range 160-1000 m/z |
| | ELSD |
| Retention: | 5.5-6.2 min |

$^1$H NMR (400 MHz, CDCl$_3$, 300K) δ=8.33 (m, 1H), 7.72 (m, 1H), 7.48 (m, 1H), 7.31 (m, 2H), 6.78 (m, 3H), 4.20 (s, 2H), 3.87 (s, 3H), 2.80 (s, 3H).

Example 13

4-(2,3-Dihydro-1,4-benzodioxin-5-yl)-5-fluoro-N-{3-[(methylsulfonyl)methyl]phenyl}pyrimidin-2-amine

Preparation of Intermediate 13.1

2-Chloro-4-(2,3-dihydro-1,4-benzodioxin-5-yl)-5-fluoro-pyrimidine

Intermediate 13.1 was prepared under similar conditions as described in the preparation of Intermediate 9.1 using 2,4-dichloro-5-fluoropyrimidine (Aldrich Chemical Company Inc.) and 2,3-dihydro-1,4-benzodioxin-5-ylboronic acid (Combi-Blocks Inc.).

$^1$H-NMR (400 MHz, DMSO-d$_6$, 300K): δ [ppm]=8.94 (d, 1H), 7.12-7.07 (m, 1H), 7.07-6.97 (m, 2H), 4.33-4.25 (m, 4H).

Preparation of End Product

Example 13 was prepared under similar conditions as described in the preparation of Example 9 using 2-chloro-4-(2,3-dihydro-1,4-benzodioxin-5-yl)-5-fluoropyrimidine, 3-[(methylsulfonyl)methyl]aniline (Intermediate 1.3), chloro(2-dicyclohexylphosphino-2',4',6'-tri-iso-propyl-1,1'-biphenyl)[2-(2-aminoethyl)phenyl]palladium(II) methyl-tert-butylether adduct, 2-dicyclohexylphosphino-2',4',6'-triisopropylbiphenyl and potassium phosphate. The batch was purified by preparative HPLC.

$^1$H NMR (400 MHz, DMSO-d$_6$, 300K) δ [ppm]=9.86 (s, 1H), 8.56 (d, 1H), 7.78-7.73 (m, 2H), 7.32-7.26 (m, 1H), 7.07-7.02 (m, 2H), 7.02-6.96 (m, 2H), 4.41 (s, 2H), 4.32-4.25 (m, 4H), 2.89 (s, 3H).

Example 14

N-{3-[(Cyclopropylsulfonyl)methyl]phenyl}-5-fluoro-4-(4-fluoro-2-methoxyphenyl)pyrimidin-2-amine

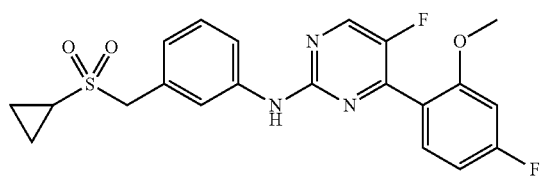 [SMILES: COc1cc(F)ccc1-c1nc(Nc2cccc(CS(=O)(=O)C3CC3)c2)ncc1F]

Preparation of End Product

Example 14 was prepared under similar conditions as described in the preparation of Example 9 using 2-chloro-5-fluoro-4-(4-fluoro-2-methoxyphenyl)pyrimidine (Intermediate 1.4), 3-[(cyclopropylsulfonyl)methyl]aniline (Intermediate 10.2), chloro(2-dicyclohexylphosphino-2',4',6'-tri-isopropyl-1,1'-biphenyl)[2-(2-aminoethyl)phenyl]palladium (II) methyl-tert-butylether adduct, 2-dicyclohexylphosphino-2',4',6'-triisopropylbiphenyl and potassium phosphate. The batch was purified by preparative HPLC.

$^1$H NMR (400 MHz, DMSO-d$_6$, 300K) δ [ppm]=9.85 (s, 1H), 8.55 (d, 1H), 7.80 (d, 1H), 7.72 (dd, 1H), 7.55 (dd, 1H), 7.28 (t, 1H), 7.12 (dd, 1H), 7.00 (d, 1H), 6.95 (td, 1H), 4.42 (s, 2H), 3.84 (s, 3H), 2.56-2.52 (m, 1H), 1.02-0.76 (m, 4H).

Example 15

N-{3-[(Benzylsulfonyl)methyl]phenyl}-5-fluoro-4-(4-fluoro-2-methoxyphenyl)-pyrimidin-2-amine

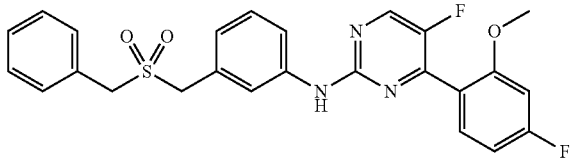 [SMILES: COc1cc(F)ccc1-c1nc(Nc2cccc(CS(=O)(=O)Cc3ccccc3)c2)ncc1F]

Preparation of Intermediate 15.1

1-[(Benzylsulfanyl)methyl]-3-nitrobenzene

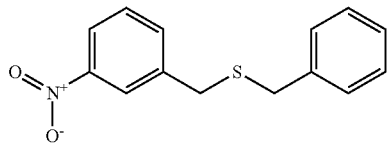 [SMILES: O=[N+]([O-])c1cccc(CSCc2ccccc2)c1]

Sulfur (2.23 g; 67.6 mmol) was added portionswise into a stirred solution of benzylmagnesium bromide in THF (12%; 100.0 ml; 61.4 mmol). The resulting solution was stirred at 50° C. for 1 hour and then cooled to 0° C. Lithium tetrahydridoaluminate (1.28 g; 33.78 mmol) was cautiously added under stirring. The batch was stirred for 30 minutes at 50° C. and cooled to 0° C. again. Water (4 ml) was cautiously added under stirring. Finally, sulfuric acid (5%; 250 ml) was cautiously added and the batch was stirred for 10 minutes. The organic phase was separated and the aqueous phase was extracted with diethyl ether (2×). The combined organic phases were washed with saturated aqueous ammonium chloride solution (2×), aqueous sodium bicarbonate solution (5%, 2×), water (2×) and saturated aqueous sodium chloride solution (2×). The organic phase was dried (Na$_2$SO$_4$) and filtered before it was slowly added to a stirred batch of 1-(chloromethyl)-3-nitrobenzene (5.27 g; 30.7 mmol) and potassium carbonate (6.36 g; 46.1 mmol) in DMF (100 ml). The batch was stirred at 85° C. over night. After cooling, the batch was filtered over celite and concentrated in vacuo.

The residue was dissolved in ethyl acetate and washed with water (2×) and saturated aqueous sodium chloride solution (2×). The organic phase was dried (Na$_2$SO$_4$), filtered and concentrated. The residue was purified by chromatography (hexane/ethyl acetate 8:2) to give the desired product (5.65 g; 20.7 mmol).

$^1$H NMR (400 MHz, d$_6$-DMSO, 300K) δ=8.14-8.06 (m, 2H), 7.76-7.71 (m, 1H), 7.63-7.58 (m, 1H), 7.34-7.19 (m, 5H), 3.83 (s, 2H), 3.69 (s, 2H).

Preparation of Intermediate 15.2

1-[(Benzylsulfonyl)methyl]-3-nitrobenzene

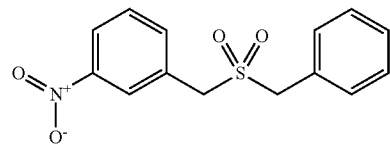 [SMILES: O=[N+]([O-])c1cccc(CS(=O)(=O)Cc2ccccc2)c1]

Intermediate 16.2 was prepared under similar conditions as described in the preparation of Example 1.2 using 1-[(benzylsulfanyl)methyl]-3-nitrobenzene. The batch was purified by chromatography (dichloromethane/ethanol).

$^1$H NMR (400 MHz, d$_6$-DMSO, 300K) δ=8.25-8.18 (m, 2H), 7.80 (d, 1H), 7.70-7.64 (m, 1H), 7.35 (s, 5H), 4.68 (s, 2H), 4.50 (s, 2H).

Preparation of Intermediate 15.3

3-[(Benzylsulfonyl)methyl]aniline

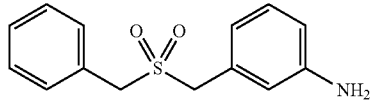 [SMILES: Nc1cccc(CS(=O)(=O)Cc2ccccc2)c1]

Intermediate 16.3 was prepared under similar conditions as described in the preparation of Example 1.3 using 1-[(benzylsulfonyl)methyl]-3-nitrobenzene.

$^1$H NMR (400 MHz, d$_6$-DMSO, 300K) δ=7.39 (d, 5H), 7.01 (t, 1H), 6.59-6.53 (m, 2H), 6.50 (d, 1H), 5.16 (s, 2H), 4.42 (s, 2H), 4.25 (s, 2H).

Preparation of End Product

Example 15 was prepared under similar conditions as described in the preparation of Example 9 using 2-chloro-5- fluoro-4-(4-fluoro-2-methoxyphenyl)pyrimidine (Intermediate 1.4), 3-[(benzylsulfonyl)-methyl]aniline (Intermediate 15.3), chloro(2-dicyclohexylphosphino-2',4',6'-tri-iso-propyl-1,1'-biphenyl)[2-(2-aminoethyl)phenyl]palladium(II) methyl-tert-butylether adduct, 2-dicyclohexylphosphino-2',4',6'-triisopropylbiphenyl and potassium phosphate. The batch was purified by preparative HPLC.

$^1$H NMR (400 MHz, DMSO-$d_6$, 300K) δ [ppm]=9.87 (s, 1H), 8.55 (d, 1H), 7.81-7.71 (m, 2H), 7.53 (dd, 1H), 7.39 (s, 5H), 7.29 (t, 1H), 7.08 (dd, 1H), 6.96 (d, 1H), 6.90 (td, 1H), 4.47 (s, 2H), 4.39 (s, 2H), 3.82 (s, 3H).

Example 16

5-Fluoro-4-[4-fluoro-2-(pyridin-3-ylmethoxy)phenyl]-N-{3-[(methylsulfonyl)methyl]phenyl}pyrimidin-2-amine

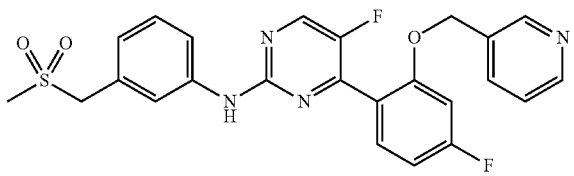 [SMILES: CS(=O)(=O)Cc1cccc(Nc2ncc(F)c(-c3ccc(F)cc3OCc3cccnc3)n2)c1]

Preparation of Intermediate 16.1

2-Chloro-4-(2,4-difluorophenyl)-5-fluoropyrimidine

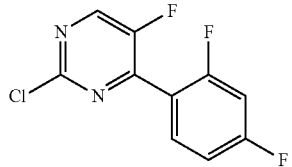 [SMILES: Fc1ccc(-c2nc(Cl)ncc2F)c(F)c1]

Intermediate 16.1 was prepared under similar conditions as described in the preparation of Intermediate 1.4 using 2,4-dichloro-5-fluoropyrimidine (Aldrich Chemical Company Inc.) and (2,4-difluorophenyl)boronic acid (ABCR GmbH & CO. KG).

$^1$H-NMR (300 MHz, CDCl$_3$, 300K): δ [ppm]=8.58 (s, 1H), 7.82-7.67 (m, 1H), 7.17-7.04 (m, 1H), 7.04-6.93 (m, 1H).

Preparation of Intermediate 16.2

4-(2,4-Difluorophenyl)-5-fluoro-N-{3-[(methylsulfonyl)methyl]-phenyl}pyrimidin-2-amine

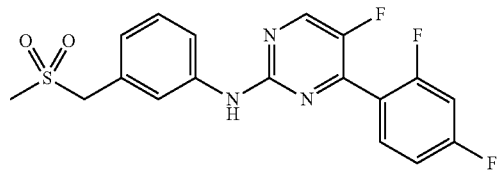 [SMILES: CS(=O)(=O)Cc1cccc(Nc2ncc(F)c(-c3ccc(F)cc3F)n2)c1]

Example 16.2 was prepared under similar conditions as described in the preparation of Example 3. using 2-chloro-4-(2,4-difluorophenyl)-5-fluoropyrimidine (Intermediate 16.1) and 3-[(methylsulfonyl)methyl]aniline (Intermediate 1.3). The batch was purified by preparative HPLC.

$^1$H NMR (400 MHz, DMSO-$d_6$, 300K) δ [ppm]=9.95 (s, 1H), 8.67 (d, 1H), 7.90-7.77 (m, 2H), 7.71 (dd, 1H), 7.47 (ddd, 1H), 7.36-7.27 (m, 2H), 7.01 (d, 1H), 4.42 (s, 2H), 2.90 (s, 3H).

Preparation of End Product 3-(Hydroxymethyl)pyridine (139 mg, 1.27 mmol, ABCR GmbH & CO. KG) was dissolved in DMF (2 ml), sodium hydride (55% suspension in mineral oil, 55 mg, 127 mmol) was added and the mixture was stirred for 30 minutes. 4-(2,4-Difluorophenyl)-5-fluoro-N-{3-[(methylsulfonyl)-methyl]phenyl}-pyrimidin-2-amine (100 mg; 0.25 mmol) was added and the batch was stirred at room temperature for 6 hours. The reaction mixture was added to brine and the batch was extracted with ethyl acetate (2×). The combined organic phases were washed with brine, dried (sodium sulfate), and concentrated. The residue was purified by preparative HPLC to give the desired product (44.3 mg; 91 μmol).

$^1$H-NMR (400 MHz, CDCl$_3$, 300K): δ [ppm]=8.64 (d, 1H), 8.58 (dd, 1H), 8.30 (d, 1H), 7.82 (s, 1H), 7.69 (d, 1H), 7.60-7.52 (m, 2H), 7.35 (t, 1H), 7.30 (dd, 1H), 7.23 (s, 1H), 7.06 (d, 1H), 6.88 (td, 1H), 6.82 (dd, 1H), 5.14 (s, 2H), 4.24 (s, 2H), 2.76 (s, 3H).

Example 17

5-Fluoro-4-{2-fluoro-4-[(4-fluorobenzyl)oxy]phenyl}-N-{3-[(methylsulfonyl)methyl]phenyl}pyrimidin-2-amine

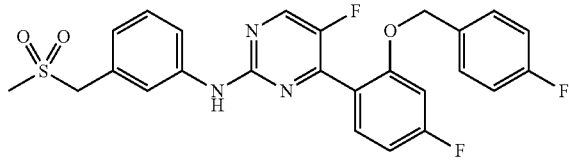 [SMILES: CS(=O)(=O)Cc1cccc(Nc2ncc(F)c(-c3ccc(F)cc3OCc3ccc(F)cc3)n2)c1]

Example 17 was prepared under similar conditions as described in the preparation of Example 16 using 4-(2,4-difluorophenyl)-5-fluoro-N-{3-[(methylsulfonyl)methyl]phenyl}pyrimidin-2-amine (Intermediate 16.2) and (4-fluorophenyl)methanol (ABCR GmbH & CO. KG). The batch was purified by preparative HPLC.

$^1$H-NMR (400 MHz, CDCl$_3$, 300K): δ [ppm]=8.30 (d, 1H), 7.82 (s, 1H), 7.62-7.49 (m, 2H), 7.39-7.30 (m, 3H), 7.21 (s, 1H), 7.10-7.00 (m, 3H), 6.85 (td, 1H), 6.79 (dd, 1H), 5.09 (s, 2H), 4.23 (s, 2H), 2.76 (s, 3H).

Example 18

5-Fluoro-4-{2-fluoro-4-[(3-fluorobenzyl)oxy]phenyl}-N-{3-[(methylsulfonyl)methyl]phenyl}pyrimidin-2-amine

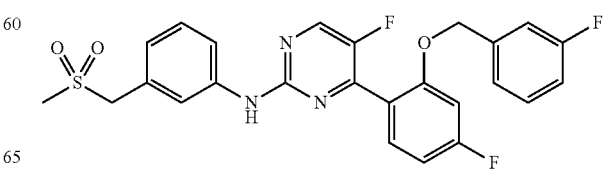

Example 18 was prepared under similar conditions as described in the preparation of Example 16 using 4-(2,4-difluorophenyl)-5-fluoro-N-{3-[(methylsulfonyl)methyl]phenyl}pyrimidin-2-amine (Intermediate 16.2) and (3-fluorophenyl)methanol (ABCR GmbH & CO. KG). The batch was purified by preparative HPLC.

1H-NMR (400 MHz, CDCl$_3$, 300K): δ [ppm]=8.33 (d, 1H), 7.83 (m, 1H), 7.61-7.52 (m, 2H), 7.39-7.29 (m, 2H), 7.26-7.23 (m, 1H), 7.15-6.97 (m, 4H), 6.86 (td, 1H), 6.77 (dd, 1H), 5.12 (s, 2H), 4.24 (s, 2H), 2.76 (s, 3H).

The following Table 1 provides an overview on the compounds described in the example section:

TABLE 1

| Example No. | Structure | Name of compound |
|---|---|---|
| 1 | 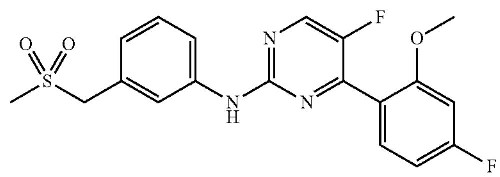 [SMILES: COc1cc(F)ccc1-c1nc(Nc2cccc(CS(C)(=O)=O)c2)ncc1F] | 5-Fluoro-4-(4-fluoro-2-methoxyphenyl)-N-{3-[(methylsulfonyl)methyl]phenyl}pyrimidin-2-amine |
| 2 | 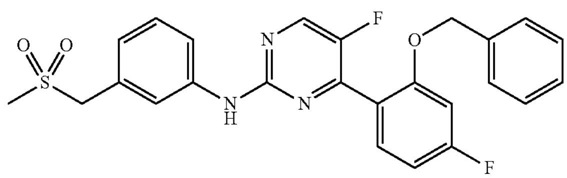 [SMILES: CS(=O)(=O)Cc1cccc(Nc2ncc(F)c(-c3ccc(F)cc3OCc3ccccc3)n2)c1] | 4-[2-(Benzyloxy)-4-fluorophenyl]-5-fluoro-N-{3-[(methylsulfonyl)methyl]phenyl}pyrimidin-2-amine |
| 3 | 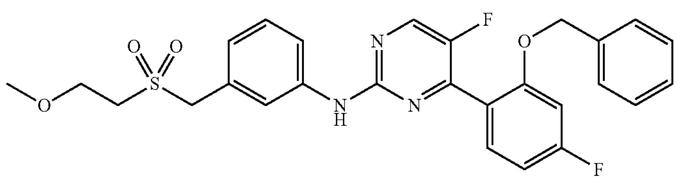 [SMILES: COCCS(=O)(=O)Cc1cccc(Nc2ncc(F)c(-c3ccc(F)cc3OCc3ccccc3)n2)c1] | 4-[2-(Benzyloxy)-4-fluorophenyl]-5-fluoro-N-(3-{[(2-methoxyethyl)sulfonyl]methyl}phenyl)pyrimidin-2-amine |
| 4 | 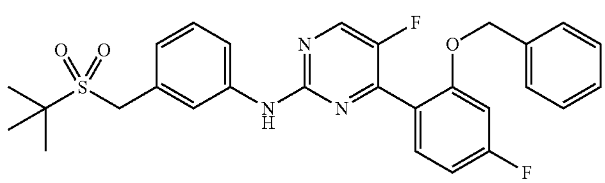 [SMILES: CC(C)(C)S(=O)(=O)Cc1cccc(Nc2ncc(F)c(-c3ccc(F)cc3OCc3ccccc3)n2)c1] | 4-[2-(Benzyloxy)-4-fluorophenyl]-N-{3-[(tert-butylsulfonyl)methyl]phenyl}-5-fluoropyrimidin-2-amine |
| 5 | 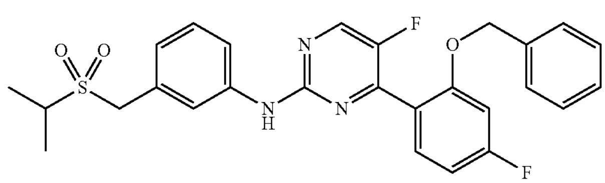 [SMILES: CC(C)S(=O)(=O)Cc1cccc(Nc2ncc(F)c(-c3ccc(F)cc3OCc3ccccc3)n2)c1] | 4-[2-(Benzyloxy)-4-fluorophenyl]-5-fluoro-N-{3-[(propan-2-ylsulfonyl)methyl]phenyl}pyrimidin-2-amine |
| 6 | 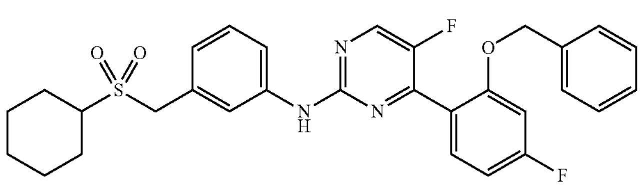 [SMILES: O=S(=O)(Cc1cccc(Nc2ncc(F)c(-c3ccc(F)cc3OCc3ccccc3)n2)c1)C1CCCCC1] | 4-[2-(Benzyloxy)-4-fluorophenyl]-N-{3-[(cyclohexylsulfonyl)methyl]phenyl}-5-fluoropyrimidin-2-amine |
| 7 | 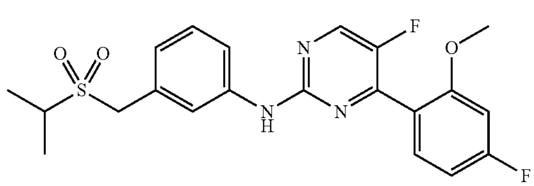 [SMILES: COc1cc(F)ccc1-c1nc(Nc2cccc(CS(=O)(=O)C(C)C)c2)ncc1F] | 5-Fluoro-4-(4-fluoro-2-methoxyphenyl)-N-{3-[(propan-2-ylsulfonyl)methyl]phenyl}pyrimidin-2-amine |

TABLE 1-continued

| Example No. | Structure | Name of compound |
|---|---|---|
| 8 | 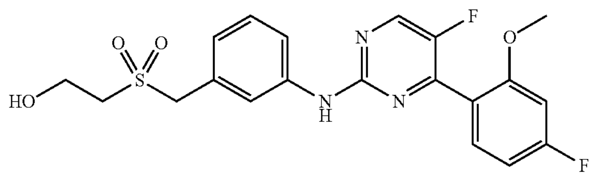 [SMILES: COc1cc(F)ccc1-c1nc(Nc2cccc(CS(=O)(=O)CCO)c2)ncc1F] | 2-[(3-{[5-fluoro-4-(4-fluoro-2-methoxyphenyl)pyrimidin-2-yl]amino}benzyl)sulfonyl]ethanol |
| 9 | 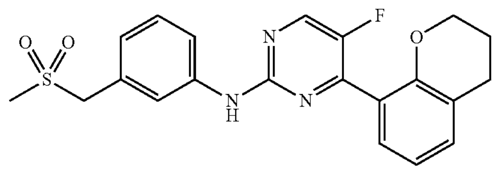 [SMILES: CS(=O)(=O)Cc1cccc(Nc2ncc(F)c(-c3cccc4c3OCCC4)n2)c1] | 4-(3,4-Dihydro-2H-chromen-8-yl)-5-fluoro-N-{3-[(methylsulfonyl)methyl]phenyl}pyrimidin-2-amine |
| 10 | 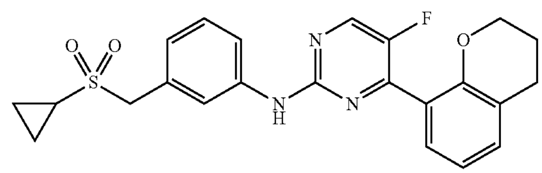 [SMILES: O=S(=O)(Cc1cccc(Nc2ncc(F)c(-c3cccc4c3OCCC4)n2)c1)C1CC1] | N-{3-[(Cyclopropylsulfonyl)methyl]phenyl}-4-(3,4-dihydro-2H-chromen-8-yl)-5-fluoropyrimidin-2-amine |
| 11 | 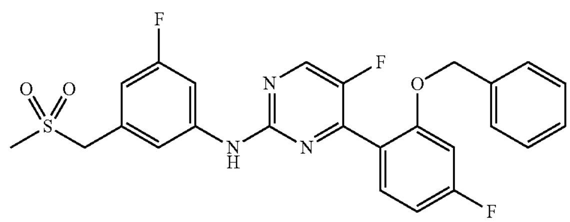 [SMILES: CS(=O)(=O)Cc1cc(F)cc(Nc2ncc(F)c(-c3ccc(F)cc3OCc3ccccc3)n2)c1] | 4-[2-(Benzyloxy)-4-fluorophenyl]-5-fluoro-N-{3-fluoro-5-[(methylsulfonyl)methyl]phenyl}pyrimidin-2-amine |
| 12 | 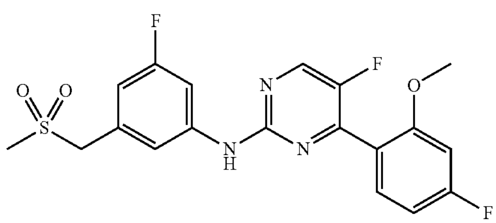 [SMILES: COc1cc(F)ccc1-c1nc(Nc2cc(F)cc(CS(C)(=O)=O)c2)ncc1F] | 5-Fluoro-4-(4-fluoro-2-methoxyphenyl)-N-{3-fluoro-5-[(methylsulfonyl)methyl]phenyl}pyrimidin-2-amine |
| 13 | 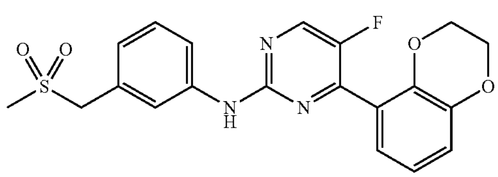 [SMILES: CS(=O)(=O)Cc1cccc(Nc2ncc(F)c(-c3cccc4c3OCCO4)n2)c1] | 4-(2,3-Dihydro-1,4-benzodioxin-5-yl)-5-fluoro-N-{3-[(methylsulfonyl)methyl]phenyl}pyrimidin-2-amine |
| 14 | 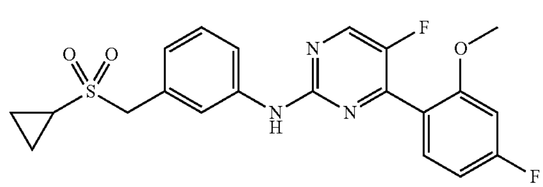 [SMILES: COc1cc(F)ccc1-c1nc(Nc2cccc(CS(=O)(=O)C3CC3)c2)ncc1F] | N-{3-[(Cyclopropylsulfonyl)methyl]phenyl}-5-fluoro-4-(4-fluoro-2-methoxyphenyl)pyrimidin-2-amine |
| 15 | 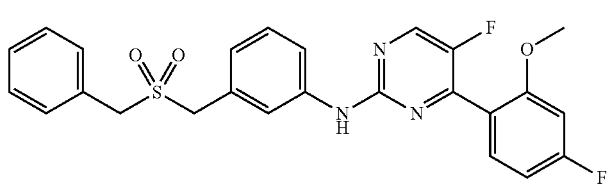 [SMILES: COc1cc(F)ccc1-c1nc(Nc2cccc(CS(=O)(=O)Cc3ccccc3)c2)ncc1F] | N-{3-[(Benzylsulfonyl)methyl]phenyl}-5-fluoro-4-(4-fluoro-2-methoxyphenyl)pyrimidin-2-amine |

TABLE 1-continued

| Example No. | Structure | Name of compound |
|---|---|---|
| 16 | 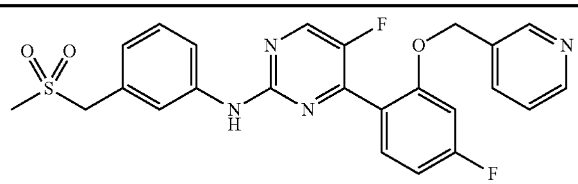 | 5-Fluoro-4-[4-fluoro-2-(pyridin-3-ylmethoxy)phenyl]-N-{3-[(methylsulfonyl)-methyl]phenyl}pyrimidin-2-amine |
| 17 | 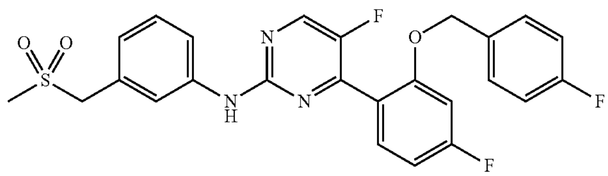 [SMILES: CS(=O)(=O)Cc1cccc(Nc2ncc(F)c(-c3ccc(F)cc3OCc3ccc(F)cc3)n2)c1] | 5-Fluoro-4-{2-fluoro-4-[(4-fluorobenzyl)oxy]phenyl}-N-{3-[(methylsulfonyl)-methyl]phenyl}pyrimidin-2-amine |
| 18 | 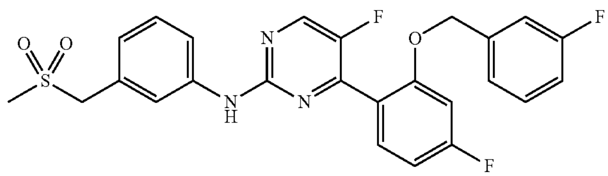 [SMILES: CS(=O)(=O)Cc1cccc(Nc2ncc(F)c(-c3ccc(F)cc3OCc3cccc(F)c3)n2)c1] | 5-Fluoro-4-{2-fluoro-4-[(3-fluorobenzyl)oxy]phenyl}-N-{3-[(methylsulfonyl)-methyl]phenyl}pyrimidin-2-amine |

Results:

TABLE 2

Inhibition for CDK9 and CDK2 of compounds according to the present invention
Table 2

| ① Name of compound | ② | ③ | ④ |
|---|---|---|---|
| 1 5-Fluoro-4-(4-fluoro-2-methoxyphenyl)-N-{3-[(methylsulfonyl)methyl]phenyl}pyrimidin-2-amine | 4 nM | 300 nM | 7 nM |
| 2 4-[2-(Benzyloxy)-4-fluorophenyl]-5-fluoro-N-{3-[(methylsulfonyl)methyl]phenyl}pyrimidin-2-amine | 8 nM | 840 nM | 8 nM |
| 3 4-[2-(Benzyloxy)-4-fluorophenyl]-5-fluoro-N-(3-{[(2-methoxyethyl)sulfonyl]methyl}phenyl)pyrimidin-2-amine | 10 nM | 1200 nM | 10 nM |
| 4 4-[2-(Benzyloxy)-4-fluorophenyl]-N-{3-[(tert-butylsulfonyl)methyl]phenyl}-5-fluoropyrimidin-2-amine | 29 nM | 3100 nM | 80 nM |
| 5 4-[2-(Benzyloxy)-4-fluorophenyl]-5-fluoro-N-{3-[(propan-2-ylsulfonyl)methyl]phenyl}pyrimidin-2-amine | 14 nM | 1600 nM | 20 nM |
| 6 4-[2-(Benzyloxy)-4-fluorophenyl]-N-{3-[(cyclohexylsulfonyl)methyl]phenyl}-5-fluoropyrimidin-2-amine | 51 nM | 20000 nM | 98 nM |
| 7 5-Fluoro-4-(4-fluoro-2-methoxyphenyl)-N-{3-[(propan-2-ylsulfonyl)methyl]phenyl}pyrimidin-2-amine | 13 nM | 510 nM | 120 nM |
| 8 2-[(3-{[5-fluoro-4-(4-fluoro-2-methoxyphenyl)pyrimidin-2-yl]amino}benzyl)sulfonyl]ethanol | 9 nM | 310 nM | 103 nM |
| 9 4-(3,4-Dihydro-2H-chromen-8-yl)-5-fluoro-N-{3-[(methylsulfonyl)methyl]phenyl}pyrimidin-2-amine | 9 nM | 300 nM | 47 nM |
| 10 N-{3-[(Cyclopropylsulfonyl)methyl]phenyl}-4-(3,4-dihydro-2H-chromen-8-yl)-5-fluoropyrimidin-2-amine | 10 nM | 210 nM | 80 nM |
| 11 4-[2-(Benzyloxy)-4-fluorophenyl]-5-fluoro-N-{3-fluoro-5-[(methylsulfonyl)methyl]phenyl}pyrimidin-2-amine | 24 nM | 1100 nM | 40 nM |

TABLE 2-continued

Inhibition for CDK9 and CDK2 of compounds according to the present invention
Table 2

| ① Name of compound | ② | ③ | ④ |
|---|---|---|---|
| 12 5-Fluoro-4-(4-fluoro-2-methoxyphenyl)-N-{3-fluoro-5-[(methylsulfonyl)methyl]phenyl}pyrimidin-2-amine | 6 nM | 200 nM | 16 nM |
| 13 4-(2,3-Dihydro-1,4-benzodioxin-5-yl)-5-fluoro-N-{3-[(methylsulfonyl)methyl]phenyl}pyrimidin-2-amine | 6 nM | 120 nM | 5 nM |
| 14 N-{3-[(Cyclopropylsulfonyl)methyl]phenyl}-5-fluoro-4-(4-fluoro-2-methoxyphenyl)pyrimidin-2-amine | 8 nM | 780 nM | 40 nM |
| 15 N-{3-[(Benzylsulfonyl)methyl]phenyl}-5-fluoro-4-(4-fluoro-2-methoxyphenyl)pyrimidin-2-amine | 10 nM | 1100 nM | 83 nM |
| 16 5-Fluoro-4-{2-fluoro-4-[(3-fluorobenzyl)oxy]phenyl}-N-{3-[(methylsulfonyl)methyl]phenyl}pyrimidin-2-amine | 8 nM | 820 nM | 19 nM |
| 17 5-Fluoro-4-{2-fluoro-4-[(3-fluorobenzyl)oxy]phenyl}-N-{3-[(methylsulfonyl)methyl]phenyl}pyrimidin-2-amine | 12 nM | 3800 nM | 6 nM |
| 18 5-Fluoro-4-{2-fluoro-4-[(3-fluorobenzyl)oxy]phenyl}-N-{3-[(methylsulfonyl)-methyl]phenyl}pyrimidin-2-amine | 19 nM | 880 nM | 8 nM |

The $IC_{50}$ (inhibitory concentration at 50% of maximal effect) values are indicated in nM or μM, "n.t." means that the compounds have not been tested in this assay.
①: Example Number
②: CDK9: CDK9/CycT1 kinase assay as described under Method 1a. of Materials and Methods
③: CDK2: CDK2/CycE kinase assay as described under Method 2. of Materials and Methods
④: high ATP CDK9: CDK9/CycT1 kinase assay as described under Method 1b. of Materials and Methods

TABLE 3

Inhibition of proliferation of HeLa, HeLa-MaTu-ADR, NCI-H460, DU145, Caco-2 and B16F10 cells by compounds according to the present invention, determined as described under Method 3. of Materials and Methods.

| ① Name of compound | ② | ③ | ④ | ⑤ | ⑥ | ⑦ | ⑧ |
|---|---|---|---|---|---|---|---|
| 1 5-Fluoro-4-(4-fluoro-2-methoxyphenyl)-N-{3-[(methylsulfonyl)methyl]phenyl}pyrimidin-2-amine | 0.29 | 0.17 | 0.33 | 0.29 | 0.26 | 0.31 | n.t. |
| 2 4-[2-(Benzyloxy)-4-fluorophenyl]-5-fluoro-N-{3-[(methylsulfonyl)methyl]phenyl}pyrimidin-2-amine | 0.35 | 0.30 | 0.37 | 0.41 | 0.49 | 0.82 | n.t. |
| 3 4-[2-(Benzyloxy)-4-fluorophenyl]-5-fluoro-N-(3-{[(2-methoxyethyl)sulfonyl]methyl}phenyl)pyrimidin-2-amine | 1.2 | 1.0 | 1.2 | 1.3 | 1.1 | 1.2 | n.t. |
| 7 5-Fluoro-4-(4-fluoro-2-methoxyphenyl)-N-{3-[(propan-2-ylsulfonyl)methy]phenyl}pyrimidin-2-amine | 1.1 | n.t. | n.t. | n.t. | n.t. | n.t. | n.t. |
| 8 2-[(3-{[5-fluoro-4-(4-fluoro-2-methoxyphenyl)pyrimidin-2-yl]amino}benzyl)sulfonyl]ethanol | 1.0 | 0.38 | 0.71 | 0.64 | 0.71 | 0.95 | n.t. |
| 9 4-(3,4-Dihydro-2H-chromen-8-yl)-5-fluoro-N-{3-[(methylsulfonyl)methyl]phenyl}pyrimidin-2-amine | 0.36 | 0.20 | 0.34 | 0.32 | 0.27 | 0.34 | n.t. |
| 10 N-{3-[(Cyclopropylsulfonyl)methyl]phenyl}-4-(3,4-dihydro-2H-chromen-8-yl)-5-fluoropyrimidin-2-amine | 1.1 | n.t. | n.t. | n.t. | n.t. | n.t. | n.t. |
| 11 4-[2-(Benzyloxy)-4-fluorophenyl]-5-fluoro-N-{3-fluoro-5-[(methylsulfonyl)methyl]phenyl}pyrimidin-2-amine | 1.0 | n.t. | n.t. | n.t. | n.t. | n.t. | n.t. |
| 12 5-Fluoro-4-(4-fluoro-2-methoxyphenyl)-N-{3-fluoro-5-[(methylsulfonyl)methyl]phenyl}pyrimidin-2-amine | 0.11 | 0.12. | 0.36 | 0.31 | 0.38 | 0.36 | 0.11 |
| 13 4-(2,3-Dihydro-1,4-benzodioxin-5-yl)-5-fluoro-N-{3-[(methylsulfonyl)methyl]phenyl}pyrimidin-2-amine | 0.21 | 0.19 | 0.34 | 0.31 | 0.22 | 0.51 | n.t. |
| 14 N-{3-[(Cyclopropylsulfonyl)methyl]phenyl}-5-fluoro-4-(4-fluoro-2-methoxyphenyl)pyrimidin-2-amine | 0.67 | n.t. | n.t. | n.t. | n.t | n.t | n.t. |

TABLE 3-continued

Inhibition of proliferation of HeLa, HeLa-MaTu-ADR, NCI-H460, DU145, Caco-2 and B16F10 cells by compounds according to the present invention, determined as described under Method 3. of Materials and Methods.

| ① Name of compound | ② | ③ | ④ | ⑤ | ⑥ | ⑦ | ⑧ |
|---|---|---|---|---|---|---|---|
| 15 N-{3-[(Benzylsulfonyl)methyl]phenyl}-5-fluoro-4-(4-fluoro-2-methoxyphenyl)pyrimidin-2-amine | 1.8 | n.t. | n.t. | n.t. | n.t. | n.t. | n.t. |
| 16 5-Fluoro-4-[4-fluoro-2-(pyridin-3-ylmethoxy)phenyl]-N-{3-[(methylsulfonyl)-methyl]phenyl}pyrimidin-2-amine | 0.38 | 0.35 | 0.32 | 0.3 | 0.44 | 0.41 | n.t. |
| 17 5-Fluoro-4-{2-fluoro-4-[(4-fluorobenzyl)oxy]phenyl}-N-{3-[(methylsulfonyl)-methyl]phenyl}pyrimidin-2-amine | 0.62 | 0.35 | 0.46 | 0.5 | 0.55 | 0.49 | n.t. |
| 18 5-Fluoro-4-{2-fluoro-4-[(3-fluorobenzyl)oxy]phenyl}-N-{3-[(methylsulfonyl)-methyl]phenyl}pyrimidin-2-amine | 0.12 | 0.04 | 0.1 | 0.14 | 0.1 | 0.11 | n.t. |

All IC$_{50}$ (inhibitory concentration at 50% of maximal effect) values are indicated in μM, "n.t." means that the compounds have not been tested in this assay.

①: Example Number
②: Inhibition of HeLa cell proliferation
③: Inhibition of HeLa-MaTu-ADR cell proliferation
④: Inhibition of NCI-H460 cell proliferation
⑤: Inhibition of DU145 cell proliferation
⑥: Inhibition of Caco-2 cell proliferation
⑦: Inhibition of B16F10 cell proliferation
⑧: Inhibition of A2780 cell proliferation

TABLE 4

Caco-2 permeation of compounds according to the present invention, determined as described under Method 4. of Materials and Methods.

| ① Name of compound | ② | ③ | ④ | ⑤ |
|---|---|---|---|---|
| 1 5-Fluoro-4-(4-fluoro-2-methoxyphenyl)-N-{3-[(methylsulfonyl)methyl]phenyl}pyrimidin-2-amine | 2 | 206 | 85 | 0.41 |
| 12 5-Fluoro-4-(4-fluoro-2-methoxyphenyl)-N-{3-fluoro-5-[(methylsulfonyl)methyl]phenyl}pyrimidin-2-amine | 2 | 97 | 31 | 0.32 |

①: Example Number
②: Concentration of test compound indicated in μM.
③: P$_{app}$ A-B (M$_{ari}$) indicated in [nm/s]
④: P$_{app}$ B-A (M$_{ari}$) indicated in [nm/s]
⑤: Efflux ratio

The invention claimed is:

1. A compound of general formula (I)

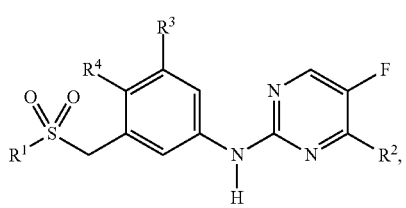

(I)

wherein $R^1$ represents a group selected from $C_1$-$C_6$-alkyl-, $C_3$-$C_7$-cycloalkyl-, heterocyclyl-, phenyl, heteroaryl, phenyl-$C_1$-$C_3$-alkyl- or heteroaryl-$C_1$-$C_3$-alkyl-,
wherein said group is optionally substituted with one or two or three substituents, identically or differently, selected from the group of hydroxy, cyano, halogen, halo-$C_1$-$C_3$-alkyl-, $C_1$-$C_6$-alkoxy-, $C_1$-$C_3$-fluoroalkoxy-, —NH$_2$, alkylamino-, dialkylamino-, acetylamino-, N-methyl-N-acetylamino-, cyclic amines;

$R^2$ represents a group selected from

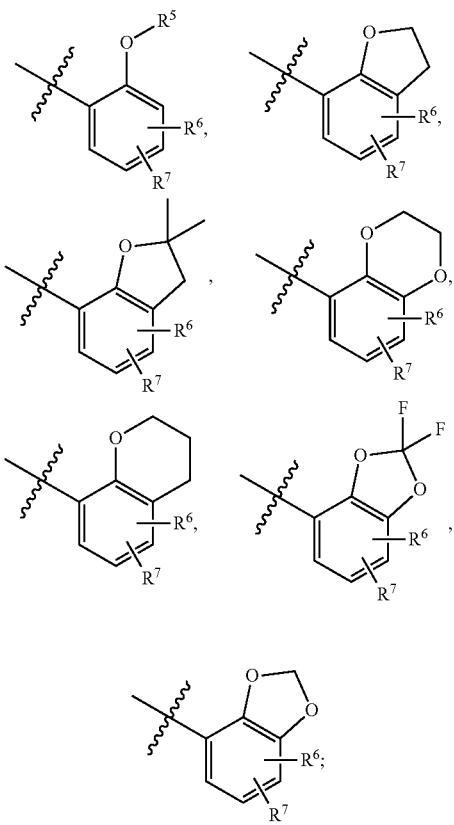

R³, R⁴ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;

R⁵ represents a group selected from
a) a $C_1$-$C_6$-alkyl group, which is optionally substituted with one or two or three substituents, identically or differently, selected from halogen, hydroxy, —NH₂, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, heterocyclyl-, phenyl, heteroaryl, wherein said $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, —NH₂, alkylamino-, dialkylamino-, acetylamino-, N-methyl-N-acetylamino-, cyclic amines, halo-$C_1$-$C_3$-alkyl-, $C_1$-$C_3$-fluoroalkoxy-;
b) a $C_3$-$C_7$-cycloalkyl- group, which is optionally substituted with one or two or three substituents, identically or differently, selected from the group of halogen, hydroxy, —NH₂, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-;
c) a heterocyclyl- group, which is optionally substituted with one or two or three substituents, identically or differently, selected from the group of halogen, hydroxy, —NH₂, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-;
d) a phenyl group, which is optionally substituted with one or two or three substituents, identically or differently, selected from the group of halogen, hydroxy, —NH₂, alkylamino-, dialkylamino-, acetylamino-, N-methyl-N-acetylamino-, cyclic amines, cyano, $C_1$-$C_3$-alkyl-, halo $C_1$-$C_3$ alkyl $C_1$-$C_3$-fluoroalkoxy-, $C_1$-$C_3$-alkoxy-;
e) a heteroaryl group, which is optionally substituted with one or two or three substituents, identically or differently, selected from the group of halogen, hydroxy, —NH₂, alkylamino-, dialkylamino-, acetylamino-, N-methyl-N-acetylamino-, cyclic amines, cyano, $C_1$-$C_3$-alkyl-, halo $C_1$-$C_3$ alkyl $C_1$-$C_3$-fluoroalkoxy-, $C_1$-$C_3$-alkoxy-;
f) a phenyl-$C_1$-$C_3$-alkyl- group, which phenyl group is optionally substituted with one or two or three substituents, identically or differently, selected from the group of halogen, hydroxy, —NH₂, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
g) a heteroaryl-$C_1$-$C_3$-alkyl- group, which heteroaryl group is optionally substituted with one or two or three substituents, identically or differently, selected from the group of halogen, hydroxy, —NH₂, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
h) a $C_3$-$C_6$-cycloalkyl-$C_1$-$C_3$-alkyl- group, which $C_3$-$C_6$-cycloalkyl group is optionally substituted with one or two or three substituents, identically or differently, selected from halogen, $C_1$-$C_3$-alkyl-, $C_1$-$C_3$, $C_1$-$C_3$-alkoxy-, halo-$C_1$-$C_3$-alkyl-, $C_1$-$C_3$-fluoroalkoxy-;
i) a heterocyclyl-$C_1$-$C_3$-alkyl- group, which heterocyclyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy;
j) phenyl-cyclopropyl- group, which phenyl group is optionally substituted with one or two or three substituents, identically or differently, selected from the group of halogen, hydroxy, NH₂, alkylamino-, dialkylamino-, acetylamino-, N-methyl-N-acetylamino-, cyclic amines, cyano, $C_1$-$C_3$-alkyl-, halo $C_1$-$C_3$ alkyl $C_1$-$C_3$-fluoroalkoxy-, $C_1$-$C_3$-alkoxy-;
k) a heteroaryl-cyclopropyl- group, which heteroaryl group is optionally substituted with one or two or three substituents, identically or differently, selected from the group of halogen, hydroxy, NH₂, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

R⁶, R⁷ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;

or its salts, solvates or salts of solvates.

2. The compound according to claim 1, wherein
R¹ represents a group selected from $C_1$-$C_6$-alkyl-, $C_3$-$C_5$-cycloalkyl-, wherein said group is optionally substituted with one or two substituents, identically or differently, selected from the group of hydroxy, $C_1$-$C_2$-alkoxy-, halo-$C_1$-$C_2$-alkyl-, $C_1$-$C_2$-fluoroalkoxy-;
R² represents a group selected from

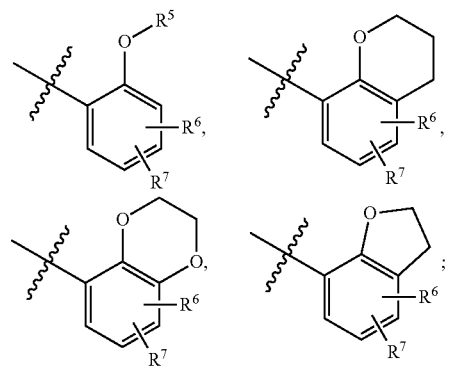

R³ represents a hydrogen atom or a fluoro atom;
R⁴ represents a hydrogen atom or a fluoro atom;
R⁵ represents a group selected from
a) a $C_1$-$C_6$-alkyl group, which is optionally substituted with one or two or three substituents, identically or differently, selected from halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_3$-$C_7$-cycloalkyl-, heterocyclyl-, phenyl, heteroaryl, wherein said $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, dialkylamino-, acetylamino-, N-methyl-N-acetylamino-, cyclic amines, halo-$C_1$-$C_3$-alkyl-, $C_1$-$C_3$-fluoroalkoxy-;
b) a phenyl-$C_1$-$C_3$-alkyl- group, which phenyl group is optionally substituted with one or two or three substituents, identically or differently, selected from the group of halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
c) a heteroaryl-$C_1$-$C_3$-alkyl- group, which heteroaryl group is optionally substituted with one or two or three substituents, identically or differently, selected from the group of halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
d) a $C_3$-$C_6$-cycloalkyl-$C_1$-$C_3$-alkyl- group, which $C_3$-$C_6$-cycloalkyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;
e) a heterocyclyl-$C_1$-$C_3$-alkyl- group, which heterocyclyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;
f) phenyl-cyclopropyl- group, which phenyl group is optionally substituted with one or two or three substituents, identically or differently, selected from the group of halogen, hydroxy, —$NH_2$, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
g) a heteroaryl-cyclopropyl- group, which heteroaryl group is optionally substituted with one or two or three substituents, identically or differently, selected from the group of halogen, hydroxy, —$NH_2$, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;
or its salts, solvates or salts of solvates.

3. The compound according to claim 1, wherein
$R^1$ represents a group selected from $C_1$-$C_6$-alkyl-, $C_3$-$C_5$-cycloalkyl-, wherein said group is optionally substituted with one or two substituents, identically or differently, selected from the group of hydroxy, $C_1$-$C_6$-alkoxy-;
$R^2$ represents a group selected from

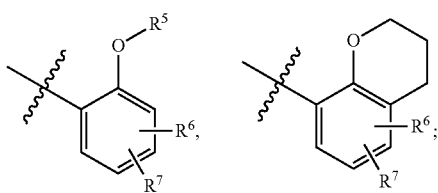

$R^3$ represents a hydrogen atom or fluoro atom;
$R^4$ represents a hydrogen atom or a fluoro atom;

$R^5$ represents a group selected from
a) a $C_1$-$C_3$-alkyl group, which is optionally substituted with one or two or three substituents, identically or differently, selected from halogen, cyano, halo-$C_1$-$C_3$-alkyl-;
b) a phenyl-$C_1$-$C_3$-alkyl- group, which phenyl group is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-;
c) a heteroaryl-$C_1$-$C_3$-alkyl- group, which heteroaryl group is optionally substituted with one or two substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-;
d) a $C_3$-$C_6$-cycloalkyl-$C_1$-$C_3$-alkyl- group, which $C_3$-$C_6$-cycloalkyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;
e) a heterocyclyl-$C_1$-$C_3$-alkyl- group, which heterocyclyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;
f) phenyl-cyclopropyl- group, which phenyl group is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-;
g) a heteroaryl-cyclopropyl- group, which heteroaryl group is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-;
$R^6$, $R^7$ represent, independently from each other, a group selected from a hydrogen atom or a fluoro atom;
or its salts, solvates or salts of solvates.

4. The compound according to claim 1, wherein
$R^1$ represents a group selected from $C_1$-$C_6$-alkyl-, $C_3$-$C_5$-cycloalkyl-, wherein said group is optionally substituted with one or two substituents, identically or differently, selected from the group of hydroxy, $C_1$-$C_6$-alkoxy-;
$R^2$ represents a group selected from

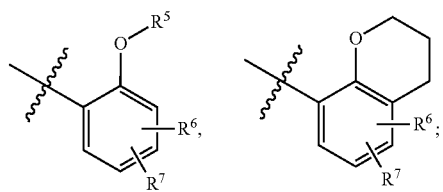

$R^3$ represents a hydrogen atom or fluoro atom;
$R^4$ represents a hydrogen atom;
$R^5$ represents a group selected from
a) a $C_1$-$C_3$-alkyl group;
b) a phenyl-$C_1$-$C_3$-alkyl- group;
$R^6$, $R^7$ represent, independently from each other, a group selected from a hydrogen atom or fluoro atom;
or its salts, solvates or salts of solvates.

5. The compound according to claim 1, wherein
$R^1$ represents a group selected from methyl, ethyl, propan-2yl-, cyclopropyl, tert-butyl-, cyclohexyl, wherein said group is optionally substituted with one substituent selected from the group of hydroxy, methoxy-, $C_1$-$C_6$-alkoxy-;

$R^2$ represents a group selected from 4-fluoro-2-methoxyphenyl-, 2-(benzyloxy)-4-fluorophenyl-, 3,4-dihydro-2H-chromen-8-yl-;

$R^3$ represents a hydrogen atom or fluoro atom;

$R^4$ represents a hydrogen atom;

or its salts, solvates or salts of solvates.

6. The compound according to claim 1, wherein
$R^1$ represents a methyl group;
$R^2$ represents a group selected from 4-fluoro-2-methoxyphenyl-, 2-(benzyloxy)-4-fluorophenyl-, 3,4-dihydro-2H-chromen-8-yl-;
$R^3$ represents a hydrogen atom or fluoro atom;
$R^4$ represents a hydrogen atom;
or its salts, solvates or salts of solvates.

7. The compound according to claim 1, which is selected from

5-Fluoro-4-(4-fluoro-2-methoxyphenyl)-N-{3-[(methylsulfonyl)methyl]phenyl}pyrimidin-2- amine, 4-[2-(Benzyloxy)-4-fluorophenyl]-5- fluoro-N-{3-[(methylsulfonyl)methyl]phenyl}pyrimidin-2-amine, 4-[2-(Benzyloxy)-4-fluorophenyl]-5-fluoro-N-(3-{[(2-methoxyethyl)sulfonyl]methyl}phenyl) pyrimidin-2-amine, 4-[2-(Benzyloxy)-4-fluorophenyl]-N-{3-[(tert-butylsulfonyl)methyl]phenyl}-5-fluoropyrimidin-2-amine, 4-[2-(Benzyloxy)-4-fluorophenyl]-5-fluoro-N-{3-[(propan-2-ylsulfonyl)methyl]phenyl}pyrimidin-2-amine, 4-[2-(Benzyloxy)-4-fluorophenyl]-N-{3-[(cyclohexylsulfonyl)methyl]phenyl}-5-fluoropyrimidin-2-amine, 5-Fluoro-4-(4-fluoro-2-methoxyphenyl)-N-{3-[(propan-2-ylsulfonyl)methyl]phenyl}pyrimidin-2-amine, 2-[(3-{[5-fluoro-4-(4-fluoro-2-methoxyphenyl)pyrimidin-2-yl]amino}benzyl)sulfonyl]ethanol, 4-(3,4-Dihydro-2H-chromen-8-yl)-5-fluoro-N-{3-[(methylsulfonyl)methyl]phenyl}pyrimidin-2-amine, N-{3-[(Cyclopropylsulfonyl)methyl]phenyl}-4-(3,4-dihydro-2H-chromen-8-yl)-5-fluoropyrimidin-2-amine, 4-[2-(Benzyloxy)-4-fluorophenyl]-5-fluoro-N-{3-fluoro-5-[(methylsulfonyl)methyl]phenyl}pyrimidin-2-amine, 5-Fluoro-4-(4-fluoro-2-methoxyphenyl)-N-{3-fluoro-5-[(methylsulfonyl)methyl]phenyl}pyrimidin-2-amine, 4-(2,3-Dihydro-1,4-benzodioxin-5-yl)-5-fluoro-N-{3-[(methylsulfonyl)methyl]phenyl}pyrimidin-2-amine, N-{3-[(Cyclopropylsulfonyl)methyl]phenyl}-5-fluoro-4-(4-fluoro-2-methoxyphenyl)pyrimidin-2-amine, N-{3-[(Benzylsulfonyl)methyl]phenyl}-5-fluoro-4-(4-fluoro-2-methoxyphenyl)pyrimidin-2-amine, 5-Fluoro-4-[4-fluoro-2-(pyridin-3-ylmethoxy)phenyl]-N-{3-[(methylsulfonyl)-methyl]phenyl}pyrimidin-2-amine, 5-Fluoro-4-{2-fluoro-4-[(4-fluorobenzyl)oxy]phenyl}-N-{3-[(methylsulfonyl)-methyl]phenyl}pyrimidin-2-amine, and 5-Fluoro-4-{ 2-fluoro-4-[(3-fluorobenzyl)oxy]phenyl}-N-{3-[(methylsulfonyl)-methyl]phenyl}pyrimidin-2-amine, or its salts, solvates or salts of solvates.

8. A method for the treatment of lung carcinomas, prostate carcinomas, cervical carcinomas, colorectal carcinomas, melanomas or ovarian carcinomas comprising administering to a patient in need thereof a pharmaceutically effective amount of a compound according to claim 1.

9. A pharmaceutical combination comprising a compound according to claim 1 in combination with at least one further active ingredients.

10. A pharmaceutical composition comprising a compound according to claim 1 in combination with an inert, nontoxic, pharmaceutically suitable adjuvant.

11. A method for the preparation of a compound of formula (I) according to claim 1, in which method a compound of formula (3)

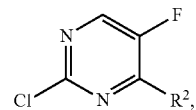

in which $R^2$ is as defined in claim 1, is reacted with a compound of formula (4)

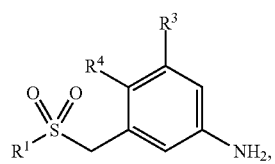

in which $R^1$, $R^3$ and $R^4$ are as defined in claim 1, thus providing a compound of general formula (I), which is optionally reacted with the corresponding (i) solvents and/or (ii) bases or acids to form a solvate, salt and/or solvate of a salt of the compound of formula (I).

* * * * *